United States Patent
Maienfisch et al.

(10) Patent No.: US 9,045,422 B2
(45) Date of Patent: Jun. 2, 2015

(54) PIPERIDINE DERIVATIVES WITH PESTICIDAL PROPERTIES

(71) Applicants: Peter Maienfisch, Stein (CH); Louis-Pierre Molleyres, Basel (CH); Jerome Cassayre, Stein (CH); Fredik Cederbaum, Stein (CH); Camilla Corsi, Basel (CH); Thomas Pitterna, Stein (CH)

(72) Inventors: Peter Maienfisch, Stein (CH); Louis-Pierre Molleyres, Basel (CH); Jerome Cassayre, Stein (CH); Fredik Cederbaum, Stein (CH); Camilla Corsi, Basel (CH); Thomas Pitterna, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 13/949,803

(22) Filed: Jul. 24, 2013

(65) Prior Publication Data

US 2013/0310399 A1    Nov. 21, 2013

Related U.S. Application Data

(62) Division of application No. 13/371,002, filed on Feb. 10, 2012, now Pat. No. 8,546,569, which is a division of application No. 11/571,303, filed as application No. PCT/IB2005/002002 on Jun. 22, 2005, now Pat. No. 8,129,534.

(30) Foreign Application Priority Data

Jun. 28, 2004   (GB) .................................. 0414438.2

(51) Int. Cl.
| | |
|---|---|
| *C07D 211/68* | (2006.01) |
| *C07D 211/34* | (2006.01) |
| *A01N 43/40* | (2006.01) |
| *C07D 211/52* | (2006.01) |
| *C07D 401/04* | (2006.01) |
| *C07D 401/12* | (2006.01) |
| *C07D 401/14* | (2006.01) |

(52) U.S. Cl.
CPC .............. *C07D 211/34* (2013.01); *A01N 43/40* (2013.01); *C07D 211/52* (2013.01); *C07D 401/04* (2013.01); *C07D 401/12* (2013.01); *C07D 401/14* (2013.01)

(58) Field of Classification Search
CPC .............. C07D 401/02; C07D 401/04
See application file for complete search history.

(56) References Cited

U.S. PATENT DOCUMENTS

| | | |
|---|---|---|
| 3,041,342 A | 6/1962 | Jucker et al. |
| 8,193,362 B2 | 6/2012 | Cassayre et al. |
| 2011/0136866 A1 | 6/2011 | Pitterna et al. |
| 2012/0115884 A1 | 5/2012 | Cassayre et al. |

FOREIGN PATENT DOCUMENTS

| | | |
|---|---|---|
| EP | 0494717 A1 | 7/1992 |
| FR | 1343157 | 12/1962 |
| FR | 1365661 | 7/1963 |
| WO | 03009847 A1 | 2/2003 |

OTHER PUBLICATIONS

Berridge et al., J. Med. Chem., 1993, 36, 1284-1290.
Burger, "Isoterism and bioisoterism in drug design", in Progress in Drug Research, 1991, 287-328.
Elliott et al., Bioorganic & Medicinal Chemistry Letters 8, 1998, 1851-1856.
Patani et al., Chem. Rev., 1996, 96, 3147-3176.

*Primary Examiner* — Heidi Reese
(74) *Attorney, Agent, or Firm* — Brian D. McAlhaney

(57) ABSTRACT

An insecticidal acaricidal and nematicidal composition of formula I (I)

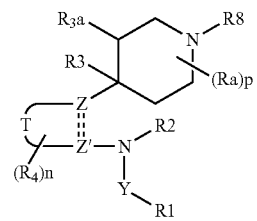

Y is a single bond, C=O, C=S or $S(O)_m$ where m is 0, 1 or 2; the ring

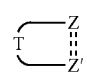

is a 6 membered aromatic ring or is a 5 or 6 membered heteroaromatic ring;
Z and

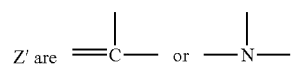

provided that both are not N; $R^1$, $R^2$, $R^3$, $R^{3a}$, $R^4$, $R^8$ and Ra are specified organic groups and n and p are independently 0, 1, 2, 3 or 4; or salts or N-oxides thereof or compositions containing them in controlling insects, acarines, nematodes or molluscs. Novel compounds are also provided.

3 Claims, No Drawings

PIPERIDINE DERIVATIVES WITH PESTICIDAL PROPERTIES

This application is a divisional application of U.S. Ser. No. 13/371,002 filed Feb. 10, 2012, which is a divisional application of U.S. Ser. No. 11/571,303 filed Apr. 27, 2006, which is a 371 of International Application No. PCT/IB2005/002002 filed Jun. 22, 2005, which claims priority to GB 0414438.2 filed Jun. 28, 2004, the contents of which are incorporated herein by reference.

The present invention relates to piperidine derivatives, to processes for preparing them, to insecticidal, acaricidal, molluscicidal and nematicidal compositions comprising them and to methods of using them to combat and contro01 insect, acarine, mollusc and nematode pests.

Piperidine derivatives with fungicidal properties are disclosed in for example in EP494717.

It has now surprisingly been found that certain piperidines have insecticidal properties.

The present invention therefore provides a method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I):

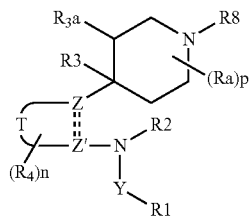

(I)

Y is a single bond, C=O, C=S or $S(O)_m$, where m is 0, 1 or 2; the ring

is a 6 membered aromatic ring or is a 5 or 6 membered heteroaromatic ring;

Z and Z' are joined by a single or a double bond and are

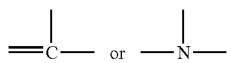

provided that both are not N;

$R^1$ is hydrogen, optionally substituted alkyl, optionally substituted alkoxycarbonyl, optionally substituted alkylcarbonyl, aminocarbonyl, optionally substituted alkylaminocarbonyl, optionally substituted dialkylaminocarbonyl, optionally substituted aryl, optionally substituted heteroaryl, optionally substituted alkoxy, optionally substituted aryloxy, optionally substituted heteroaryloxy, optionally substituted heterocyclyloxy, cyano, optionally substituted alkenyl, optionally substituted alkynyl, optionally substituted cycloalkyl, optionally substituted cycloalkenyl, formyl, optionally substituted heterocyclyl, optionally substituted alkylthio, NO or $NR^{13}R^{14}$ where $R^{13}$ and $R^{14}$ are independently hydrogen, $COR^{15}$, optionally substituted alkyl, optionally substituted aryl, optionally substituted heteroaryl, optionally substituted heterocyclyl or $R^{13}$ and $R^{14}$ together with the N atom to which they are attached form a group —N=C($R^{16}$)—$NR^{17}R^{18}$ or $R^{13}$ and $R^{14}$ together with the N atom to which they are attached form a five, six or seven-membered heterocyclic ring which may contain one or two further heteroatoms selected from O, N or S and which may be optionally substituted by one or two $C_{1-6}$ alkyl groups; $R^{15}$ is H, optionally substituted alkyl, optionally substituted alkoxy, optionally substituted aryl, optionally substituted aryloxy optionally substituted heteroaryl, optionally substituted heteroaryloxy or $NR^{19}R^{20}$; $R^{16}$, $R^{17}$ and $R^{18}$ are each independently H or lower alkyl; $R^{19}$ and $R^{20}$ are independently optionally substituted alkyl, optionally substituted aryl or optionally substituted heteroaryl;

$R^2$ is H, hydroxy, optionally substituted alkoxy or optionally substituted alkyl; or $R^1$ and $R^2$ together with the groups Y and N form a 5- or 6-membered heterocyclic ring which may optionally contain one further heteroatom selected from O, N or S and which may be optionally substituted by $C_{1-4}$ alkyl, $C_{1-4}$ haloalkyl or halogen;

$R^3$ is H, OH, halogen or optionally substituted alkyl;

$R^{3a}$ is H or $R^3$ and $R^{3a}$ together form a bond;

each $R^4$ is independently halogen, nitro, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio or $R^{21}R^{22}N$ where $R^{21}$ and $R^{22}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkyl, $C_{1-6}$ alkoxy($C_{1-6}$)alkyl, $C_{1-6}$ alkoxycarbonyl or $R^{21}$ and $R^{22}$ together with the N atom to which they are attached form a five, six or seven-membered heterocyclic ring which may contain one or two further heteroatoms selected from O, N or S and which may be optionally substituted by one or two $C_{1-6}$ alkyl groups, or 2 adjacent groups $R^4$ together with the carbon atoms to which they are attached form a 4, 5, 6, or 7 membered carbocyclic or heterocyclic ring which may be optionally substituted by halogen; n is 0, 1, 2, 3 or 4;

$R^8$ is optionally substituted alkyl, optionally substituted alkenyl, optionally substituted alkynyl, optionally substituted cycloalkyl, optionally substituted aryl, optionally substituted alkoxy, optionally substituted aryloxy, optionally substituted alkoxycarbonyl, optionally substituted alkylcarbonyl or optionally substituted alkenylcarbonyl;

each Ra is independently halogen, hydroxy, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio, optionally substituted arylthio or $R^{23}R^{24}N$ where $R^{23}$ and $R^{24}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkyl, $C_{1-6}$ alkoxy($C_{1-6}$)alkyl, $C_{1-6}$ alkoxycarbonyl or $R^{23}$ and $R^{24}$ together with the N atom to which they are attached form a five, six or seven-membered heterocyclic ring which may contain one or two further heteroatoms selected from O, N or S and which may be optionally substituted by one or two $C_{1-6}$ alkyl groups, or two Ra groups attached to the same carbon atom are =O, =S, =NRb, =CRcRd where Rb, Rc and Rd are independently H or optionally substituted alkyl; p is 0, 1, 2, 3 or 4 or salts or N-oxides thereof.

The compounds of formula (I) may exist in different geometric or optical isomers or tautomeric forms. This invention covers all such isomers and tautomers and mixtures thereof in all proportions as well as isotopic forms such as deuterated compounds.

Each alkyl moiety either alone or as part of a larger group (such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. The alkyl groups are suitably $C_1$ to $C_{12}$ alkyl groups, but are preferably $C_1$-$C_{10}$, more preferably $C_1$-$C_8$, even more preferably $C_1$-$C_6$ and most preferably $C_1$-$C_4$ alkyl groups.

When present, the optional substituents on an alkyl moiety (alone or as part of a larger group such as alkoxy, alkoxycarbonyl, alkylcarbonyl, alkylaminocarbonyl, dialkylaminocarbonyl) include one or more of halogen, nitro, cyano, NCS—, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy($C_{1-10}$)alkoxy, tri($C_{1-4}$)alkylsilyl($C_{1-6}$)alkoxy, $C_{1-6}$ alkoxycarbonyl($C_{1-10}$)alkoxy, $C_{1-10}$ haloalkoxy, aryl($C_{1-4}$)-alkoxy (where the aryl group is optionally substituted), $C_{3-7}$ cycloalkyloxy (where the cycloalkyl group is optionally substituted with $C_{1-6}$ alkyl or halogen), $C_{2-10}$ alkenyloxy, $C_{2-10}$ alkynyloxy, SH, $C_{1-10}$ alkylthio, $C_{1-10}$ haloalkylthio, aryl($C_{1-4}$)alkylthio (where the aryl group is optionally substituted), $C_{3-7}$ cycloalkylthio (where the cycloalkyl group is optionally substituted with $C_{1-6}$ alkyl or halogen), tri($C_{1-4}$)alkylsilyl($C_{1-6}$)alkylthio, arylthio (where the aryl group is optionally substituted), $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl (where the aryl group may be optionally substituted), tri($C_{1-4}$)alkylsilyl, aryldi($C_{1-4}$)alkylsilyl, ($C_{1-4}$)alkyldiarylsilyl, triarylsilyl, $C_{1-10}$ alkylcarbonyl, $HO_2C$, $C_{1-10}$ alkoxycarbonyl, aminocarbonyl, $C_{1-6}$ alkylaminocarbonyl, di($C_{1-6}$ alkyl)aminocarbonyl, N—($C_{1-3}$ alkyl)-N—($C_{1-3}$ alkoxy)aminocarbonyl, $C_{1-6}$ alkylcarbonyloxy, arylcarbonyloxy (where the aryl group is optionally substituted), di($C_{1-6}$)alkylaminocarbonyloxy, oximes such as =NOalkyl, =NOhaloalkyl and =NOaryl (itself optionally substituted), aryl (itself optionally substituted), heteroaryl (itself optionally substituted), heterocyclyl (itself optionally substituted with $C_{1-6}$ alkyl or halogen), aryloxy (where the aryl group is optionally substituted), heteroaryloxy, (where the heteroaryl group is optionally substituted), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, N—($C_{1-6}$)alkylcarbonyl-N—($C_{1-6}$)alkylamino, $C_{2-6}$ alkenylcarbonyl, $C_{2-6}$ alkynylcarbonyl, $C_{3-6}$ alkenyloxycarbonyl, $C_{3-6}$ alkynyloxycarbonyl, aryloxycarbonyl (where the aryl group is optionally substituted) and arylcarbonyl (where the aryl group is optionally substituted).

Alkenyl and alkynyl moieties can be in the form of straight or branched chains, and the alkenyl moieties, where appropriate, can be of either the (E)- or (Z)-configuration. Examples are vinyl, allyl and propargyl.

When present, the optional substituents on alkenyl or alkynyl include those optional substituents given above for an alkyl moiety.

In the context of this specification acyl is optionally substituted $C_{1-6}$ alkylcarbonyl (for example acetyl), optionally substituted $C_{2-6}$ alkenylcarbonyl, optionally substituted $C_{2-6}$ alkynylcarbonyl, optionally substituted arylcarbonyl (for example benzoyl) or optionally substituted heteroarylcarbonyl.

Halogen is fluorine, chlorine, bromine or iodine.

Haloalkyl groups are alkyl groups which are substituted with one or more of the same or different halogen atoms and are, for example, $CF_3$, $CF_2Cl$, $CF_3CH_2$ or $CHF_2CH_2$.

In the context of the present specification the terms "aryl", "aromatic ring" and "aromatic ring system" refer to ring systems which may be mono-, bi- or tricyclic. Examples of such rings include phenyl, naphthalenyl, anthracenyl, indenyl or phenanthrenyl. A preferred aryl group is phenyl. In addition, the terms "heteroaryl", "heteroaromatic ring" or "heteroaromatic ring system" refer to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole quinolinyl, isoquinolinyl, cinnolinyl, phthalazinyl, quinazolinyl, quinoxalinyl, naphthyridinyl, benzotriazinyl, purinyl, pteridinyl and indolizinyl. Preferred examples of heteroaromatic radicals include pyridyl, pyrimidyl, triazinyl, thienyl, furyl, oxazolyl, isoxazolyl, 2,1,3-benzoxadiazole and thiazolyl.

The terms heterocycle and heterocyclyl refer to a non-aromatic ring containing up to 10 atoms including one or more (preferably one or two) heteroatoms selected from O, S and N. Examples of such rings include 1,3-dioxolane, tetrahydrofuran and morpholine.

When present, the optional substituents on heterocyclyl include $C_{1-6}$ alkyl and $C_{1-6}$ haloalkyl as well as those optional substituents given above for an alkyl moiety.

Cycloalkyl includes cyclopropyl, cyclopentyl and cyclohexyl.

Cycloalkenyl includes cyclopentenyl and cyclohexenyl.

When present, the optional substituents on cycloalkyl or cycloalkenyl include $C_{1-3}$ alkyl as well as those optional substituents given above for an alkyl moiety.

Carbocyclic rings include aryl, cycloalkyl and cycloalkenyl groups.

When present, the optional substituents on aryl or heteroaryl are selected independently, from halogen, nitro, cyano, NCS—, $C_{1-6}$ alkyl, $C_{1-6}$ haloalkyl, $C_{1-6}$ alkoxy-($C_{1-6}$) alkyl, $C_{2-6}$ alkenyl, $C_{2-6}$ haloalkenyl, $C_{2-6}$ alkynyl, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy ($C_{1-10}$)alkoxy, tri($C_{1-4}$)alkyl-silyl($C_{1-6}$)alkoxy, $C_{1-6}$ alkoxycarbonyl($C_{1-10}$)alkoxy, $C_{1-10}$ haloalkoxy, aryl($C_{1-4}$)alkoxy (where the aryl group is optionally substituted with halogen or $C_{1-6}$ alkyl), $C_{3-7}$ cycloalkyloxy (where the cycloalkyl group is optionally substituted with $C_{1-6}$ alkyl or halogen), $C_{2-10}$ alkenyloxy, $C_{2-10}$ alkynyloxy, SH, $C_{1-10}$ alkylthio, $C_{1-10}$ haloalkylthio, aryl($C_{1-4}$)alkylthio $C_{3-7}$ cycloalkylthio (where the cycloalkyl group is optionally substituted with $C_{1-6}$ alkyl or halogen), tri($C_{1-4}$)-alkylsilyl($C_{1-6}$)alkylthio, arylthio, $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl, tri($C_{1-4}$)alkylsilyl, aryldi($C_{1-4}$)-alkylsilyl, ($C_{1-4}$)alkyldiarylsilyl, triarylsilyl, $C_{1-10}$ alkylcarbonyl, $HO_2C$, $C_{1-10}$ alkoxycarbonyl, aminocarbonyl, $C_{1-6}$ alkylaminocarbonyl, di($C_{1-6}$ alkyl)-aminocarbonyl, N—($C_{1-3}$ alkyl)-N—($C_{1-3}$ alkoxy)aminocarbonyl, $C_{1-6}$ alkylcarbonyloxy, arylcarbonyloxy, di($C_{1-6}$)alkylamino-carbonyloxy, aryl (itself optionally substituted with $C_{1-6}$ alkyl or halogen), heteroaryl (itself optionally substituted with $C_{1-6}$ alkyl or halogen), heterocyclyl (itself optionally substituted with $C_{1-6}$ alkyl or halogen), aryloxy (where the aryl group is optionally substituted with $C_{1-6}$ alkyl or halogen), heteroaryloxy (where the heteroaryl group is optionally substituted with $C_{1-6}$ alkyl or halogen), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, N—($C_{1-6}$)alkylcarbonyl-N—($C_{1-6}$) alkylamino, arylcarbonyl, (where the aryl group is itself optionally substituted with halogen or $C_{1-6}$ alkyl) or two adjacent positions on an aryl or heteroaryl system may be cyclised to form a 5, 6 or 7 membered carbocyclic or heterocyclic ring, itself optionally substituted with halogen or $C_{1-6}$ alkyl. Further substituents for aryl or heteroaryl include aryl carbonyl amino (where the aryl group is substituted by $C_{1-6}$ alkyl or halogen), ($C_{1-6}$)alkyloxycarbonylamino ($C_{1-6}$)alkyloxycarbonyl-N—($C_{1-6}$)alkylamino, aryloxycarbonylamino (where the aryl group is substituted by $C_{1-6}$ alkyl or halogen), aryloxycarbonyl-N—($C_{1-6}$)alkylamino, (where the aryl group is substituted by $C_{1-6}$ alkyl or halogen), arylsulphonylamino (where the aryl group is substituted by $C_{1-6}$ alkyl or halogen), arylsulphonyl-N—($C_{1-6}$)alkylamino (where the aryl group is substituted by $C_{1-6}$ alkyl or halogen), aryl-N—($C_{1-6}$)alkylamino (where the aryl group is substituted by $C_{1-6}$ alkyl or halogen), arylamino (where the aryl group is substituted by $C_{1-6}$ alkyl or halogen), heteroaryl amino (where the heteroaryl group is substituted by $C_{1-6}$ alkyl or halogen), heterocyclylamino (where the heterocyclyl group is substituted by $C_{1-6}$ alkyl or halogen), aminocarbonylamino, $C_{1-6}$ alkylaminocarbonyl amino, di($C_{1-6}$)alkylaminocarbonyl amino, arylaminocarbonyl amino where the aryl group is substituted by $C_{1-6}$ alkyl or halogen), aryl-N—($C_{1-6}$)alkylaminocarbonylamino where the aryl group is substituted by $C_{1-6}$ alkyl or halogen), $C_{1-6}$ alkylaminocarbonyl-N—($C_{1-6}$)alkyl amino, di($C_{1-6}$)alkylaminocarbonyl-N—($C_{1-6}$)alkyl amino, arylaminocarbonyl-N—($C_{1-6}$)alkyl amino where the aryl group is substituted by $C_{1-6}$ alkyl or halogen) and aryl-N—($C_{1-6}$)alkylaminocarbonyl-N—($C_{1-6}$)alkyl amino where the aryl group is substituted by $C_{1-6}$ alkyl or halogen).

For substituted phenyl moieties, heterocyclyl and heteroaryl groups it is preferred that one or more substituents are independently selected from halogen, $C_{1-6}$ alkyl, $C_{1-6}$ haloalkyl, $C_{1-6}$ alkoxy($C_{1-6}$)alkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{2-6}$ alkenyl, $C_{2-6}$ haloalkenyl, $C_{2-6}$ alkynyl, $C_{3-7}$ cycloalkyl, nitro, cyano, $CO_2H$, $C_{1-6}$ alkylcarbonyl, $C_{1-6}$ alkoxycarbonyl, $R^{25}R^{26}N$ or $R^{27}R^{28}NC(O)$; wherein $R^{25}$, $R^{26}$, $R^{27}$ and $R^{28}$ are, independently, hydrogen or $C_{1-6}$ alkyl. Further preferred substituents are aryl and heteroaryl groups.

Haloalkenyl groups are alkenyl groups which are substituted with one or more of the same or different halogen atoms.

It is to be understood that dialkylamino substituents include those where the dialkyl groups together with the N atom to which they are attached form a five, six or seven-membered heterocyclic ring which may contain one or two further heteroatoms selected from O, N or S and which is optionally substituted by one or two independently selected ($C_{1-6}$)alkyl groups. When heterocyclic rings are formed by joining two groups on an N atom, the resulting rings are suitably pyrrolidine, piperidine, thiomorpholine and morpholine each of which may be substituted by one or two independently selected ($C_{1-6}$) alkyl groups.

Preferably the optional substituents on an alkyl moiety include one or more of halogen, nitro, cyano, $HO_2C$, $C_{1-10}$ alkoxy (itself optionally substituted by $C_{1-10}$ alkoxy), aryl ($C_{1-4}$)alkoxy, $C_{1-10}$ alkylthio, $C_{1-10}$ alkylcarbonyl, $C_{1-10}$ alkoxycarbonyl, $C_{1-6}$ alkylaminocarbonyl, di($C_{1-6}$ alkyl)aminocarbonyl, ($C_{1-6}$)alkylcarbonyloxy, optionally substituted phenyl, heteroaryl, aryloxy, arylcarbonyloxy, heteroaryloxy, heterocyclyl, heterocyclyloxy, $C_{3-7}$ cycloalkyl (itself optionally substituted with ($C_{1-6}$)alkyl or halogen), $C_{3-7}$ cycloalkyloxy, $C_{5-7}$ cycloalkenyl, $C_{1-6}$ alkylsulfonyl, $C_{1-6}$ alkylsulfinyl, tri($C_{1-4}$)alkylsilyl, tri($C_{1-4}$)alkylsilyl($C_{1-6}$)alkoxy, aryldi($C_{1-4}$)alkylsilyl, ($C_{1-4}$)alkyldiarylsilyl and triarylsilyl.

Preferably the optional substituents on alkenyl or alkynyl include one or more of halogen, aryl and $C_{3-7}$ cycloalkyl.

A preferred optional substituent for heterocyclyl is $C_{1-6}$ alkyl.

Preferably the optional substituents for cycloalkyl include halogen, cyano and $C_{1-3}$ alkyl.

Preferably the optional substituents for cycloalkenyl include $C_{1-3}$ alkyl, halogen and cyano.

Preferred groups for T, Y, Ra, $R^1$, $R^2$, $R^3$, $R^{3a}$, $R^4$ and $R^8$ in any combination thereof are set out below.

Preferably Y is a single bond, C=O or C=S.

More preferably Y is a single bond or C=O.

Most preferably Y is C=O.

Preferably $R^1$ is hydrogen, $C_{1-6}$ alkyl, $C_{1-6}$ cyanoalkyl, $C_{1-6}$ haloalkyl, $C_{3-7}$ cycloalkyl($C_{1-4}$)alkyl, $C_{1-6}$ alkoxy($C_{1-6}$)alkyl, heteroaryl($C_{1-6}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), aryl($C_{1-6}$)alkyl (wherein the aryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen), $C_{1-6}$ alkylcarbonylamino($C_{1-6}$)alkyl, aryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen), heteroaryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), $C_{1-6}$ alkoxy, $C_{1-6}$ haloalkoxy, phenoxy (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), heteroaryloxy (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyloxy (optionally substituted by halo, $C_{1-6}$ alkyl, $C_{1-6}$ haloalkyl, $C_{1-6}$ alkoxy or $C_{1-6}$ haloalkoxy), cyano, $C_{2-6}$ alkenyl, $C_{2-6}$ alkynyl, $C_{3-6}$ cycloalkyl, $C_{5-7}$ cycloalkenyl, heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-6}$ alkylthio, $C_{1-6}$ haloalkylthio or NR$^{13}$R$^{14}$ where R$^{13}$ and R$^{14}$ are independently hydrogen, $C_{1-6}$ alkyl, $C_{1-6}$ haloalkyl, $C_{1-6}$ alkoxy($C_{1-6}$)alkyl, phenyl (which may be optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino, dialkylamino or $C_{1-4}$ alkoxycarbonyl), phenyl ($C_{1-6}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), heteroaryl ($C_{1-6}$) alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen) or heteroaryl (which may be optionally substituted by halo, nitro, cyano, $C_{1-6}$ alkyl, $C_{1-6}$ haloalkyl, $C_{1-6}$ alkoxy or $C_{1-6}$ haloalkoxy, $C_{1-4}$ alkoxycarbonyl $C_{1-6}$ alkylcarbonylamino, phenyloxycarbonylamino (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), amino, $C_{1-6}$ alkylamino or phenylamino (wherein the phenyl group is optionally substituted halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino)).

More preferably R$^1$ is $C_{1-6}$ alkyl, $C_{1-6}$ haloalkyl, $C_{1-6}$ alkoxy($C_{1-6}$)alkyl, heteroaryl($C_{1-3}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkoxycarbonyl, or two adjacent positions on the heteroaryl system may be cyclised to form a 5, 6 or 7 membered carbocyclic or heterocyclic ring, itself optionally substituted with halogen), phenyl($C_{1-3}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), phenyl (which may be optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), heteroaryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkoxycarbonyl, or two adjacent positions on the heteroaryl system may be cyclised to form a 5, 6 or 7 membered carbocyclic or heterocyclic ring, itself optionally substituted with halogen), $C_{1-6}$ alkoxy, $C_{1-6}$ haloalkoxy, $C_{2-6}$ alkenyl, heterocyclyl (optionally substituted by halo, cyano, $C_{1-6}$ alkyl, $C_{1-6}$ haloalkyl, $C_{1-6}$ alkoxy or $C_{1-6}$ haloalkoxy), $C_{1-6}$ alkylthio, $C_{1-6}$ haloalkylthio or NR$^{13}$R$^{14}$ where R$^{13}$ and R$^{14}$ are independently hydrogen, $C_{1-6}$ alkyl or $C_{1-6}$ haloalkyl, $C_{1-6}$ alkoxy($C_{1-6}$)alkyl, $C_{2-6}$ alkylcarbonyl, phenylcarbonyl, (where the phenyl is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), phenyl($C_{1-3}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen) or heteroaryl($C_{1-3}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen).

Even more preferably R$^1$ is $C_{1-6}$ alkyl, $C_{1-6}$ haloalkyl, heteroaryl($C_{1-3}$)alkyl (wherein the heteroaryl group may be optionally substituted by halo, cyano, $C_{1-6}$ alkyl, $C_{1-6}$ haloalkyl and where the heteroaryl group is a thiazole, pyridine, pyrimidine, pyrazine or pyridazine ring), heteroaryl (optionally substituted by halo, cyano, $C_{1-6}$ alkyl, $C_{1-6}$ haloalkyl and where the heteroaryl group is a pyridine, pyrimidine, 2,1,3-benzoxadiazole, pyrazine or pyridazine ring), $C_{1-6}$ alkoxy, $C_{1-6}$ alkoxy($C_{1-6}$)alkyl, $C_{1-6}$ alkylamino, $C_{1-6}$ alkyoxy($C_{1-6}$)alkylamino or heteroaryl($C_{1-3}$)alkylamino (wherein the heteroaryl group may be optionally substituted by halo, cyano, $C_{1-6}$ alkyl, $C_{1-6}$ haloalkyl and where the heteroaryl group is a thiazole, pyridine, pyrimidine, pyrazine or pyridazine ring).

Most preferably R$^1$ is pyridyl (optionally substituted by halo, $C_{1-3}$ alkyl or $C_{1-3}$ haloalkyl) especially halo-substituted pyridyl.

It is preferred that R$^2$ is hydrogen, hydroxy, $C_{1-6}$ alkyl or $C_{1-6}$ haloalkyl.

More preferably R$^2$ is hydrogen, $C_{1-4}$ alkyl or $C_{1-4}$ haloalkyl.

Even more preferably R$^2$ is hydrogen or $C_{1-4}$ alkyl.

Yet more preferably R$^2$ is independently hydrogen or methyl.

Most preferably R$^2$ is hydrogen.

It is preferred that R$^3$ is hydrogen, hydroxy, halogen, $C_{1-6}$ alkyl or $C_{1-6}$ haloalkyl.

More preferably R$^3$ is hydrogen, hydroxy, halogen, $C_{1-4}$ alkyl or $C_{1-4}$ haloalkyl.

Even more preferably R$^3$ is hydrogen or $C_{1-4}$ alkyl.

Yet more preferably R$^3$ is independently hydrogen or methyl.

Most preferably R$^3$ is hydrogen.

R$^{3a}$ is preferably hydrogen or R$^3$ and R$^{3a}$ together form a double bond.

Preferably each R$^4$ is independently halogen, cyano, $C_{1-8}$ alkyl, $C_{1-8}$ haloalkyl, cyanoalkyl, $C_{1-6}$ alkoxy($C_{1-6}$)alkyl, $C_{3-7}$ cycloalkyl($C_{1-6}$)alkyl, $C_{5-6}$ cycloalkenyl($C_{1-6}$)alkyl, $C_{3-6}$ alkenyloxy($C_{1-6}$)alkyl, $C_{3-6}$ alkynyloxy($C_{1-6}$)alkyl, aryloxy($C_{1-6}$)alkyl, $C_{1-6}$ carboxyalkyl, $C_{1-6}$ alkylcarbonyl($C_{1-6}$)alkyl, $C_{2-6}$ alkenylcarbonyl($C_{1-6}$)alkyl, $C_{2-6}$ alkynylcarbonyl($C_{1-6}$)-alkyl, $C_{1-6}$ alkoxycarbonyl($C_{1-6}$)alkyl, $C_{3-6}$ alkenyloxycarbonyl($C_{1-6}$)alkyl, $C_{3-6}$ alkynyloxycarbonyl($C_{1-6}$)alkyl, aryloxycarbonyl($C_{1-6}$)alkyl, $C_{1-6}$ alkylthio($C_{1-6}$)

alkyl, $C_{1-6}$ alkylsulfinyl($C_{1-6}$)alkyl, $C_{1-6}$ alkylsulfonyl($C_{1-6}$)alkyl, aminocarbonyl($C_{1-6}$)alkyl, $C_{1-6}$ alkylaminocarbonyl($C_{1-6}$)alkyl, di($C_{1-6}$)alkylaminocarbonyl($C_{1-6}$)alkyl, phenyl($C_{1-4}$)alkyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), heteroaryl($C_{1-4}$)alkyl (wherein the heteroaryl group is optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl($C_{1-4}$)alkyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), $C_{2-6}$ alkenyl, aminocarbonyl($C_{2-6}$)alkenyl, $C_{1-6}$ alkylaminocarbonyl($C_{2-6}$)alkenyl, di($C_{1-6}$)alkylaminocarbonyl($C_{2-6}$)alkenyl, phenyl($C_{2-4}$)-alkenyl, (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), $C_{2-6}$ alkynyl, trimethylsilyl($C_{2-6}$)alkynyl, aminocarbonyl($C_{2-6}$)alkynyl, $C_{1-6}$ alkylaminocarbonyl($C_{2-6}$)alkynyl, di($C_{1-6}$)alkylaminocarbonyl($C_{2-6}$)alkynyl, $C_{1-6}$ alkoxycarbonyl, $C_{3-7}$ cycloalkyl, $C_{3-7}$ halocycloalkyl, $C_{3-7}$ cyanocycloalkyl, $C_{1-3}$ alkyl($C_{3-7}$)-cycloalkyl, $C_{1-3}$ alkyl($C_{3-7}$)halocycloalkyl, phenyl (optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), heteroaryl (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), or 2 adjacent groups $R^4$ together with the carbon atoms to which they are attached form a 4, 5, 6 or 7 membered carbocyclic or heterocyclic ring which may be optionally substituted by halogen, $C_{1-8}$ alkoxy, $C_{1-6}$ haloalkoxy, phenoxy (optionally substituted by halo, nitro, cyano, $C_{1-6}$ alkyl, $C_{1-6}$ haloalkyl, $C_{1-6}$ alkoxy or $C_{1-6}$ haloalkoxy), heteroaryloxy (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-8}$ alkylthio or $R^{19}R^{20}N$ where $R^{19}$ and $R^{20}$ are, independently, hydrogen, $C_{1-8}$ alkyl, $C_{3-7}$ cycloalkyl, $C_{3-6}$ alkenyl, $C_{3-6}$ alkynyl, $C_{2-6}$ haloalkyl, $C_{1-6}$ alkoxycarbonyl or $R^{19}$ and $R^{20}$ together with the N atom to which they are attached form a five, six or seven-membered heterocyclic ring which may contain one or two further heteroatoms selected from O, N or S and which may be optionally substituted by one or two $C_{1-6}$ alkyl groups; n is 0, 1, 2 or 3.

More preferably each $R^4$ is independently halogen, cyano, $C_{1-8}$ alkyl, $C_{1-8}$ haloalkyl, $C_{1-8}$ cyanoalkyl, $C_{1-6}$ alkoxy($C_{1-6}$)alkyl, $C_{2-6}$ alkynyl, trimethylsilyl($C_{2-6}$)alkynyl, $C_{1-6}$ alkoxycarbonyl, $C_{3-7}$ cycloalkyl, $C_{1-3}$ alkyl ($C_{3-7}$) cycloalkyl, phenyl (optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-8}$ alkoxy, $C_{1-6}$ haloalkoxy, phenoxy (optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), heteroaryloxy (optionally substituted by halo, nitro, cyano, $C_{1-3}$ alkyl or $C_{1-3}$ haloalkyl, $C_{1-3}$ alkoxy or $C_{1-3}$ haloalkoxy), di($C_{1-8}$)alkylamino, or 2 adjacent groups $R^4$ together with the carbon atoms to which they are attached form a 4, 5, 6 or 7 membered carbocyclic or heterocyclic ring which may be optionally substituted by halogen; n is 0, 1, 2 or 3.

Even more preferably each $R^4$ is independently halogen, cyano, $C_{1-8}$ alkyl, $C_{1-8}$ haloalkyl, $C_{1-8}$ cyanoalkyl, $C_{1-6}$ alkoxy($C_{1-6}$)alkyl, $C_{2-6}$ alkynyl, heterocyclyl (optionally substituted by $C_{1-6}$ alkyl), $C_{1-8}$ alkoxy, $C_{1-6}$ haloalkoxy, phenoxy (optionally substituted by halo, cyano, $C_{1-3}$ alkyl or $C_{1-3}$ haloalkyl), heteroaryloxy (optionally substituted by halo, cyano, $C_{1-3}$ alkyl or $C_{1-3}$ haloalkyl), di($C_{1-8}$)alkylamino or 2 adjacent groups $R^4$ together with the carbon atoms to which they are attached form a 4, 5, 6 or 7 membered carbocyclic or heterocyclic ring which may be optionally substituted by halogen; n is 0, 1, 2 or 3.

Yet more preferably each $R^4$ is independently fluoro, chloro, bromo, cyano, $C_{1-4}$ alkyl, $C_{1-4}$ haloalkyl, $C_{1-4}$ cyanoalkyl or $C_{1-3}$ alkoxy($C_{1-3}$)alkyl; n is 0, 1, 2 or 3, preferably 0, 1 or 2.

Most preferably each $R^4$ is independently fluoro, chloro, bromo, $C_{1-4}$ alkyl or $C_{1-4}$ haloalkyl; n is 1, 2 or 3, preferably 1 or 2.

Preferably $R^8$ is $C_{1-10}$ alkyl, $C_{1-10}$ haloalkyl, aryl($C_{1-6}$)alkyl (wherein the aryl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), heteroaryl($C_{1-6}$)alkyl (wherein the heteroaryl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), arylcarbonyl-($C_{1-6}$)alkyl (wherein the aryl group may be optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino and the alkyl group may be optionally substituted by aryl), $C_{2-8}$ alkenyl, $C_{2-8}$ haloalkenyl, aryl($C_{2-6}$)-alkenyl (wherein the aryl group is optionally substituted halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino, $C_{1-6}$ alkoxycarbonyl, or two adjacent substituents can cyclise to form a 5, 6 or 7 membered carbocyclic or heterocyclic ring), heteroaryl($C_{2-6}$)-alkenyl (wherein the heteroaryl group is optionally substituted halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino, $C_{1-6}$ alkoxycarbonyl, or two adjacent substituents can cyclise to form a 5, 6 or 7 membered carbocyclic or heterocyclic ring), $C_{2-6}$ alkynyl, phenyl($C_{2-6}$)alkynyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), $C_{3-7}$ cycloalkyl, $C_{1-6}$ alkoxycarbonyl, $C_{1-6}$ alkylcarbonyl, $C_{1-6}$ haloalkylcarbonyl or aryl($C_{2-6}$)alkenylcarbonyl (wherein the aryl group may be optionally substituted halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), or $-C(R^{51})(R^{52})-[CR^{53}=CR^{54}]z-R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is optionally substituted aryl or optionally substituted heteroaryl.

More preferably $R^8$ is phenyl($C_{1-4}$)alkyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), heteroaryl($C_{1-6}$)alkyl (wherein the heteroaryl group is optionally substituted halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), phenyl($C_{2-6}$)alkenyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), heteroaryl($C_{2-6}$)alkenyl (wherein the heteroaryl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino) or phenyl($C_{2-6}$)alkynyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino, or —C(R$^{51}$)(R$^{52}$)—[CR$^{53}$=CR$^{54}$]z-R$^{55}$ where z is 1 or 2, R$^{51}$ and R$^{52}$ are each independently H, halo or C$_{1-2}$ alkyl, R$^{53}$ and R$^{54}$ are each independently H, halogen, C$_{1-4}$ alkyl or C$_{1-4}$ haloalkyl and R$^{55}$ is optionally substituted aryl or optionally substituted heteroaryl.

Most preferably R$^8$ is —C(R$^{51}$)(R$^{52}$)—[CR$^{53}$=CR$^{54}$]z-R$^{55}$ where z is 1 or 2, preferably 1, R$^{51}$ and R$^{52}$ are each independently H or C$_{1-2}$ alkyl, R$^{53}$ and R$^{54}$ are each independently H, halogen, C$_{1-4}$ alkyl or C$_{1-4}$ haloalkyl and R$^{55}$ is phenyl substituted by halogen, C$_{1-4}$ alkyl, C$_{1-4}$ alkoxy, C$_{1-4}$ haloalkyl, C$_{1-4}$ haloalkoxy, CN, NO$_2$, aryl, heteroaryl, amino or dialkylamino or heteroaryl substituted by halogen, C$_{1-4}$ alkyl, C$_{1-4}$ alkoxy, C$_{1-4}$ haloalkyl, C$_{1-4}$ haloalkoxy, CN, NO$_2$, aryl, heteroaryl, amino or dialkylamino.

R$^{51}$ and R$^{52}$ are preferably hydrogen.

R$^{53}$ and R$^{54}$ are preferably hydrogen or halogen, especially hydrogen.

R$^{55}$ is preferably phenyl substituted with one to three substituents selected from halogen, C$_{1-4}$ alkyl, C$_{1-4}$ alkoxy, C$_{1-4}$ haloalkyl, C$_{1-4}$ haloalkoxy, CN, NO$_2$, aryl, heteroaryl, amino or dialkylamino.

Preferably each Ra is independently halo, cyano, C$_{1-3}$ alkyl, hydroxy or two Ra groups together with the carbon atom to which they are attached form =O, =S, =NRb, =CRcRd where Rb, Rc and Rd are independently H or optionally substituted alkyl, and p is 0, 1 or 2.

More preferably each Ra is independently fluoro, methyl, hydroxy or two Ra groups together with the carbon atom to which they are attached form a carbonyl group and p is 0, 1 or 2.

Most preferably p is 0.

It is preferred that that ring

is a 6-membered aromatic ring or is 5 or 6 membered heteroaromatic ring wherein the ring members other than Z and Z' are each independently CH, S, N, NR$^4$, O, or CR$^4$ provided that there are no more than one O or S atoms present in the ring.

More preferably the ring

is a benzene, pyridine, pyrimidine, pyrazine, pyridazine, triazine, pyrrole, imidazole, quinoline, isoquinoline, thiophene, pyrazole, oxazole, thiazole, isoxazole, isothiazole, [1,2,3]triazole, [1,2,3]oxadiazole or [1,2,3]thiadiazole.

Most preferably the ring

is a benzene, pyridine, pyrimidine, pyrazine, thiophene or pyrazole ring, especially a benzene ring.

Certain compounds of formula (I) are novel and as such form a further aspect of the invention. One group of novel compounds are compounds of formula I'

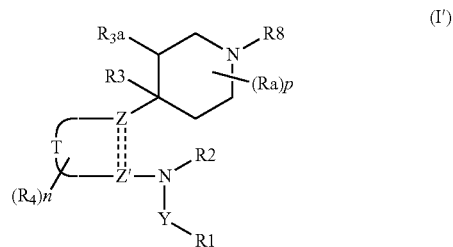

wherein R$^0$, R$^1$, R$^2$, R$^{3a}$, R$^4$Ra, T, Y, n and p are as defined in relation to formula I and R$^8$ is —C(R$^{51}$)(R$^{52}$)—[CR$^{53}$=CR$^{54}$]z-R$^{55}$ where z is 1 or 2, preferably 1, R$^{51}$ and R$^{52}$ are each independently H or C$_{1-2}$ alkyl, R$^{53}$ and R$^{54}$ are each independently H, halogen, C$_{1-4}$ alkyl or C$_{1-4}$ haloalkyl and R$^{55}$ is phenyl substituted by halogen, C$_{1-4}$ alkyl, C$_{1-4}$ alkoxy, C$_{1-4}$ haloalkyl, C$_{1-4}$ haloalkoxy, CN, NO$_2$, aryl, heteroaryl, amino or dialkylamino or heteroaryl substituted by halogen, C$_{1-4}$ alkyl, C$_{1-4}$ alkoxy, C$_{1-4}$ haloalkyl, C$_{1-4}$ haloalkoxy, CN, NO$_2$, aryl, heteroaryl, amino or dialkylamino or salts or N-oxides thereof.

The compounds in Tables I to XCV below illustrate the compounds of the invention.

Table I provides 1127 compounds of formula Ia

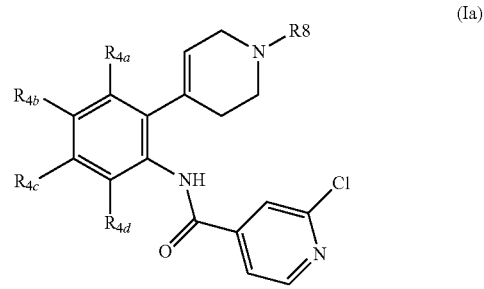

wherein the values of R$^8$, R$^{4a}$, R$^{4b}$, R$^{4c}$ and R$^{4d}$ are given in Table 1.

TABLE 1

| Compound No | R$^8$ | R$^{4a}$ | R$^{4b}$ | R$^{4c}$ | R$^{4d}$ |
|---|---|---|---|---|---|
| I-1 | 4-chlorobenzyl | H | H | H | H |
| I-2 | Cinnamyl | H | H | H | H |
| I-3 | 4-chlorocinnamyl | H | H | H | H |
| I-4 | 4-fluorocinnamyl | H | H | H | H |
| I-5 | 4-bromocinnamyl | H | H | H | H |
| I-6 | 4-trifluoromethylcinnamyl | H | H | H | H |
| I-7 | 4-trifluoromethoxycinnamyl | H | H | H | H |
| I-8 | 4-pentafluoroethoxycinnamyl | H | H | H | H |

TABLE 1-continued

| Compound No | R⁸ | R⁴ᵃ | R⁴ᵇ | R⁴ᶜ | R⁴ᵈ |
|---|---|---|---|---|---|
| I-9 | 4-methoxycinnamyl | H | H | H | H |
| I-10 | 4-ethoxycinnamyl | H | H | H | H |
| I-11 | 4-cyanocinnamyl | H | H | H | H |
| I-12 | 3-(6-chloro-pyridin-3-yl)-allyl | H | H | H | H |
| I-13 | 3-(4-chlorophenyl)-but-2-enyl | H | H | H | H |
| I-14 | 3-(4-chlorophenyl)-3-fluoro-allyl | H | H | H | H |
| I-15 | 3-chloro-4-fluoro-cinnamyl | H | H | H | H |
| I-16 | 3,5-dichloro-cinnamyl | H | H | H | H |
| I-17 | 5-phenyl-penta-2,4-dienyl | H | H | H | H |
| I-18 | 4-isopropyloxycarbonylamino-cinnamyl | H | H | H | H |
| I-19 | 3-naphthalen-2-yl-allyl | H | H | H | H |
| I-20 | 3-(5-trifluoromethyl-pyridin-2-yl)-allyl | H | H | H | H |
| I-21 | 3-(5-chloro-pyridin-2-yl)-allyl | H | H | H | H |
| I-22 | 3-pyridin-4-yl-allyl | H | H | H | H |
| I-23 | 3-(2-Chloro-pyridin-4-yl)-allyl | H | H | H | H |
| I-24 | 4-chlorobenzyl | H | F | H | H |
| I-25 | Cinnamyl | H | F | H | H |
| I-26 | 4-chlorocinnamyl | H | F | H | H |
| I-27 | 4-fluorocinnamyl | H | F | H | H |
| I-28 | 4-bromocinnamyl | H | F | H | H |
| I-29 | 4-trifluoromethylcinnamyl | H | F | H | H |
| I-30 | 4-trifluoromethoxycinnamyl | H | F | H | H |
| I-31 | 4-pentafluoroethoxycinnamyl | H | F | H | H |
| I-32 | 4-methoxycinnamyl | H | F | H | H |
| I-33 | 4-ethoxycinnamyl | H | F | H | H |
| I-34 | 4-cyanocinnamyl | H | F | H | H |
| I-35 | 3-(6-chloro-pyridin-3-yl)-allyl | H | F | H | H |
| I-36 | 3-(4-chlorophenyl)-but-2-enyl | H | F | H | H |
| I-37 | 3-(4-chlorophenyl)-3-fluoro-allyl | H | F | H | H |
| I-38 | 3-chloro-4-fluoro-cinnamyl | H | F | H | H |
| I-39 | 3,5-dichloro-cinnamyl | H | F | H | H |
| I-40 | 5-phenyl-penta-2,4-dienyl | H | F | H | H |
| I-41 | 4-isopropyloxycarbonylamino-cinnamyl | H | F | H | H |
| I-42 | 3-naphthalen-2-yl-allyl | H | F | H | H |
| I-43 | 3-(5-trifluoromethyl-pyridin-2-yl)-allyl | H | F | H | H |
| I-44 | 3-(5-chloro-pyridin-2-yl)-allyl | H | F | H | H |
| I-45 | 3-pyridin-4-yl-allyl | H | F | H | H |
| I-46 | 3-(2-Chloro-pyridin-4-yl)-allyl | H | F | H | H |
| I-47 | 4-chlorobenzyl | H | Cl | H | H |
| I-48 | Cinnamyl | H | Cl | H | H |
| I-49 | 4-chlorocinnamyl | H | Cl | H | H |
| I-50 | 4-fluorocinnamyl | H | Cl | H | H |
| I-51 | 4-bromocinnamyl | H | Cl | H | H |
| I-52 | 4-trifluoromethylcinnamyl | H | Cl | H | H |
| I-53 | 4-trifluoromethoxycinnamyl | H | Cl | H | H |
| I-54 | 4-pentafluoroethoxycinnamyl | H | Cl | H | H |
| I-55 | 4-methoxycinnamyl | H | Cl | H | H |
| I-56 | 4-ethoxycinnamyl | H | Cl | H | H |
| I-57 | 4-cyanocinnamyl | H | Cl | H | H |
| I-58 | 3-(6-chloro-pyridin-3-yl)-allyl | H | Cl | H | H |
| I-59 | 3-(4-chlorophenyl)-but-2-enyl | H | Cl | H | H |
| I-60 | 3-(4-chlorophenyl)-3-fluoro-allyl | H | Cl | H | H |
| I-61 | 3-chloro-4-fluoro-cinnamyl | H | Cl | H | H |
| I-62 | 3,5-dichloro-cinnamyl | H | Cl | H | H |
| I-63 | 5-phenyl-penta-2,4-dienyl | H | Cl | H | H |
| I-64 | 4-isopropyloxycarbonylamino-cinnamyl | H | Cl | H | H |
| I-65 | 3-naphthalen-2-yl-allyl | H | Cl | H | H |
| I-66 | 3-(5-trifluoromethyl-pyridin-2-yl)-allyl | H | Cl | H | H |
| I-67 | 3-(5-chloro-pyridin-2-yl)-allyl | H | Cl | H | H |
| I-68 | 3-pyridin-4-yl-allyl | H | Cl | H | H |
| I-69 | 3-(2-Chloro-pyridin-4-yl)-allyl | H | Cl | H | H |
| I-70 | 4-chlorobenzyl | H | H | F | H |
| I-71 | Cinnamyl | H | H | F | H |
| I-72 | 4-chlorocinnamyl | H | H | F | H |
| I-73 | 4-fluorocinnamyl | H | H | F | H |
| I-74 | 4-bromocinnamyl | H | H | F | H |
| I-75 | 4-trifluoromethylcinnamyl | H | H | F | H |
| I-76 | 4-trifluoromethoxycinnamyl | H | H | F | H |
| I-77 | 4-pentafluoroethoxycinnamyl | H | H | F | H |
| I-78 | 4-methoxycinnamyl | H | H | F | H |

TABLE 1-continued

| Compound No | R⁸ | R⁴ᵃ | R⁴ᵇ | R⁴ᶜ | R⁴ᵈ |
|---|---|---|---|---|---|
| I-79 | 4-ethoxycinnamyl | H | H | F | H |
| I-80 | 4-cyanocinnamyl | H | H | F | H |
| I-81 | 3-(6-chloro-pyridin-3-yl)-allyl | H | H | F | H |
| I-82 | 3-(4-chlorophenyl)-but-2-enyl | H | H | F | H |
| I-83 | 3-(4-chlorophenyl)-3-fluoro-allyl | H | H | F | H |
| I-84 | 3-chloro-4-fluoro-cinnamyl | H | H | F | H |
| I-85 | 3,5-dichloro-cinnamyl | H | H | F | H |
| I-86 | 5-phenyl-penta-2,4-dienyl | H | H | F | H |
| I-87 | 4-isopropyloxycarbonylamino-cinnamyl | H | H | F | H |
| I-88 | 3-naphthalen-2-yl-allyl | H | H | F | H |
| I-89 | 3-(5-trifluoromethyl-pyridin-2-yl)-allyl | H | H | F | H |
| I-90 | 3-(5-chloro-pyridin-2-yl)-allyl | H | H | F | H |
| I-91 | 3-pyridin-4-yl-allyl | H | H | F | H |
| I-92 | 3-(2-Chloro-pyridin-4-yl)-allyl | H | H | F | H |
| I-93 | 4-chlorobenzyl | H | H | Cl | H |
| I-94 | Cinnamyl | H | H | Cl | H |
| I-95 | 4-chlorocinnamyl | H | H | Cl | H |
| I-96 | 4-fluorocinnamyl | H | H | Cl | H |
| I-97 | 4-bromocinnamyl | H | H | Cl | H |
| I-98 | 4-trifluoromethylcinnamyl | H | H | Cl | H |
| I-99 | 4-trifluoromethoxycinnamyl | H | H | Cl | H |
| I-100 | 4-pentafluoroethoxycinnamyl | H | H | Cl | H |
| I-101 | 4-methoxycinnamyl | H | H | Cl | H |
| I-102 | 4-ethoxycinnamyl | H | H | Cl | H |
| I-103 | 4-cyanocinnamyl | H | H | Cl | H |
| I-104 | 3-(6-chloro-pyridin-3-yl)-allyl | H | H | Cl | H |
| I-105 | 3-(4-chlorophenyl)-but-2-enyl | H | H | Cl | H |
| I-106 | 3-(4-chlorophenyl)-3-fluoro-allyl | H | H | Cl | H |
| I-107 | 3-chloro-4-fluoro-cinnamyl | H | H | Cl | H |
| I-108 | 3,5-dichloro-cinnamyl | H | H | Cl | H |
| I-109 | 5-phenyl-penta-2,4-dienyl | H | H | Cl | H |
| I-110 | 4-isopropyloxycarbonylamino-cinnamyl | H | H | Cl | H |
| I-111 | 3-naphthalen-2-yl-allyl | H | H | Cl | H |
| I-112 | 3-(5-trifluoromethyl-pyridin-2-yl)-allyl | H | H | Cl | H |
| I-113 | 3-(5-chloro-pyridin-2-yl)-allyl | H | H | Cl | H |
| I-114 | 3-pyridin-4-yl-allyl | H | H | Cl | H |
| I-115 | 3-(2-Chloro-pyridin-4-yl)-allyl | H | H | Cl | H |
| I-116 | 4-chlorobenzyl | Cl | Cl | H | H |
| I-117 | Cinnamyl | Cl | Cl | H | H |
| I-118 | 4-chlorocinnamyl | Cl | Cl | H | H |
| I-119 | 4-fluorocinnamyl | Cl | Cl | H | H |
| I-120 | 4-bromocinnamyl | Cl | Cl | H | H |
| I-121 | 4-trifluoromethylcinnamyl | Cl | Cl | H | H |
| I-122 | 4-trifluoromethoxycinnamyl | Cl | Cl | H | H |
| I-123 | 4-pentafluoroethoxycinnamyl | Cl | Cl | H | H |
| I-124 | 4-methoxycinnamyl | Cl | Cl | H | H |
| I-125 | 4-ethoxycinnamyl | Cl | Cl | H | H |
| I-126 | 4-cyanocinnamyl | Cl | Cl | H | H |
| I-127 | 3-(6-chloro-pyridin-3-yl)-allyl | Cl | Cl | H | H |
| I-128 | 3-(4-chlorophenyl)-but-2-enyl | Cl | Cl | H | H |
| I-129 | 3-(4-chlorophenyl)-3-fluoro-allyl | Cl | Cl | H | H |
| I-130 | 3-chloro-4-fluoro-cinnamyl | Cl | Cl | H | H |
| I-131 | 3,5-dichloro-cinnamyl | Cl | Cl | H | H |
| I-132 | 5-phenyl-penta-2,4-dienyl | Cl | Cl | H | H |
| I-133 | 4-isopropyloxycarbonylamino-cinnamyl | Cl | Cl | H | H |
| I-134 | 3-naphthalen-2-yl-allyl | Cl | Cl | H | H |
| I-135 | 3-(5-trifluoromethyl-pyridin-2-yl)-allyl | Cl | Cl | H | H |
| I-136 | 3-(5-chloro-pyridin-2-yl)-allyl | Cl | Cl | H | H |
| I-137 | 3-pyridin-4-yl-allyl | Cl | Cl | H | H |
| I-138 | 3-(2-Chloro-pyridin-4-yl)-allyl | Cl | Cl | H | H |
| I-139 | 4-chlorobenzyl | F | F | H | H |
| I-140 | Cinnamyl | F | F | H | H |
| I-141 | 4-chlorocinnamyl | F | F | H | H |
| I-142 | 4-fluorocinnamyl | F | F | H | H |
| I-143 | 4-bromocinnamyl | F | F | H | H |
| I-144 | 4-trifluoromethylcinnamyl | F | F | H | H |
| I-145 | 4-trifluoromethoxycinnamyl | F | F | H | H |
| I-146 | 4-pentafluoroethoxycinnamyl | F | F | H | H |

TABLE 1-continued

| Compound No | R⁸ | R⁴ᵃ | R⁴ᵇ | R⁴ᶜ | R⁴ᵈ |
|---|---|---|---|---|---|
| I-147 | 4-methoxycinnamyl | F | F | H | H |
| I-148 | 4-ethoxycinnamyl | F | F | H | H |
| I-149 | 4-cyanocinnamyl | F | F | H | H |
| I-150 | 3-(6-chloro-pyridin-3-yl)-allyl | F | F | H | H |
| I-151 | 3-(4-chlorophenyl)-but-2-enyl | F | F | H | H |
| I-152 | 3-(4-chlorophenyl)-3-fluoro-allyl | F | F | H | H |
| I-153 | 3-chloro-4-fluoro-cinnamyl | F | F | H | H |
| I-154 | 3,5-dichloro-cinnamyl | F | F | H | H |
| I-155 | 5-phenyl-penta-2,4-dienyl | F | F | H | H |
| I-156 | 4-isopropyloxycarbonylamino-cinnamyl | F | F | H | H |
| I-157 | 3-naphthalen-2-yl-allyl | F | F | H | H |
| I-158 | 3-(5-trifluoromethyl-pyridin-2-yl)-allyl | F | F | H | H |
| I-159 | 3-(5-chloro-pyridin-2-yl)-allyl | F | F | H | H |
| I-160 | 3-pyridin-4-yl-allyl | F | F | H | H |
| I-161 | 3-(2-Chloro-pyridin-4-yl)-allyl | F | F | H | H |
| I-162 | 4-chlorobenzyl | F | H | F | H |
| I-163 | Cinnamyl | F | H | F | H |
| I-164 | 4-chlorocinnamyl | F | H | F | H |
| I-165 | 4-fluorocinnamyl | F | H | F | H |
| I-166 | 4-bromocinnamyl | F | H | F | H |
| I-167 | 4-trifluoromethylcinnamyl | F | H | F | H |
| I-168 | 4-trifluoromethoxycinnamyl | F | H | F | H |
| I-169 | 4-pentafluoroethoxycinnamyl | F | H | F | H |
| I-170 | 4-methoxycinnamyl | F | H | F | H |
| I-171 | 4-ethoxycinnamyl | F | H | F | H |
| I-172 | 4-cyanocinnamyl | F | H | F | H |
| I-173 | 3-(6-chloro-pyridin-3-yl)-allyl | F | H | F | H |
| I-174 | 3-(4-chlorophenyl)-but-2-enyl | F | H | F | H |
| I-175 | 3-(4-chlorophenyl)-3-fluoro-allyl | F | H | F | H |
| I-176 | 3-chloro-4-fluoro-cinnamyl | F | H | F | H |
| I-177 | 3,5-dichloro-cinnamyl | F | H | F | H |
| I-178 | 5-phenyl-penta-2,4-dienyl | F | H | F | H |
| I-179 | 4-isopropyloxycarbonylamino-cinnamyl | F | H | F | H |
| I-180 | 3-naphthalen-2-yl-allyl | F | H | F | H |
| I-181 | 3-(5-trifluoromethyl-pyridin-2-yl)-allyl | F | H | F | H |
| I-182 | 3-(5-chloro-pyridin-2-yl)-allyl | F | H | F | H |
| I-183 | 3-pyridin-4-yl-allyl | F | H | F | H |
| I-184 | 3-(2-Chloro-pyridin-4-yl)-allyl | F | H | F | H |
| I-185 | 4-chlorobenzyl | F | H | H | F |
| I-186 | Cinnamyl | F | H | H | F |
| I-187 | 4-chlorocinnamyl | F | H | H | F |
| I-188 | 4-fluorocinnamyl | F | H | H | F |
| I-189 | 4-bromocinnamyl | F | H | H | F |
| I-190 | 4-trifluoromethylcinnamyl | F | H | H | F |
| I-191 | 4-trifluoromethoxycinnamyl | F | H | H | F |
| I-192 | 4-pentafluoroethoxycinnamyl | F | H | H | F |
| I-193 | 4-methoxycinnamyl | F | H | H | F |
| I-194 | 4-ethoxycinnamyl | F | H | H | F |
| I-195 | 4-cyanocinnamyl | F | H | H | F |
| I-196 | 3-(6-chloro-pyridin-3-yl)-allyl | F | H | H | F |
| I-197 | 3-(4-chlorophenyl)-but-2-enyl | F | H | H | F |
| I-198 | 3-(4-chlorophenyl)-3-fluoro-allyl | F | H | H | F |
| I-199 | 3-chloro-4-fluoro-cinnamyl | F | H | H | F |
| I-200 | 3,5-dichloro-cinnamyl | F | H | H | F |
| I-201 | 5-phenyl-penta-2,4-dienyl | F | H | H | F |
| I-202 | 4-isopropyloxycarbonylamino-cinnamyl | F | H | H | F |
| I-203 | 3-naphthalen-2-yl-allyl | F | H | H | F |
| I-204 | 3-(5-trifluoromethyl-pyridin-2-yl)-allyl | F | H | H | F |
| I-205 | 3-(5-chloro-pyridin-2-yl)-allyl | F | H | H | F |
| I-206 | 3-pyridin-4-yl-allyl | F | H | H | F |
| I-207 | 3-(2-Chloro-pyridin-4-yl)-allyl | F | H | H | F |
| I-208 | 4-chlorobenzyl | Cl | H | Cl | H |
| I-209 | Cinnamyl | Cl | H | Cl | H |
| I-210 | 4-chlorocinnamyl | Cl | H | Cl | H |
| I-211 | 4-fluorocinnamyl | Cl | H | Cl | H |
| I-212 | 4-bromocinnamyl | Cl | H | Cl | H |
| I-213 | 4-trifluoromethylcinnamyl | Cl | H | Cl | H |
| I-214 | 4-trifluoromethoxycinnamyl | Cl | H | Cl | H |

TABLE 1-continued

| Compound No | $R^8$ | $R^{4a}$ | $R^{4b}$ | $R^{4c}$ | $R^{4d}$ |
|---|---|---|---|---|---|
| I-215 | 4-pentafluoroethoxycinnamyl | Cl | H | Cl | H |
| I-216 | 4-methoxycinnamyl | Cl | H | Cl | H |
| I-217 | 4-ethoxycinnamyl | Cl | H | Cl | H |
| I-218 | 4-cyanocinnamyl | Cl | H | Cl | H |
| I-219 | 3-(6-chloro-pyridin-3-yl)-allyl | Cl | H | Cl | H |
| I-220 | 3-(4-chlorophenyl)-but-2-enyl | Cl | H | Cl | H |
| I-221 | 3-(4-chlorophenyl)-3-fluoro-allyl | Cl | H | Cl | H |
| I-222 | 3-chloro-4-fluoro-cinnamyl | Cl | H | Cl | H |
| I-223 | 3,5-dichloro-cinnamyl | Cl | H | Cl | H |
| I-224 | 5-phenyl-penta-2,4-dienyl | Cl | H | Cl | H |
| I-225 | 4-isopropyloxycarbonylamino-cinnamyl | Cl | H | Cl | H |
| I-226 | 3-naphthalen-2-yl-allyl | Cl | H | Cl | H |
| I-227 | 3-(5-trifluoromethyl-pyridin-2-yl)-allyl | Cl | H | Cl | H |
| I-228 | 3-(5-chloro-pyridin-2-yl)-allyl | Cl | H | Cl | H |
| I-229 | 3-pyridin-4-yl-allyl | Cl | H | Cl | H |
| I-230 | 3-(2-Chloro-pyridin-4-yl)-allyl | Cl | H | Cl | H |
| I-231 | 4-chlorobenzyl | Cl | H | H | Cl |
| I-232 | Cinnamyl | Cl | H | H | Cl |
| I-233 | 4-chlorocinnamyl | Cl | H | H | Cl |
| I-234 | 4-fluorocinnamyl | Cl | H | H | Cl |
| I-235 | 4-bromocinnamyl | Cl | H | H | Cl |
| I-236 | 4-trifluoromethylcinnamyl | Cl | H | H | Cl |
| I-237 | 4-trifluoromethoxycinnamyl | Cl | H | H | Cl |
| I-238 | 4-pentafluoroethoxycinnamyl | Cl | H | H | Cl |
| I-239 | 4-methoxycinnamyl | Cl | H | H | Cl |
| I-240 | 4-ethoxycinnamyl | Cl | H | H | Cl |
| I-241 | 4-cyanocinnamyl | Cl | H | H | Cl |
| I-242 | 3-(6-chloro-pyridin-3-yl)-allyl | Cl | H | H | Cl |
| I-243 | 3-(4-chlorophenyl)-but-2-enyl | Cl | H | H | Cl |
| I-244 | 3-(4-chlorophenyl)-3-fluoro-allyl | Cl | H | H | Cl |
| I-245 | 3-chloro-4-fluoro-cinnamyl | Cl | H | H | Cl |
| I-246 | 3,5-dichloro-cinnamyl | Cl | H | H | Cl |
| I-247 | 5-phenyl-penta-2,4-dienyl | Cl | H | H | Cl |
| I-248 | 4-isopropyloxycarbonylamino-cinnamyl | Cl | H | H | Cl |
| I-249 | 3-naphthalen-2-yl-allyl | Cl | H | H | Cl |
| I-250 | 3-(5-trifluoromethyl-pyridin-2-yl)-allyl | Cl | H | H | Cl |
| I-251 | 3-(5-chloro-pyridin-2-yl)-allyl | Cl | H | H | Cl |
| I-252 | 3-pyridin-4-yl-allyl | Cl | H | H | Cl |
| I-253 | 3-(2-Chloro-pyridin-4-yl)-allyl | Cl | H | H | Cl |
| I-254 | 4-chlorobenzyl | F | Cl | H | H |
| I-255 | Cinnamyl | F | Cl | H | H |
| I-256 | 4-chlorocinnamyl | F | Cl | H | H |
| I-257 | 4-fluorocinnamyl | F | Cl | H | H |
| I-258 | 4-bromocinnamyl | F | Cl | H | H |
| I-259 | 4-trifluoromethylcinnamyl | F | Cl | H | H |
| I-260 | 4-trifluoromethoxycinnamyl | F | Cl | H | H |
| I-261 | 4-pentafluoroethoxycinnamyl | F | Cl | H | H |
| I-262 | 4-methoxycinnamyl | F | Cl | H | H |
| I-263 | 4-ethoxycinnamyl | F | Cl | H | H |
| I-264 | 4-cyanocinnamyl | F | Cl | H | H |
| I-265 | 3-(6-chloro-pyridin-3-yl)-allyl | F | Cl | H | H |
| I-266 | 3-(4-chlorophenyl)-but-2-enyl | F | Cl | H | H |
| I-267 | 3-(4-chlorophenyl)-3-fluoro-allyl | F | Cl | H | H |
| I-268 | 3-chloro-4-fluoro-cinnamyl | F | Cl | H | H |
| I-269 | 3,5-dichloro-cinnamyl | F | Cl | H | H |
| I-270 | 5-phenyl-penta-2,4-dienyl | F | Cl | H | H |
| I-271 | 4-isopropyloxycarbonylamino-cinnamyl | F | Cl | H | H |
| I-272 | 3-naphthalen-2-yl-allyl | F | Cl | H | H |
| I-273 | 3-(5-trifluoromethyl-pyridin-2-yl)-allyl | F | Cl | H | H |
| I-274 | 3-(5-chloro-pyridin-2-yl)-allyl | F | Cl | H | H |
| I-275 | 3-pyridin-4-yl-allyl | F | Cl | H | H |
| I-276 | 3-(2-Chloro-pyridin-4-yl)-allyl | F | Cl | H | H |
| I-277 | 4-chlorobenzyl | F | H | Cl | H |
| I-278 | Cinnamyl | F | H | Cl | H |
| I-279 | 4-chlorocinnamyl | F | H | Cl | H |
| I-280 | 4-fluorocinnamyl | F | H | Cl | H |
| I-281 | 4-bromocinnamyl | F | H | Cl | H |
| I-282 | 4-trifluoromethylcinnamyl | F | H | Cl | H |

TABLE 1-continued

| Compound No | R⁸ | R⁴ᵃ | R⁴ᵇ | R⁴ᶜ | R⁴ᵈ |
|---|---|---|---|---|---|
| I-283 | 4-trifluoromethoxycinnamyl | F | H | Cl | H |
| I-284 | 4-pentafluoroethoxycinnamyl | F | H | Cl | H |
| I-285 | 4-methoxycinnamyl | F | H | Cl | H |
| I-286 | 4-ethoxycinnamyl | F | H | Cl | H |
| I-287 | 4-cyanocinnamyl | F | H | Cl | H |
| I-288 | 3-(6-chloro-pyridin-3-yl)-allyl | F | H | Cl | H |
| I-289 | 3-(4-chlorophenyl)-but-2-enyl | F | H | Cl | H |
| I-290 | 3-(4-chlorophenyl)-3-fluoro-allyl | F | H | Cl | H |
| I-291 | 3-chloro-4-fluoro-cinnamyl | F | H | Cl | H |
| I-292 | 3,5-dichloro-cinnamyl | F | H | Cl | H |
| I-293 | 5-phenyl-penta-2,4-dienyl | F | H | Cl | H |
| I-294 | 4-isopropyloxycarbonylamino-cinnamyl | F | H | Cl | H |
| I-295 | 3-naphthalen-2-yl-allyl | F | H | Cl | H |
| I-296 | 3-(5-trifluoromethyl-pyridin-2-yl)-allyl | F | H | Cl | H |
| I-297 | 3-(5-chloro-pyridin-2-yl)-allyl | F | H | Cl | H |
| I-298 | 3-pyridin-4-yl-allyl | F | H | Cl | H |
| I-299 | 3-(2-Chloro-pyridin-4-yl)-allyl | F | H | Cl | H |
| I-300 | 4-chlorobenzyl | F | H | H | Cl |
| I-301 | Cinnamyl | F | H | H | Cl |
| I-302 | 4-chlorocinnamyl | F | H | H | Cl |
| I-303 | 4-fluorocinnamyl | F | H | H | Cl |
| I-304 | 4-bromocinnamyl | F | H | H | Cl |
| I-305 | 4-trifluoromethylcinnamyl | F | H | H | Cl |
| I-306 | 4-trifluoromethoxycinnamyl | F | H | H | Cl |
| I-307 | 4-pentafluoroethoxycinnamyl | F | H | H | Cl |
| I-308 | 4-methoxycinnamyl | F | H | H | Cl |
| I-309 | 4-ethoxycinnamyl | F | H | H | Cl |
| I-310 | 4-cyanocinnamyl | F | H | H | Cl |
| I-311 | 3-(6-chloro-pyridin-3-yl)-allyl | F | H | H | Cl |
| I-312 | 3-(4-chlorophenyl)-but-2-enyl | F | H | H | Cl |
| I-313 | 3-(4-chlorophenyl)-3-fluoro-allyl | F | H | H | Cl |
| I-314 | 3-chloro-4-fluoro-cinnamyl | F | H | H | Cl |
| I-315 | 3,5-dichloro-cinnamyl | F | H | H | Cl |
| I-316 | 5-phenyl-penta-2,4-dienyl | F | H | H | Cl |
| I-317 | 4-isopropyloxycarbonylamino-cinnamyl | F | H | H | Cl |
| I-318 | 3-naphthalen-2-yl-allyl | F | H | H | Cl |
| I-319 | 3-(5-trifluoromethyl-pyridin-2-yl)-allyl | F | H | H | Cl |
| I-320 | 3-(5-chloro-pyridin-2-yl)-allyl | F | H | H | Cl |
| I-321 | 3-pyridin-4-yl-allyl | F | H | H | Cl |
| I-322 | 3-(2-Chloro-pyridin-4-yl)-allyl | F | H | H | Cl |
| I-323 | 4-chlorobenzyl | Cl | F | H | H |
| I-324 | Cinnamyl | Cl | F | H | H |
| I-325 | 4-chlorocinnamyl | Cl | F | H | H |
| I-326 | 4-fluorocinnamyl | Cl | F | H | H |
| I-327 | 4-bromocinnamyl | Cl | F | H | H |
| I-328 | 4-trifluoromethylcinnamyl | Cl | F | H | H |
| I-329 | 4-trifluoromethoxycinnamyl | Cl | F | H | H |
| I-330 | 4-pentafluoroethoxycinnamyl | Cl | F | H | H |
| I-331 | 4-methoxycinnamyl | Cl | F | H | H |
| I-332 | 4-ethoxycinnamyl | Cl | F | H | H |
| I-333 | 4-cyanocinnamyl | Cl | F | H | H |
| I-334 | 3-(6-chloro-pyridin-3-yl)-allyl | Cl | F | H | H |
| I-335 | 3-(4-chlorophenyl)-but-2-enyl | Cl | F | H | H |
| I-336 | 3-(4-chlorophenyl)-3-fluoro-allyl | Cl | F | H | H |
| I-337 | 3-chloro-4-fluoro-cinnamyl | Cl | F | H | H |
| I-338 | 3,5-dichloro-cinnamyl | Cl | F | H | H |
| I-339 | 5-phenyl-penta-2,4-dienyl | Cl | F | H | H |
| I-340 | 4-isopropyloxycarbonylamino-cinnamyl | Cl | F | H | H |
| I-341 | 3-naphthalen-2-yl-allyl | Cl | F | H | H |
| I-342 | 3-(5-trifluoromethyl-pyridin-2-yl)-allyl | Cl | F | H | H |
| I-343 | 3-(5-chloro-pyridin-2-yl)-allyl | Cl | F | H | H |
| I-344 | 3-pyridin-4-yl-allyl | Cl | F | H | H |
| I-345 | 3-(2-Chloro-pyridin-4-yl)-allyl | Cl | F | H | H |
| I-346 | 4-chlorobenzyl | H | F | Cl | H |
| I-347 | Cinnamyl | H | F | Cl | H |
| I-348 | 4-chlorocinnamyl | H | F | Cl | H |
| I-349 | 4-fluorocinnamyl | H | F | Cl | H |
| I-350 | 4-bromocinnamyl | H | F | Cl | H |

TABLE 1-continued

| Compound No | R⁸ | R⁴ᵃ | R⁴ᵇ | R⁴ᶜ | R⁴ᵈ |
|---|---|---|---|---|---|
| I-351 | 4-trifluoromethylcinnamyl | H | F | Cl | H |
| I-352 | 4-trifluoromethoxycinnamyl | H | F | Cl | H |
| I-353 | 4-pentafluoroethoxycinnamyl | H | F | Cl | H |
| I-354 | 4-methoxycinnamyl | H | F | Cl | H |
| I-355 | 4-ethoxycinnamyl | H | F | Cl | H |
| I-356 | 4-cyanocinnamyl | H | F | Cl | H |
| I-357 | 3-(6-chloro-pyridin-3-yl)-allyl | H | F | Cl | H |
| I-358 | 3-(4-chlorophenyl)-but-2-enyl | H | F | Cl | H |
| I-359 | 3-(4-chlorophenyl)-3-fluoro-allyl | H | F | Cl | H |
| I-360 | 3-chloro-4-fluoro-cinnamyl | H | F | Cl | H |
| I-361 | 3,5-dichloro-cinnamyl | H | F | Cl | H |
| I-362 | 5-phenyl-penta-2,4-dienyl | H | F | Cl | H |
| I-363 | 4-isopropyloxycarbonylamino-cinnamyl | H | F | Cl | H |
| I-364 | 3-naphthalen-2-yl-allyl | H | F | Cl | H |
| I-365 | 3-(5-trifluoromethyl-pyridin-2-yl)-allyl | H | F | Cl | H |
| I-366 | 3-(5-chloro-pyridin-2-yl)-allyl | H | F | Cl | H |
| I-367 | 3-pyridin-4-yl-allyl | H | F | Cl | H |
| I-368 | 3-(2-Chloro-pyridin-4-yl)-allyl | H | F | Cl | H |
| I-369 | 4-chlorobenzyl | H | F | H | Cl |
| I-370 | Cinnamyl | H | F | H | Cl |
| I-371 | 4-chlorocinnamyl | H | F | H | Cl |
| I-372 | 4-fluorocinnamyl | H | F | H | Cl |
| I-373 | 4-bromocinnamyl | H | F | H | Cl |
| I-374 | 4-trifluoromethylcinnamyl | H | F | H | Cl |
| I-375 | 4-trifluoromethoxycinnamyl | H | F | H | Cl |
| I-376 | 4-pentafluoroethoxycinnamyl | H | F | H | Cl |
| I-377 | 4-methoxycinnamyl | H | F | H | Cl |
| I-378 | 4-ethoxycinnamyl | H | F | H | Cl |
| I-379 | 4-cyanocinnamyl | H | F | H | Cl |
| I-380 | 3-(6-chloro-pyridin-3-yl)-allyl | H | F | H | Cl |
| I-381 | 3-(4-chlorophenyl)-but-2-enyl | H | F | H | Cl |
| I-382 | 3-(4-chlorophenyl)-3-fluoro-allyl | H | F | H | Cl |
| I-383 | 3-chloro-4-fluoro-cinnamyl | H | F | H | Cl |
| I-384 | 3,5-dichloro-cinnamyl | H | F | H | Cl |
| I-385 | 5-phenyl-penta-2,4-dienyl | H | F | H | Cl |
| I-386 | 4-isopropyloxycarbonylamino-cinnamyl | H | F | H | Cl |
| I-387 | 3-naphthalen-2-yl-allyl | H | F | H | Cl |
| I-388 | 3-(5-trifluoromethyl-pyridin-2-yl)-allyl | H | F | H | Cl |
| I-389 | 3-(5-chloro-pyridin-2-yl)-allyl | H | F | H | Cl |
| I-390 | 3-pyridin-4-yl-allyl | H | F | H | Cl |
| I-391 | 3-(2-Chloro-pyridin-4-yl)-allyl | H | F | H | Cl |
| I-392 | 4-chlorobenzyl | Cl | H | F | H |
| I-393 | Cinnamyl | Cl | H | F | H |
| I-394 | 4-chlorocinnamyl | Cl | H | F | H |
| I-395 | 4-fluorocinnamyl | Cl | H | F | H |
| I-396 | 4-bromocinnamyl | Cl | H | F | H |
| I-397 | 4-trifluoromethylcinnamyl | Cl | H | F | H |
| I-398 | 4-trifluoromethoxycinnamyl | Cl | H | F | H |
| I-399 | 4-pentafluoroethoxycinnamyl | Cl | H | F | H |
| I-400 | 4-methoxycinnamyl | Cl | H | F | H |
| I-401 | 4-ethoxycinnamyl | Cl | H | F | H |
| I-402 | 4-cyanocinnamyl | Cl | H | F | H |
| I-403 | 3-(6-chloro-pyridin-3-yl)-allyl | Cl | H | F | H |
| I-404 | 3-(4-chlorophenyl)-but-2-enyl | Cl | H | F | H |
| I-405 | 3-(4-chlorophenyl)-3-fluoro-allyl | Cl | H | F | H |
| I-406 | 3-chloro-4-fluoro-cinnamyl | Cl | H | F | H |
| I-407 | 3,5-dichloro-cinnamyl | Cl | H | F | H |
| I-408 | 5-phenyl-penta-2,4-dienyl | Cl | H | F | H |
| I-409 | 4-isopropyloxycarbonylamino-cinnamyl | Cl | H | F | H |
| I-410 | 3-naphthalen-2-yl-allyl | Cl | H | F | H |
| I-411 | 3-(5-trifluoromethyl-pyridin-2-yl)-allyl | Cl | H | F | H |
| I-412 | 3-(5-chloro-pyridin-2-yl)-allyl | Cl | H | F | H |
| I-413 | 3-pyridin-4-yl-allyl | Cl | H | F | H |
| I-414 | 3-(2-Chloro-pyridin-4-yl)-allyl | Cl | H | F | H |
| I-415 | 4-chlorobenzyl | H | Cl | F | H |
| I-416 | Cinnamyl | H | Cl | F | H |
| I-417 | 4-chlorocinnamyl | H | Cl | F | H |
| I-418 | 4-fluorocinnamyl | H | Cl | F | H |

TABLE 1-continued

| Compound No | R⁸ | R⁴ᵃ | R⁴ᵇ | R⁴ᶜ | R⁴ᵈ |
|---|---|---|---|---|---|
| I-419 | 4-bromocinnamyl | H | Cl | F | H |
| I-420 | 4-trifluoromethylcinnamyl | H | Cl | F | H |
| I-421 | 4-trifluoromethoxycinnamyl | H | Cl | F | H |
| I-422 | 4-pentafluoroethoxycinnamyl | H | Cl | F | H |
| I-423 | 4-methoxycinnamyl | H | Cl | F | H |
| I-424 | 4-ethoxycinnamyl | H | Cl | F | H |
| I-425 | 4-cyanocinnamyl | H | Cl | F | H |
| I-426 | 3-(6-chloro-pyridin-3-yl)-allyl | H | Cl | F | H |
| I-427 | 3-(4-chlorophenyl)-but-2-enyl | H | Cl | F | H |
| I-428 | 3-(4-chlorophenyl)-3-fluoro-allyl | H | Cl | F | H |
| I-429 | 3-chloro-4-fluoro-cinnamyl | H | Cl | F | H |
| I-430 | 3,5-dichloro-cinnamyl | H | Cl | F | H |
| I-431 | 5-phenyl-penta-2,4-dienyl | H | Cl | F | H |
| I-432 | 4-isopropyloxycarbonylamino-cinnamyl | H | Cl | F | H |
| I-433 | 3-naphthalen-2-yl-allyl | H | Cl | F | H |
| I-434 | 3-(5-trifluoromethyl-pyridin-2-yl)-allyl | H | Cl | F | H |
| I-435 | 3-(5-chloro-pyridin-2-yl)-allyl | H | Cl | F | H |
| I-436 | 3-pyridin-4-yl-allyl | H | Cl | F | H |
| I-437 | 3-(2-Chloro-pyridin-4-yl)-allyl | H | Cl | F | H |
| I-438 | 4-chlorobenzyl | H | H | F | Cl |
| I-439 | Cinnamyl | H | H | F | Cl |
| I-440 | 4-chlorocinnamyl | H | H | F | Cl |
| I-441 | 4-fluorocinnamyl | H | H | F | Cl |
| I-442 | 4-bromocinnamyl | H | H | F | Cl |
| I-443 | 4-trifluoromethylcinnamyl | H | H | F | Cl |
| I-444 | 4-trifluoromethoxycinnamyl | H | H | F | Cl |
| I-445 | 4-pentafluoroethoxycinnamyl | H | H | F | Cl |
| I-446 | 4-methoxycinnamyl | H | H | F | Cl |
| I-447 | 4-ethoxycinnamyl | H | H | F | Cl |
| I-448 | 4-cyanocinnamyl | H | H | F | Cl |
| I-449 | 3-(6-chloro-pyridin-3-yl)-allyl | H | H | F | Cl |
| I-450 | 3-(4-chlorophenyl)-but-2-enyl | H | H | F | Cl |
| I-451 | 3-(4-chlorophenyl)-3-fluoro-allyl | H | H | F | Cl |
| I-452 | 3-chloro-4-fluoro-cinnamyl | H | H | F | Cl |
| I-453 | 3,5-dichloro-cinnamyl | H | H | F | Cl |
| I-454 | 5-phenyl-penta-2,4-dienyl | H | H | F | Cl |
| I-455 | 4-isopropyloxycarbonylamino-cinnamyl | H | H | F | Cl |
| I-456 | 3-naphthalen-2-yl-allyl | H | H | F | Cl |
| I-457 | 3-(5-trifluoromethyl-pyridin-2-yl)-allyl | H | H | F | Cl |
| I-458 | 3-(5-chloro-pyridin-2-yl)-allyl | H | H | F | Cl |
| I-459 | 3-pyridin-4-yl-allyl | H | H | F | Cl |
| I-460 | 3-(2-Chloro-pyridin-4-yl)-allyl | H | H | F | Cl |
| I-461 | 4-chlorobenzyl | Cl | H | H | F |
| I-462 | Cinnamyl | Cl | H | H | F |
| I-463 | 4-chlorocinnamyl | Cl | H | H | F |
| I-464 | 4-fluorocinnamyl | Cl | H | H | F |
| I-465 | 4-bromocinnamyl | Cl | H | H | F |
| I-466 | 4-trifluoromethylcinnamyl | Cl | H | H | F |
| I-467 | 4-trifluoromethoxycinnamyl | Cl | H | H | F |
| I-468 | 4-pentafluoroethoxycinnamyl | Cl | H | H | F |
| I-469 | 4-methoxycinnamyl | Cl | H | H | F |
| I-470 | 4-ethoxycinnamyl | Cl | H | H | F |
| I-471 | 4-cyanocinnamyl | Cl | H | H | F |
| I-472 | 3-(6-chloro-pyridin-3-yl)-allyl | Cl | H | H | F |
| I-473 | 3-(4-chlorophenyl)-but-2-enyl | Cl | H | H | F |
| I-474 | 3-(4-chlorophenyl)-3-fluoro-allyl | Cl | H | H | F |
| I-475 | 3-chloro-4-fluoro-cinnamyl | Cl | H | H | F |
| I-476 | 3,5-dichloro-cinnamyl | Cl | H | H | F |
| I-477 | 5-phenyl-penta-2,4-dienyl | Cl | H | H | F |
| I-478 | 4-isopropyloxycarbonylamino-cinnamyl | Cl | H | H | F |
| I-479 | 3-naphthalen-2-yl-allyl | Cl | H | H | F |
| I-480 | 3-(5-trifluoromethyl-pyridin-2-yl)-allyl | Cl | H | H | F |
| I-481 | 3-(5-chloro-pyridin-2-yl)-allyl | Cl | H | H | F |
| I-482 | 3-pyridin-4-yl-allyl | Cl | H | H | F |
| I-483 | 3-(2-Chloro-pyridin-4-yl)-allyl | Cl | H | H | F |
| I-484 | 4-chlorobenzyl | H | Cl | H | F |
| I-485 | Cinnamyl | H | Cl | H | F |
| I-486 | 4-chlorocinnamyl | H | Cl | H | F |

TABLE 1-continued

| Compound No | R⁸ | R⁴ᵃ | R⁴ᵇ | R⁴ᶜ | R⁴ᵈ |
|---|---|---|---|---|---|
| I-487 | 4-fluorocinnamyl | H | Cl | H | F |
| I-488 | 4-bromocinnamyl | H | Cl | H | F |
| I-489 | 4-trifluoromethylcinnamyl | H | Cl | H | F |
| I-490 | 4-trifluoromethoxycinnamyl | H | Cl | H | F |
| I-491 | 4-pentafluoroethoxycinnamyl | H | Cl | H | F |
| I-492 | 4-methoxycinnamyl | H | Cl | H | F |
| I-493 | 4-ethoxycinnamyl | H | Cl | H | F |
| I-494 | 4-cyanocinnamyl | H | Cl | H | F |
| I-495 | 3-(6-chloro-pyridin-3-yl)-allyl | H | Cl | H | F |
| I-496 | 3-(4-chlorophenyl)-but-2-enyl | H | Cl | H | F |
| I-497 | 3-(4-chlorophenyl)-3-fluoro-allyl | H | Cl | H | F |
| I-498 | 3-chloro-4-fluoro-cinnamyl | H | Cl | H | F |
| I-499 | 3,5-dichloro-cinnamyl | H | Cl | H | F |
| I-500 | 5-phenyl-penta-2,4-dienyl | H | Cl | H | F |
| I-501 | 4-isopropyloxycarbonylamino-cinnamyl | H | Cl | H | F |
| I-502 | 3-naphthalen-2-yl-allyl | H | Cl | H | F |
| I-503 | 3-(5-trifluoromethyl-pyridin-2-yl)-allyl | H | Cl | H | F |
| I-504 | 3-(5-chloro-pyridin-2-yl)-allyl | H | Cl | H | F |
| I-505 | 3-pyridin-4-yl-allyl | H | Cl | H | F |
| I-506 | 3-(2-Chloro-pyridin-4-yl)-allyl | H | Cl | H | F |
| I-507 | 4-chlorobenzyl | H | H | Cl | F |
| I-508 | Cinnamyl | H | H | Cl | F |
| I-509 | 4-chlorocinnamyl | H | H | Cl | F |
| I-510 | 4-fluorocinnamyl | H | H | Cl | F |
| I-511 | 4-bromocinnamyl | H | H | Cl | F |
| I-512 | 4-trifluoromethylcinnamyl | H | H | Cl | F |
| I-513 | 4-trifluoromethoxycinnamyl | H | H | Cl | F |
| I-514 | 4-pentafluoroethoxycinnamyl | H | H | Cl | F |
| I-515 | 4-methoxycinnamyl | H | H | Cl | F |
| I-516 | 4-ethoxycinnamyl | H | H | Cl | F |
| I-517 | 4-cyanocinnamyl | H | H | Cl | F |
| I-518 | 3-(6-chloro-pyridin-3-yl)-allyl | H | H | Cl | F |
| I-519 | 3-(4-chlorophenyl)-but-2-enyl | H | H | Cl | F |
| I-520 | 3-(4-chlorophenyl)-3-fluoro-allyl | H | H | Cl | F |
| I-521 | 3-chloro-4-fluoro-cinnamyl | H | H | Cl | F |
| I-522 | 3,5-dichloro-cinnamyl | H | H | Cl | F |
| I-523 | 5-phenyl-penta-2,4-dienyl | H | H | Cl | F |
| I-524 | 4-isopropyloxycarbonylamino-cinnamyl | H | H | Cl | F |
| I-525 | 3-naphthalen-2-yl-allyl | H | H | Cl | F |
| I-526 | 3-(5-trifluoromethyl-pyridin-2-yl)-allyl | H | H | Cl | F |
| I-527 | 3-(5-chloro-pyridin-2-yl)-allyl | H | H | Cl | F |
| I-528 | 3-pyridin-4-yl-allyl | H | H | Cl | F |
| I-529 | 3-(2-Chloro-pyridin-4-yl)-allyl | H | H | Cl | F |
| I-530 | 4-chlorobenzyl | H | F | F | F |
| I-531 | Cinnamyl | H | F | F | F |
| I-532 | 4-chlorocinnamyl | H | F | F | F |
| I-533 | 4-fluorocinnamyl | H | F | F | F |
| I-534 | 4-bromocinnamyl | H | F | F | F |
| I-535 | 4-trifluoromethylcinnamyl | H | F | F | F |
| I-536 | 4-trifluoromethoxycinnamyl | H | F | F | F |
| I-537 | 4-pentafluoroethoxycinnamyl | H | F | F | F |
| I-538 | 4-methoxycinnamyl | H | F | F | F |
| I-539 | 4-ethoxycinnamyl | H | F | F | F |
| I-540 | 4-cyanocinnamyl | H | F | F | F |
| I-541 | 3-(6-chloro-pyridin-3-yl)-allyl | H | F | F | F |
| I-542 | 3-(4-chlorophenyl)-but-2-enyl | H | F | F | F |
| I-543 | 3-(4-chlorophenyl)-3-fluoro-allyl | H | F | F | F |
| I-544 | 3-chloro-4-fluoro-cinnamyl | H | F | F | F |
| I-545 | 3,5-dichloro-cinnamyl | H | F | F | F |
| I-546 | 5-phenyl-penta-2,4-dienyl | H | F | F | F |
| I-547 | 4-isopropyloxycarbonylamino-cinnamyl | H | F | F | F |
| I-548 | 3-naphthalen-2-yl-allyl | H | F | F | F |
| I-549 | 3-(5-trifluoromethyl-pyridin-2-yl)-allyl | H | F | F | F |
| I-550 | 3-(5-chloro-pyridin-2-yl)-allyl | H | F | F | F |
| I-551 | 3-pyridin-4-yl-allyl | H | F | F | F |
| I-552 | 3-(2-Chloro-pyridin-4-yl)-allyl | H | F | F | F |
| I-553 | 4-chlorobenzyl | F | H | F | F |
| I-554 | Cinnamyl | F | H | F | F |

TABLE 1-continued

| Compound No | R⁸ | R⁴ᵃ | R⁴ᵇ | R⁴ᶜ | R⁴ᵈ |
|---|---|---|---|---|---|
| I-555 | 4-chlorocinnamyl | F | H | F | F |
| I-556 | 4-fluorocinnamyl | F | H | F | F |
| I-557 | 4-bromocinnamyl | F | H | F | F |
| I-558 | 4-trifluoromethylcinnamyl | F | H | F | F |
| I-559 | 4-trifluoromethoxycinnamyl | F | H | F | F |
| I-560 | 4-pentafluoroethoxycinnamyl | F | H | F | F |
| I-561 | 4-methoxycinnamyl | F | H | F | F |
| I-562 | 4-ethoxycinnamyl | F | H | F | F |
| I-563 | 4-cyanocinnamyl | F | H | F | F |
| I-564 | 3-(6-chloro-pyridin-3-yl)-allyl | F | H | F | F |
| I-565 | 3-(4-chlorophenyl)-but-2-enyl | F | H | F | F |
| I-566 | 3-(4-chlorophenyl)-3-fluoro-allyl | F | H | F | F |
| I-567 | 3-chloro-4-fluoro-cinnamyl | F | H | F | F |
| I-568 | 3,5-dichloro-cinnamyl | F | H | F | F |
| I-569 | 5-phenyl-penta-2,4-dienyl | F | H | F | F |
| I-570 | 4-isopropyloxycarbonylamino-cinnamyl | F | H | F | F |
| I-571 | 3-naphthalen-2-yl-allyl | F | H | F | F |
| I-572 | 3-(5-trifluoromethyl-pyridin-2-yl)-allyl | F | H | F | F |
| I-573 | 3-(5-chloro-pyridin-2-yl)-allyl | F | H | F | F |
| I-574 | 3-pyridin-4-yl-allyl | F | H | F | F |
| I-575 | 3-(2-Chloro-pyridin-4-yl)-allyl | F | H | F | F |
| I-576 | 4-chlorobenzyl | F | F | H | F |
| I-577 | Cinnamyl | F | F | H | F |
| I-578 | 4-chlorocinnamyl | F | F | H | F |
| I-579 | 4-fluorocinnamyl | F | F | H | F |
| I-580 | 4-bromocinnamyl | F | F | H | F |
| I-581 | 4-trifluoromethylcinnamyl | F | F | H | F |
| I-582 | 4-trifluoromethoxycinnamyl | F | F | H | F |
| I-583 | 4-pentafluoroethoxycinnamyl | F | F | H | F |
| I-584 | 4-methoxycinnamyl | F | F | H | F |
| I-585 | 4-ethoxycinnamyl | F | F | H | F |
| I-586 | 4-cyanocinnamyl | F | F | H | F |
| I-587 | 3-(6-chloro-pyridin-3-yl)-allyl | F | F | H | F |
| I-588 | 3-(4-chlorophenyl)-but-2-enyl | F | F | H | F |
| I-589 | 3-(4-chlorophenyl)-3-fluoro-allyl | F | F | H | F |
| I-590 | 3-chloro-4-fluoro-cinnamyl | F | F | H | F |
| I-591 | 3,5-dichloro-cinnamyl | F | F | H | F |
| I-592 | 5-phenyl-penta-2,4-dienyl | F | F | H | F |
| I-593 | 4-isopropyloxycarbonylamino-cinnamyl | F | F | H | F |
| I-594 | 3-naphthalen-2-yl-allyl | F | F | H | F |
| I-595 | 3-(5-trifluoromethyl-pyridin-2-yl)-allyl | F | F | H | F |
| I-596 | 3-(5-chloro-pyridin-2-yl)-allyl | F | F | H | F |
| I-597 | 3-pyridin-4-yl-allyl | F | F | H | F |
| I-598 | 3-(2-Chloro-pyridin-4-yl)-allyl | F | F | H | F |
| I-599 | 4-chlorobenzyl | F | F | F | H |
| I-600 | Cinnamyl | F | F | F | H |
| I-601 | 4-chlorocinnamyl | F | F | F | H |
| I-602 | 4-fluorocinnamyl | F | F | F | H |
| I-603 | 4-bromocinnamyl | F | F | F | H |
| I-604 | 4-trifluoromethylcinnamyl | F | F | F | H |
| I-605 | 4-trifluoromethoxycinnamyl | F | F | F | H |
| I-606 | 4-pentafluoroethoxycinnamyl | F | F | F | H |
| I-607 | 4-methoxycinnamyl | F | F | F | H |
| I-608 | 4-ethoxycinnamyl | F | F | F | H |
| I-609 | 4-cyanocinnamyl | F | F | F | H |
| I-610 | 3-(6-chloro-pyridin-3-yl)-allyl | F | F | F | H |
| I-611 | 3-(4-chlorophenyl)-but-2-enyl | F | F | F | H |
| I-612 | 3-(4-chlorophenyl)-3-fluoro-allyl | F | F | F | H |
| I-613 | 3-chloro-4-fluoro-cinnamyl | F | F | F | H |
| I-614 | 3,5-dichloro-cinnamyl | F | F | F | H |
| I-615 | 5-phenyl-penta-2,4-dienyl | F | F | F | H |
| I-616 | 4-isopropyloxycarbonylamino-cinnamyl | F | F | F | H |
| I-617 | 3-naphthalen-2-yl-allyl | F | F | F | H |
| I-618 | 3-(5-trifluoromethyl-pyridin-2-yl)-allyl | F | F | F | H |
| I-619 | 3-(5-chloro-pyridin-2-yl)-allyl | F | F | F | H |
| I-620 | 3-pyridin-4-yl-allyl | F | F | F | H |
| I-621 | 3-(2-Chloro-pyridin-4-yl)-allyl | F | F | F | H |
| I-622 | 4-chlorobenzyl | H | Cl | Cl | Cl |

TABLE 1-continued

| Compound No | R⁸ | R⁴ᵃ | R⁴ᵇ | R⁴ᶜ | R⁴ᵈ |
|---|---|---|---|---|---|
| I-623 | Cinnamyl | H | Cl | Cl | Cl |
| I-624 | 4-chlorocinnamyl | H | Cl | Cl | Cl |
| I-625 | 4-fluorocinnamyl | H | Cl | Cl | Cl |
| I-626 | 4-bromocinnamyl | H | Cl | Cl | Cl |
| I-627 | 4-trifluoromethylcinnamyl | H | Cl | Cl | Cl |
| I-628 | 4-trifluoromethoxycinnamyl | H | Cl | Cl | Cl |
| I-629 | 4-pentafluoroethoxycinnamyl | H | Cl | Cl | Cl |
| I-630 | 4-methoxycinnamyl | H | Cl | Cl | Cl |
| I-631 | 4-ethoxycinnamyl | H | Cl | Cl | Cl |
| I-632 | 4-cyanocinnamyl | H | Cl | Cl | Cl |
| I-633 | 3-(6-chloro-pyridin-3-yl)-allyl | H | Cl | Cl | Cl |
| I-634 | 3-(4-chlorophenyl)-but-2-enyl | H | Cl | Cl | Cl |
| I-635 | 3-(4-chlorophenyl)-3-fluoro-allyl | H | Cl | Cl | Cl |
| I-636 | 3-chloro-4-fluoro-cinnamyl | H | Cl | Cl | Cl |
| I-637 | 3,5-dichloro-cinnamyl | H | Cl | Cl | Cl |
| I-638 | 5-phenyl-penta-2,4-dienyl | H | Cl | Cl | Cl |
| I-639 | 4-isopropyloxycarbonylamino-cinnamyl | H | Cl | Cl | Cl |
| I-640 | 3-naphthalen-2-yl-allyl | H | Cl | Cl | Cl |
| I-641 | 3-(5-trifluoromethyl-pyridin-2-yl)-allyl | H | Cl | Cl | Cl |
| I-642 | 3-(5-chloro-pyridin-2-yl)-allyl | H | Cl | Cl | Cl |
| I-643 | 3-pyridin-4-yl-allyl | H | Cl | Cl | Cl |
| I-644 | 3-(2-Chloro-pyridin-4-yl)-allyl | H | Cl | Cl | Cl |
| I-645 | 4-chlorobenzyl | Cl | H | Cl | Cl |
| I-646 | Cinnamyl | Cl | H | Cl | Cl |
| I-647 | 4-chlorocinnamyl | Cl | H | Cl | Cl |
| I-648 | 4-fluorocinnamyl | Cl | H | Cl | Cl |
| I-649 | 4-bromocinnamyl | Cl | H | Cl | Cl |
| I-650 | 4-trifluoromethylcinnamyl | Cl | H | Cl | Cl |
| I-651 | 4-trifluoromethoxycinnamyl | Cl | H | Cl | Cl |
| I-652 | 4-pentafluoroethoxycinnamyl | Cl | H | Cl | Cl |
| I-653 | 4-methoxycinnamyl | Cl | H | Cl | Cl |
| I-654 | 4-ethoxycinnamyl | Cl | H | Cl | Cl |
| I-655 | 4-cyanocinnamyl | Cl | H | Cl | Cl |
| I-656 | 3-(6-chloro-pyridin-3-yl)-allyl | Cl | H | Cl | Cl |
| I-657 | 3-(4-chlorophenyl)-but-2-enyl | Cl | H | Cl | Cl |
| I-658 | 3-(4-chlorophenyl)-3-fluoro-allyl | Cl | H | Cl | Cl |
| I-659 | 3-chloro-4-fluoro-cinnamyl | Cl | H | Cl | Cl |
| I-660 | 3,5-dichloro-cinnamyl | Cl | H | Cl | Cl |
| I-661 | 5-phenyl-penta-2,4-dienyl | Cl | H | Cl | Cl |
| I-662 | 4-isopropyloxycarbonylamino-cinnamyl | Cl | H | Cl | Cl |
| I-663 | 3-naphthalen-2-yl-allyl | Cl | H | Cl | Cl |
| I-664 | 3-(5-trifluoromethyl-pyridin-2-yl)-allyl | Cl | H | Cl | Cl |
| I-665 | 3-(5-chloro-pyridin-2-yl)-allyl | Cl | H | Cl | Cl |
| I-666 | 3-pyridin-4-yl-allyl | Cl | H | Cl | Cl |
| I-667 | 3-(2-Chloro-pyridin-4-yl)-allyl | Cl | H | Cl | Cl |
| I-668 | 4-chlorobenzyl | Cl | Cl | H | Cl |
| I-669 | Cinnamyl | Cl | Cl | H | Cl |
| I-670 | 4-chlorocinnamyl | Cl | Cl | H | Cl |
| I-671 | 4-fluorocinnamyl | Cl | Cl | H | Cl |
| I-672 | 4-bromocinnamyl | Cl | Cl | H | Cl |
| I-673 | 4-trifluoromethylcinnamyl | Cl | Cl | H | Cl |
| I-674 | 4-trifluoromethoxycinnamyl | Cl | Cl | H | Cl |
| I-675 | 4-pentafluoroethoxycinnamyl | Cl | Cl | H | Cl |
| I-676 | 4-methoxycinnamyl | Cl | Cl | H | Cl |
| I-677 | 4-ethoxycinnamyl | Cl | Cl | H | Cl |
| I-678 | 4-cyanocinnamyl | Cl | Cl | H | Cl |
| I-679 | 3-(6-chloro-pyridin-3-yl)-allyl | Cl | Cl | H | Cl |
| I-680 | 3-(4-chlorophenyl)-but-2-enyl | Cl | Cl | H | Cl |
| I-681 | 3-(4-chlorophenyl)-3-fluoro-allyl | Cl | Cl | H | Cl |
| I-682 | 3-chloro-4-fluoro-cinnamyl | Cl | Cl | H | Cl |
| I-683 | 3,5-dichloro-cinnamyl | Cl | Cl | H | Cl |
| I-684 | 5-phenyl-penta-2,4-dienyl | Cl | Cl | H | Cl |
| I-685 | 4-isopropyloxycarbonylamino-cinnamyl | Cl | Cl | H | Cl |
| I-686 | 3-naphthalen-2-yl-allyl | Cl | Cl | H | Cl |
| I-687 | 3-(5-trifluoromethyl-pyridin-2-yl)-allyl | Cl | Cl | H | Cl |
| I-688 | 3-(5-chloro-pyridin-2-yl)-allyl | Cl | Cl | H | Cl |
| I-689 | 3-pyridin-4-yl-allyl | Cl | Cl | H | Cl |
| I-690 | 3-(2-Chloro-pyridin-4-yl)-allyl | Cl | Cl | H | Cl |

TABLE 1-continued

| Compound No | R⁸ | R⁴ᵃ | R⁴ᵇ | R⁴ᶜ | R⁴ᵈ |
|---|---|---|---|---|---|
| I-691 | 4-chlorobenzyl | Cl | Cl | Cl | H |
| I-692 | Cinnamyl | Cl | Cl | Cl | H |
| I-693 | 4-chlorocinnamyl | Cl | Cl | Cl | H |
| I-694 | 4-fluorocinnamyl | Cl | Cl | Cl | H |
| I-695 | 4-bromocinnamyl | Cl | Cl | Cl | H |
| I-696 | 4-trifluoromethylcinnamyl | Cl | Cl | Cl | H |
| I-697 | 4-trifluoromethoxycinnamyl | Cl | Cl | Cl | H |
| I-698 | 4-pentafluoroethoxycinnamyl | Cl | Cl | Cl | H |
| I-699 | 4-methoxycinnamyl | Cl | Cl | Cl | H |
| I-700 | 4-ethoxycinnamyl | Cl | Cl | Cl | H |
| I-701 | 4-cyanocinnamyl | Cl | Cl | Cl | H |
| I-702 | 3-(6-chloro-pyridin-3-yl)-allyl | Cl | Cl | Cl | H |
| I-703 | 3-(4-chlorophenyl)-but-2-enyl | Cl | Cl | Cl | H |
| I-704 | 3-(4-chlorophenyl)-3-fluoro-allyl | Cl | Cl | Cl | H |
| I-705 | 3-chloro-4-fluoro-cinnamyl | Cl | Cl | Cl | H |
| I-706 | 3,5-dichloro-cinnamyl | Cl | Cl | Cl | H |
| I-707 | 5-phenyl-penta-2,4-dienyl | Cl | Cl | Cl | H |
| I-708 | 4-isopropyloxycarbonylamino-cinnamyl | Cl | Cl | Cl | H |
| I-709 | 3-naphthalen-2-yl-allyl | Cl | Cl | Cl | H |
| I-710 | 3-(5-trifluoromethyl-pyridin-2-yl)-allyl | Cl | Cl | Cl | H |
| I-711 | 3-(5-chloro-pyridin-2-yl)-allyl | Cl | Cl | Cl | H |
| I-712 | 3-pyridin-4-yl-allyl | Cl | Cl | Cl | H |
| I-713 | 3-(2-Chloro-pyridin-4-yl)-allyl | Cl | Cl | Cl | H |
| I-714 | 4-chlorobenzyl | Cl | Cl | Cl | Cl |
| I-715 | Cinnamyl | Cl | Cl | Cl | Cl |
| I-716 | 4-chlorocinnamyl | Cl | Cl | Cl | Cl |
| I-717 | 4-fluorocinnamyl | Cl | Cl | Cl | Cl |
| I-718 | 4-bromocinnamyl | Cl | Cl | Cl | Cl |
| I-719 | 4-trifluoromethylcinnamyl | Cl | Cl | Cl | Cl |
| I-720 | 4-trifluoromethoxycinnamyl | Cl | Cl | Cl | Cl |
| I-721 | 4-pentafluoroethoxycinnamyl | Cl | Cl | Cl | Cl |
| I-722 | 4-methoxycinnamyl | Cl | Cl | Cl | Cl |
| I-723 | 4-ethoxycinnamyl | Cl | Cl | Cl | Cl |
| I-724 | 4-cyanocinnamyl | Cl | Cl | Cl | Cl |
| I-725 | 3-(6-chloro-pyridin-3-yl)-allyl | Cl | Cl | Cl | Cl |
| I-726 | 3-(4-chlorophenyl)-but-2-enyl | Cl | Cl | Cl | Cl |
| I-727 | 3-(4-chlorophenyl)-3-fluoro-allyl | Cl | Cl | Cl | Cl |
| I-728 | 3-chloro-4-fluoro-cinnamyl | Cl | Cl | Cl | Cl |
| I-729 | 3,5-dichloro-cinnamyl | Cl | Cl | Cl | Cl |
| I-730 | 5-phenyl-penta-2,4-dienyl | Cl | Cl | Cl | Cl |
| I-731 | 4-isopropyloxycarbonylamino-cinnamyl | Cl | Cl | Cl | Cl |
| I-732 | 3-naphthalen-2-yl-allyl | Cl | Cl | Cl | Cl |
| I-733 | 3-(5-trifluoromethyl-pyridin-2-yl)-allyl | Cl | Cl | Cl | Cl |
| I-734 | 3-(5-chloro-pyridin-2-yl)-allyl | Cl | Cl | Cl | Cl |
| I-735 | 3-pyridin-4-yl-allyl | Cl | Cl | Cl | Cl |
| I-736 | 3-(2-Chloro-pyridin-4-yl)-allyl | Cl | Cl | Cl | Cl |
| I-737 | 4-chlorobenzyl | F | F | F | F |
| I-738 | Cinnamyl | F | F | F | F |
| I-739 | 4-chlorocinnamyl | F | F | F | F |
| I-740 | 4-fluorocinnamyl | F | F | F | F |
| I-741 | 4-bromocinnamyl | F | F | F | F |
| I-742 | 4-trifluoromethylcinnamyl | F | F | F | F |
| I-743 | 4-trifluoromethoxycinnamyl | F | F | F | F |
| I-744 | 4-pentafluoroethoxycinnamyl | F | F | F | F |
| I-745 | 4-methoxycinnamyl | F | F | F | F |
| I-746 | 4-ethoxycinnamyl | F | F | F | F |
| I-747 | 4-cyanocinnamyl | F | F | F | F |
| I-748 | 3-(6-chloro-pyridin-3-yl)-allyl | F | F | F | F |
| I-749 | 3-(4-chlorophenyl)-but-2-enyl | F | F | F | F |
| I-750 | 3-(4-chlorophenyl)-3-fluoro-allyl | F | F | F | F |
| I-751 | 3-chloro-4-fluoro-cinnamyl | F | F | F | F |
| I-752 | 3,5-dichloro-cinnamyl | F | F | F | F |
| I-753 | 5-phenyl-penta-2,4-dienyl | F | F | F | F |
| I-754 | 4-isopropyloxycarbonylamino-cinnamyl | F | F | F | F |
| I-755 | 3-naphthalen-2-yl-allyl | F | F | F | F |
| I-756 | 3-(5-trifluoromethyl-pyridin-2-yl)-allyl | F | F | F | F |
| I-757 | 3-(5-chloro-pyridin-2-yl)-allyl | F | F | F | F |
| I-758 | 3-pyridin-4-yl-allyl | F | F | F | F |

TABLE 1-continued

| Compound No | R⁸ | R⁴ᵃ | R⁴ᵇ | R⁴ᶜ | R⁴ᵈ |
|---|---|---|---|---|---|
| I-759 | 3-(2-Chloro-pyridin-4-yl)-allyl | F | F | F | F |
| I-760 | 4-chlorobenzyl | H | F | H | F |
| I-761 | Cinnamyl | H | F | H | F |
| I-762 | 4-chlorocinnamyl | H | F | H | F |
| I-763 | 4-fluorocinnamyl | H | F | H | F |
| I-764 | 4-bromocinnamyl | H | F | H | F |
| I-765 | 4-trifluoromethylcinnamyl | H | F | H | F |
| I-766 | 4-trifluoromethoxycinnamyl | H | F | H | F |
| I-767 | 4-pentafluoroethoxycinnamyl | H | F | H | F |
| I-768 | 4-methoxycinnamyl | H | F | H | F |
| I-769 | 4-ethoxycinnamyl | H | F | H | F |
| I-770 | 4-cyanocinnamyl | H | F | H | F |
| I-771 | 3-(6-chloro-pyridin-3-yl)-allyl | H | F | H | F |
| I-772 | 3-(4-chlorophenyl)-but-2-enyl | H | F | H | F |
| I-773 | 3-(4-chlorophenyl)-3-fluoro-allyl | H | F | H | F |
| I-774 | 3-chloro-4-fluoro-cinnamyl | H | F | H | F |
| I-775 | 3,5-dichloro-cinnamyl | H | F | H | F |
| I-776 | 5-phenyl-penta-2,4-dienyl | H | F | H | F |
| I-777 | 4-isopropyloxycarbonylamino-cinnamyl | H | F | H | F |
| I-778 | 3-naphthalen-2-yl-allyl | H | F | H | F |
| I-779 | 3-(5-trifluoromethyl-pyridin-2-yl)-allyl | H | F | H | F |
| I-780 | 3-(5-chloro-pyridin-2-yl)-allyl | H | F | H | F |
| I-781 | 3-pyridin-4-yl-allyl | H | F | H | F |
| I-782 | 3-(2-Chloro-pyridin-4-yl)-allyl | H | F | H | F |
| I-783 | 4-chlorobenzyl | H | F | F | H |
| I-784 | Cinnamyl | H | F | F | H |
| I-785 | 4-chlorocinnamyl | H | F | F | H |
| I-786 | 4-fluorocinnamyl | H | F | F | H |
| I-787 | 4-bromocinnamyl | H | F | F | H |
| I-788 | 4-trifluoromethylcinnamyl | H | F | F | H |
| I-789 | 4-trifluoromethoxycinnamyl | H | F | F | H |
| I-790 | 4-pentafluoroethoxycinnamyl | H | F | F | H |
| I-791 | 4-methoxycinnamyl | H | F | F | H |
| I-792 | 4-ethoxycinnamyl | H | F | F | H |
| I-793 | 4-cyanocinnamyl | H | F | F | H |
| I-794 | 3-(6-chloro-pyridin-3-yl)-allyl | H | F | F | H |
| I-795 | 3-(4-chlorophenyl)-but-2-enyl | H | F | F | H |
| I-796 | 3-(4-chlorophenyl)-3-fluoro-allyl | H | F | F | H |
| I-797 | 3-chloro-4-fluoro-cinnamyl | H | F | F | H |
| I-798 | 3,5-dichloro-cinnamyl | H | F | F | H |
| I-799 | 5-phenyl-penta-2,4-dienyl | H | F | F | H |
| I-800 | 4-isopropyloxycarbonylamino-cinnamyl | H | F | F | H |
| I-801 | 3-naphthalen-2-yl-allyl | H | F | F | H |
| I-802 | 3-(5-trifluoromethyl-pyridin-2-yl)-allyl | H | F | F | H |
| I-803 | 3-(5-chloro-pyridin-2-yl)-allyl | H | F | F | H |
| I-804 | 3-pyridin-4-yl-allyl | H | F | F | H |
| I-805 | 3-(2-Chloro-pyridin-4-yl)-allyl | H | F | F | H |
| I-806 | 4-chlorobenzyl | H | F | F | H |
| I-807 | Cinnamyl | H | H | F | F |
| I-808 | 4-chlorocinnamyl | H | H | F | F |
| I-809 | 4-fluorocinnamyl | H | H | F | F |
| I-810 | 4-bromocinnamyl | H | H | F | F |
| I-811 | 4-trifluoromethylcinnamyl | H | H | F | F |
| I-812 | 4-trifluoromethoxycinnamyl | H | H | F | F |
| I-813 | 4-pentafluoroethoxycinnamyl | H | H | F | F |
| I-814 | 4-methoxycinnamyl | H | H | F | F |
| I-815 | 4-ethoxycinnamyl | H | H | F | F |
| I-816 | 4-cyanocinnamyl | H | H | F | F |
| I-817 | 3-(6-chloro-pyridin-3-yl)-allyl | H | H | F | F |
| I-818 | 3-(4-chlorophenyl)-but-2-enyl | H | H | F | F |
| I-819 | 3-(4-chlorophenyl)-3-fluoro-allyl | H | H | F | F |
| I-820 | 3-chloro-4-fluoro-cinnamyl | H | H | F | F |
| I-821 | 3,5-dichloro-cinnamyl | H | H | F | F |
| I-822 | 5-phenyl-penta-2,4-dienyl | H | H | F | F |
| I-823 | 4-isopropyloxycarbonylamino-cinnamyl | H | H | F | F |
| I-824 | 3-naphthalen-2-yl-allyl | H | H | F | F |
| I-825 | 3-(5-trifluoromethyl-pyridin-2-yl)-allyl | H | H | F | F |
| I-826 | 3-(5-chloro-pyridin-2-yl)-allyl | H | H | F | F |

TABLE 1-continued

| Compound No | R⁸ | R⁴ᵃ | R⁴ᵇ | R⁴ᶜ | R⁴ᵈ |
|---|---|---|---|---|---|
| I-827 | 3-pyridin-4-yl-allyl | H | H | F | F |
| I-828 | 3-(2-Chloro-pyridin-4-yl)-allyl | H | H | F | F |
| I-829 | 4-chlorobenzyl | H | H | Cl | Cl |
| I-830 | Cinnamyl | H | H | Cl | Cl |
| I-831 | 4-chlorocinnamyl | H | H | Cl | Cl |
| I-832 | 4-fluorocinnamyl | H | H | Cl | Cl |
| I-833 | 4-bromocinnamyl | H | H | Cl | Cl |
| I-834 | 4-trifluoromethylcinnamyl | H | H | Cl | Cl |
| I-835 | 4-trifluoromethoxycinnamyl | H | H | Cl | Cl |
| I-836 | 4-pentafluoroethoxycinnamyl | H | H | Cl | Cl |
| I-837 | 4-methoxycinnamyl | H | H | Cl | Cl |
| I-838 | 4-ethoxycinnamyl | H | H | Cl | Cl |
| I-839 | 4-cyanocinnamyl | H | H | Cl | Cl |
| I-840 | 3-(6-chloro-pyridin-3-yl)-allyl | H | H | Cl | Cl |
| I-841 | 3-(4-chlorophenyl)-but-2-enyl | H | H | Cl | Cl |
| I-842 | 3-(4-chlorophenyl)-3-fluoro-allyl | H | H | Cl | Cl |
| I-843 | 3-chloro-4-fluoro-cinnamyl | H | H | Cl | Cl |
| I-844 | 3,5-dichloro-cinnamyl | H | H | Cl | Cl |
| I-845 | 5-phenyl-penta-2,4-dienyl | H | H | Cl | Cl |
| I-846 | 4-isopropyloxycarbonylamino-cinnamyl | H | H | Cl | Cl |
| I-847 | 3-naphthalen-2-yl-allyl | H | H | Cl | Cl |
| I-848 | 3-(5-trifluoromethyl-pyridin-2-yl)-allyl | H | H | Cl | Cl |
| I-849 | 3-(5-chloro-pyridin-2-yl)-allyl | H | H | Cl | Cl |
| I-850 | 3-pyridin-4-yl-allyl | H | H | Cl | Cl |
| I-851 | 3-(2-Chloro-pyridin-4-yl)-allyl | H | H | Cl | Cl |
| I-852 | 4-chlorobenzyl | H | Cl | Cl | H |
| I-853 | Cinnamyl | H | Cl | Cl | H |
| I-854 | 4-chlorocinnamyl | H | Cl | Cl | H |
| I-855 | 4-fluorocinnamyl | H | Cl | Cl | H |
| I-856 | 4-bromocinnamyl | H | Cl | Cl | H |
| I-857 | 4-trifluoromethylcinnamyl | H | Cl | Cl | H |
| I-858 | 4-trifluoromethoxycinnamyl | H | Cl | Cl | H |
| I-859 | 4-pentafluoroethoxycinnamyl | H | Cl | Cl | H |
| I-860 | 4-methoxycinnamyl | H | Cl | Cl | H |
| I-861 | 4-ethoxycinnamyl | H | Cl | Cl | H |
| I-862 | 4-cyanocinnamyl | H | Cl | Cl | H |
| I-863 | 3-(6-chloro-pyridin-3-yl)-allyl | H | Cl | Cl | H |
| I-864 | 3-(4-chlorophenyl)-but-2-enyl | H | Cl | Cl | H |
| I-865 | 3-(4-chlorophenyl)-3-fluoro-allyl | H | Cl | Cl | H |
| I-866 | 3-chloro-4-fluoro-cinnamyl | H | Cl | Cl | H |
| I-867 | 3,5-dichloro-cinnamyl | H | Cl | Cl | H |
| I-868 | 5-phenyl-penta-2,4-dienyl | H | Cl | Cl | H |
| I-869 | 4-isopropyloxycarbonylamino-cinnamyl | H | Cl | Cl | H |
| I-870 | 3-naphthalen-2-yl-allyl | H | Cl | Cl | H |
| I-871 | 3-(5-trifluoromethyl-pyridin-2-yl)-allyl | H | Cl | Cl | H |
| I-872 | 3-(5-chloro-pyridin-2-yl)-allyl | H | Cl | Cl | H |
| I-873 | 3-pyridin-4-yl-allyl | H | Cl | Cl | H |
| I-874 | 3-(2-Chloro-pyridin-4-yl)-allyl | H | Cl | Cl | H |
| I-875 | 4-chlorobenzyl | H | Cl | H | Cl |
| I-876 | Cinnamyl | H | Cl | H | Cl |
| I-877 | 4-chlorocinnamyl | H | Cl | H | Cl |
| I-878 | 4-fluorocinnamyl | H | Cl | H | Cl |
| I-879 | 4-bromocinnamyl | H | Cl | H | Cl |
| I-880 | 4-trifluoromethylcinnamyl | H | Cl | H | Cl |
| I-881 | 4-trifluoromethoxycinnamyl | H | Cl | H | Cl |
| I-882 | 4-pentafluoroethoxycinnamyl | H | Cl | H | Cl |
| I-883 | 4-methoxycinnamyl | H | Cl | H | Cl |
| I-884 | 4-ethoxycinnamyl | H | Cl | H | Cl |
| I-885 | 4-cyanocinnamyl | H | Cl | H | Cl |
| I-886 | 3-(6-chloro-pyridin-3-yl)-allyl | H | Cl | H | Cl |
| I-887 | 3-(4-chlorophenyl)-but-2-enyl | H | Cl | H | Cl |
| I-888 | 3-(4-chlorophenyl)-3-fluoro-allyl | H | Cl | H | Cl |
| I-889 | 3-chloro-4-fluoro-cinnamyl | H | Cl | H | Cl |
| I-890 | 3,5-dichloro-cinnamyl | H | Cl | H | Cl |
| I-891 | 5-phenyl-penta-2,4-dienyl | H | Cl | H | Cl |
| I-892 | 4-isopropyloxycarbonylamino-cinnamyl | H | Cl | H | Cl |
| I-893 | 3-naphthalen-2-yl-allyl | H | Cl | H | Cl |
| I-894 | 3-(5-trifluoromethyl-pyridin-2-yl)-allyl | H | Cl | H | Cl |

TABLE 1-continued

| Compound No | R⁸ | R⁴ᵃ | R⁴ᵇ | R⁴ᶜ | R⁴ᵈ |
|---|---|---|---|---|---|
| I-895 | 3-(5-chloro-pyridin-2-yl)-allyl | H | Cl | H | Cl |
| I-896 | 3-pyridin-4-yl-allyl | H | Cl | H | Cl |
| I-897 | 3-(2-Chloro-pyridin-4-yl)-allyl | H | Cl | H | Cl |
| I-898 | 4-chlorobenzyl | H | H | CH₃ | H |
| I-899 | Cinnamyl | H | H | CH₃ | H |
| I-900 | 4-chlorocinnamyl | H | H | CH₃ | H |
| I-901 | 4-fluorocinnamyl | H | H | CH₃ | H |
| I-902 | 4-bromocinnamyl | H | H | CH₃ | H |
| I-903 | 4-trifluoromethylcinnamyl | H | H | CH₃ | H |
| I-904 | 4-trifluoromethoxycinnamyl | H | H | CH₃ | H |
| I-905 | 4-pentafluoroethoxycinnamyl | H | H | CH₃ | H |
| I-906 | 4-methoxycinnamyl | H | H | CH₃ | H |
| I-907 | 4-ethoxycinnamyl | H | H | CH₃ | H |
| I-908 | 4-cyanocinnamyl | H | H | CH₃ | H |
| I-909 | 3-(6-chloro-pyridin-3-yl)-allyl | H | H | CH₃ | H |
| I-910 | 3-(4-chlorophenyl)-but-2-enyl | H | H | CH₃ | H |
| I-911 | 3-(4-chlorophenyl)-3-fluoro-allyl | H | H | CH₃ | H |
| I-912 | 3-chloro-4-fluoro-cinnamyl | H | H | CH₃ | H |
| I-913 | 3,5-dichloro-cinnamyl | H | H | CH₃ | H |
| I-914 | 5-phenyl-penta-2,4-dienyl | H | H | CH₃ | H |
| I-915 | 4-isopropyloxycarbonylamino-cinnamyl | H | H | CH₃ | H |
| I-916 | 3-naphthalen-2-yl-allyl | H | H | CH₃ | H |
| I-917 | 3-(5-trifluoromethyl-pyridin-2-yl)-allyl | H | H | CH₃ | H |
| I-918 | 3-(5-chloro-pyridin-2-yl)-allyl | H | H | CH₃ | H |
| I-919 | 3-pyridin-4-yl-allyl | H | H | CH₃ | H |
| I-920 | 3-(2-Chloro-pyridin-4-yl)-allyl | H | H | CH₃ | H |
| I-921 | 4-chlorobenzyl | H | H | CF₃ | H |
| I-922 | Cinnamyl | H | H | CF₃ | H |
| I-923 | 4-chlorocinnamyl | H | H | CF₃ | H |
| I-924 | 4-fluorocinnamyl | H | H | CF₃ | H |
| I-925 | 4-bromocinnamyl | H | H | CF₃ | H |
| I-926 | 4-trifluoromethylcinnamyl | H | H | CF₃ | H |
| I-927 | 4-trifluoromethoxycinnamyl | H | H | CF₃ | H |
| I-928 | 4-pentafluoroethoxycinnamyl | H | H | CF₃ | H |
| I-929 | 4-methoxycinnamyl | H | H | CF₃ | H |
| I-930 | 4-ethoxycinnamyl | H | H | CF₃ | H |
| I-931 | 4-cyanocinnamyl | H | H | CF₃ | H |
| I-932 | 3-(6-chloro-pyridin-3-yl)-allyl | H | H | CF₃ | H |
| I-933 | 3-(4-chlorophenyl)-but-2-enyl | H | H | CF₃ | H |
| I-934 | 3-(4-chlorophenyl)-3-fluoro-allyl | H | H | CF₃ | H |
| I-935 | 3-chloro-4-fluoro-cinnamyl | H | H | CF₃ | H |
| I-936 | 3,5-dichloro-cinnamyl | H | H | CF₃ | H |
| I-937 | 5-phenyl-penta-2,4-dienyl | H | H | CF₃ | H |
| I-938 | 4-isopropyloxycarbonylamino-cinnamyl | H | H | CF₃ | H |
| I-939 | 3-naphthalen-2-yl-allyl | H | H | CF₃ | H |
| I-940 | 3-(5-trifluoromethyl-pyridin-2-yl)-allyl | H | H | CF₃ | H |
| I-941 | 3-(5-chloro-pyridin-2-yl)-allyl | H | H | CF₃ | H |
| I-942 | 3-pyridin-4-yl-allyl | H | H | CF₃ | H |
| I-943 | 3-(2-Chloro-pyridin-4-yl)-allyl | H | H | CF₃ | H |
| I-944 | 4-chlorobenzyl | H | H | OCH₃ | H |
| I-945 | Cinnamyl | H | H | OCH₃ | H |
| I-946 | 4-chlorocinnamyl | H | H | OCH₃ | H |
| I-947 | 4-fluorocinnamyl | H | H | OCH₃ | H |
| I-948 | 4-bromocinnamyl | H | H | OCH₃ | H |
| I-949 | 4-trifluoromethylcinnamyl | H | H | OCH₃ | H |
| I-950 | 4-trifluoromethoxycinnamyl | H | H | OCH₃ | H |
| I-951 | 4-pentafluoroethoxycinnamyl | H | H | OCH₃ | H |
| I-952 | 4-methoxycinnamyl | H | H | OCH₃ | H |
| I-953 | 4-ethoxycinnamyl | H | H | OCH₃ | H |
| I-954 | 4-cyanocinnamyl | H | H | OCH₃ | H |
| I-955 | 3-(6-chloro-pyridin-3-yl)-allyl | H | H | OCH₃ | H |
| I-956 | 3-(4-chlorophenyl)-but-2-enyl | H | H | OCH₃ | H |
| I-957 | 3-(4-chlorophenyl)-3-fluoro-allyl | H | H | OCH₃ | H |
| I-958 | 3-chloro-4-fluoro-cinnamyl | H | H | OCH₃ | H |
| I-959 | 3,5-dichloro-cinnamyl | H | H | OCH₃ | H |
| I-960 | 5-phenyl-penta-2,4-dienyl | H | H | OCH₃ | H |
| I-961 | 4-isopropyloxycarbonylamino-cinnamyl | H | H | OCH₃ | H |
| I-962 | 3-naphthalen-2-yl-allyl | H | H | OCH₃ | H |

TABLE 1-continued

| Compound No | R⁸ | R⁴ᵃ | R⁴ᵇ | R⁴ᶜ | R⁴ᵈ |
|---|---|---|---|---|---|
| I-963 | 3-(5-trifluoromethyl-pyridin-2-yl)-allyl | H | H | OCH₃ | H |
| I-964 | 3-(5-chloro-pyridin-2-yl)-allyl | H | H | OCH₃ | H |
| I-965 | 3-pyridin-4-yl-allyl | H | H | OCH₃ | H |
| I-966 | 3-(2-Chloro-pyridin-4-yl)-allyl | H | H | OCH₃ | H |
| I-967 | 4-chlorobenzyl | H | H | CO₂CH₃ | H |
| I-968 | Cinnamyl | H | H | CO₂CH₃ | H |
| I-969 | 4-chlorocinnamyl | H | H | CO₂CH₃ | H |
| I-970 | 4-fluorocinnamyl | H | H | CO₂CH₃ | H |
| I-971 | 4-bromocinnamyl | H | H | CO₂CH₃ | H |
| I-972 | 4-trifluoromethylcinnamyl | H | H | CO₂CH₃ | H |
| I-973 | 4-trifluoromethoxycinnamyl | H | H | CO₂CH₃ | H |
| I-974 | 4-pentafluoroethoxycinnamyl | H | H | CO₂CH₃ | H |
| I-975 | 4-methoxycinnamyl | H | H | CO₂CH₃ | H |
| I-976 | 4-ethoxycinnamyl | H | H | CO₂CH₃ | H |
| I-977 | 4-cyanocinnamyl | H | H | CO₂CH₃ | H |
| I-978 | 3-(6-chloro-pyridin-3-yl)-allyl | H | H | CO₂CH₃ | H |
| I-979 | 3-(4-chlorophenyl)-but-2-enyl | H | H | CO₂CH₃ | H |
| I-980 | 3-(4-chlorophenyl)-3-fluoro-allyl | H | H | CO₂CH₃ | H |
| I-981 | 3-chloro-4-fluoro-cinnamyl | H | H | CO₂CH₃ | H |
| I-982 | 3,5-dichloro-cinnamyl | H | H | CO₂CH₃ | H |
| I-983 | 5-phenyl-penta-2,4-dienyl | H | H | CO₂CH₃ | H |
| I-984 | 4-isopropyloxycarbonylamino-cinnamyl | H | H | CO₂CH₃ | H |
| I-985 | 3-naphthalen-2-yl-allyl | H | H | CO₂CH₃ | H |
| I-986 | 3-(5-trifluoromethyl-pyridin-2-yl)-allyl | H | H | CO₂CH₃ | H |
| I-987 | 3-(5-chloro-pyridin-2-yl)-allyl | H | H | CO₂CH₃ | H |
| I-988 | 3-pyridin-4-yl-allyl | H | H | CO₂CH₃ | H |
| I-989 | 3-(2-Chloro-pyridin-4-yl)-allyl | H | H | CO₂CH₃ | H |
| I-990 | 4-chlorobenzyl | CH₃ | H | H | H |
| I-991 | Cinnamyl | CH₃ | H | H | H |
| I-992 | 4-chlorocinnamyl | CH₃ | H | H | H |
| I-993 | 4-fluorocinnamyl | CH₃ | H | H | H |
| I-994 | 4-bromocinnamyl | CH₃ | H | H | H |
| I-995 | 4-trifluoromethylcinnamyl | CH₃ | H | H | H |
| I-996 | 4-trifluoromethoxycinnamyl | CH₃ | H | H | H |
| I-997 | 4-pentafluoroethoxycinnamyl | CH₃ | H | H | H |
| I-998 | 4-methoxycinnamyl | CH₃ | H | H | H |
| I-999 | 4-ethoxycinnamyl | CH₃ | H | H | H |
| I-1000 | 4-cyanocinnamyl | CH₃ | H | H | H |
| I-1001 | 3-(6-chloro-pyridin-3-yl)-allyl | CH₃ | H | H | H |
| I-1002 | 3-(4-chlorophenyl)-but-2-enyl | CH₃ | H | H | H |
| I-1003 | 3-(4-chlorophenyl)-3-fluoro-allyl | CH₃ | H | H | H |
| I-1004 | 3-chloro-4-fluoro-cinnamyl | CH₃ | H | H | H |
| I-1005 | 3,5-dichloro-cinnamyl | CH₃ | H | H | H |
| I-1006 | 5-phenyl-penta-2,4-dienyl | CH₃ | H | H | H |
| I-1007 | 4-isopropyloxycarbonylamino-cinnamyl | CH₃ | H | H | H |
| I-1008 | 3-naphthalen-2-yl-allyl | CH₃ | H | H | H |
| I-1009 | 3-(5-trifluoromethyl-pyridin-2-yl)-allyl | CH₃ | H | H | H |
| I-1010 | 3-(5-chloro-pyridin-2-yl)-allyl | CH₃ | H | H | H |
| I-1011 | 3-pyridin-4-yl-allyl | CH₃ | H | H | H |
| I-1012 | 3-(2-Chloro-pyridin-4-yl)-allyl | CH₃ | H | H | H |
| I-1013 | 4-chlorobenzyl | H | CH₃ | H | H |
| I-1014 | Cinnamyl | H | CH₃ | H | H |
| I-1015 | 4-chlorocinnamyl | H | CH₃ | H | H |
| I-1016 | 4-fluorocinnamyl | H | CH₃ | H | H |
| I-1017 | 4-bromocinnamyl | H | CH₃ | H | H |
| I-1018 | 4-trifluoromethylcinnamyl | H | CH₃ | H | H |
| I-1019 | 4-trifluoromethoxycinnamyl | H | CH₃ | H | H |
| I-1020 | 4-pentafluoroethoxycinnamyl | H | CH₃ | H | H |
| I-1021 | 4-methoxycinnamyl | H | CH₃ | H | H |
| I-1022 | 4-ethoxycinnamyl | H | CH₃ | H | H |
| I-1023 | 4-cyanocinnamyl | H | CH₃ | H | H |
| I-1024 | 3-(6-chloro-pyridin-3-yl)-allyl | H | CH₃ | H | H |
| I-1025 | 3-(4-chlorophenyl)-but-2-enyl | H | CH₃ | H | H |
| I-1026 | 3-(4-chlorophenyl)-3-fluoro-allyl | H | CH₃ | H | H |
| I-1027 | 3-chloro-4-fluoro-cinnamyl | H | CH₃ | H | H |
| I-1028 | 3,5-dichloro-cinnamyl | H | CH₃ | H | H |
| I-1029 | 5-phenyl-penta-2,4-dienyl | H | CH₃ | H | H |
| I-1030 | 4-isopropyloxycarbonylamino-cinnamyl | H | CH₃ | H | H |

TABLE 1-continued

| Compound No | R⁸ | R⁴ᵃ | R⁴ᵇ | R⁴ᶜ | R⁴ᵈ |
|---|---|---|---|---|---|
| I-1031 | 3-naphthalen-2-yl-allyl | H | CH₃ | H | H |
| I-1032 | 3-(5-trifluoromethyl-pyridin-2-yl)-allyl | H | CH₃ | H | H |
| I-1033 | 3-(5-chloro-pyridin-2-yl)-allyl | H | CH₃ | H | H |
| I-1034 | 3-pyridin-4-yl-allyl | H | CH₃ | H | H |
| I-1035 | 3-(2-Chloro-pyridin-4-yl)-allyl | H | CH₃ | H | H |
| I-1036 | 4-chlorobenzyl | H | H | H | CH₃ |
| I-1037 | Cinnamyl | H | H | H | CH₃ |
| I-1038 | 4-chlorocinnamyl | H | H | H | CH₃ |
| I-1039 | 4-fluorocinnamyl | H | H | H | CH₃ |
| I-1040 | 4-bromocinnamyl | H | H | H | CH₃ |
| I-1041 | 4-trifluoromethylcinnamyl | H | H | H | CH₃ |
| I-1042 | 4-trifluoromethoxycinnamyl | H | H | H | CH₃ |
| I-1043 | 4-pentafluoroethoxycinnamyl | H | H | H | CH₃ |
| I-1044 | 4-methoxycinnamyl | H | H | H | CH₃ |
| I-1045 | 4-ethoxycinnamyl | H | H | H | CH₃ |
| I-1046 | 4-cyanocinnamyl | H | H | H | CH₃ |
| I-1047 | 3-(6-chloro-pyridin-3-yl)-allyl | H | H | H | CH₃ |
| I-1048 | 3-(4-chlorophenyl)-but-2-enyl | H | H | H | CH₃ |
| I-1049 | 3-(4-chlorophenyl)-3-fluoro-allyl | H | H | H | CH₃ |
| I-1050 | 3-chloro-4-fluoro-cinnamyl | H | H | H | CH₃ |
| I-1051 | 3,5-dichloro-cinnamyl | H | H | H | CH₃ |
| I-1052 | 5-phenyl-penta-2,4-dienyl | H | H | H | CH₃ |
| I-1053 | 4-isopropyloxycarbonylamino-cinnamyl | H | H | H | CH₃ |
| I-1054 | 3-naphthalen-2-yl-allyl | H | H | H | CH₃ |
| I-1055 | 3-(5-trifluoromethyl-pyridin-2-yl)-allyl | H | H | H | CH₃ |
| I-1056 | 3-(5-chloro-pyridin-2-yl)-allyl | H | H | H | CH₃ |
| I-1057 | 3-pyridin-4-yl-allyl | H | H | H | CH₃ |
| I-1058 | 3-(2-Chloro-pyridin-4-yl)-allyl | H | H | H | CH₃ |
| I-1059 | 4-chlorobenzyl | H | CF₃ | H | H |
| I-1060 | Cinnamyl | H | CF₃ | H | H |
| I-1061 | 4-chlorocinnamyl | H | CF₃ | H | H |
| I-1062 | 4-fluorocinnamyl | H | CF₃ | H | H |
| I-1063 | 4-bromocinnamyl | H | CF₃ | H | H |
| I-1064 | 4-trifluoromethylcinnamyl | H | CF₃ | H | H |
| I-1065 | 4-trifluoromethoxycinnamyl | H | CF₃ | H | H |
| I-1066 | 4-pentafluoroethoxycinnamyl | H | CF₃ | H | H |
| I-1067 | 4-methoxycinnamyl | H | CF₃ | H | H |
| I-1068 | 4-ethoxycinnamyl | H | CF₃ | H | H |
| I-1069 | 4-cyanocinnamyl | H | CF₃ | H | H |
| I-1070 | 3-(6-chloro-pyridin-3-yl)-allyl | H | CF₃ | H | H |
| I-1071 | 3-(4-chlorophenyl)-but-2-enyl | H | CF₃ | H | H |
| I-1072 | 3-(4-chlorophenyl)-3-fluoro-allyl | H | CF₃ | H | H |
| I-1073 | 3-chloro-4-fluoro-cinnamyl | H | CF₃ | H | H |
| I-1074 | 3,5-dichloro-cinnamyl | H | CF₃ | H | H |
| I-1075 | 5-phenyl-penta-2,4-dienyl | H | CF₃ | H | H |
| I-1076 | 4-isopropyloxycarbonylamino-cinnamyl | H | CF₃ | H | H |
| I-1077 | 3-naphthalen-2-yl-allyl | H | CF₃ | H | H |
| I-1078 | 3-(5-trifluoromethyl-pyridin-2-yl)-allyl | H | CF₃ | H | H |
| I-1079 | 3-(5-chloro-pyridin-2-yl)-allyl | H | CF₃ | H | H |
| I-1080 | 3-pyridin-4-yl-allyl | H | CF₃ | H | H |
| I-1081 | 3-(2-Chloro-pyridin-4-yl)-allyl | H | CF₃ | H | H |
| I-1082 | 4-chlorobenzyl | H | iPr | H | H |
| I-1083 | Cinnamyl | H | iPr | H | H |
| I-1084 | 4-chlorocinnamyl | H | iPr | H | H |
| I-1085 | 4-fluorocinnamyl | H | iPr | H | H |
| I-1086 | 4-bromocinnamyl | H | iPr | H | H |
| I-1087 | 4-trifluoromethylcinnamyl | H | iPr | H | H |
| I-1088 | 4-trifluoromethoxycinnamyl | H | iPr | H | H |
| I-1089 | 4-pentafluoroethoxycinnamyl | H | iPr | H | H |
| I-1090 | 4-methoxycinnamyl | H | iPr | H | H |
| I-1091 | 4-ethoxycinnamyl | H | iPr | H | H |
| I-1092 | 4-cyanocinnamyl | H | iPr | H | H |
| I-1093 | 3-(6-chloro-pyridin-3-yl)-allyl | H | iPr | H | H |
| I-1094 | 3-(4-chlorophenyl)-but-2-enyl | H | iPr | H | H |
| I-1095 | 3-(4-chlorophenyl)-3-fluoro-allyl | H | iPr | H | H |
| I-1096 | 3-chloro-4-fluoro-cinnamyl | H | iPr | H | H |
| I-1097 | 3,5-dichloro-cinnamyl | H | iPr | H | H |
| I-1098 | 5-phenyl-penta-2,4-dienyl | H | iPr | H | H |

TABLE 1-continued

| Compound No | R⁸ | R⁴ᵃ | R⁴ᵇ | R⁴ᶜ | R⁴ᵈ |
|---|---|---|---|---|---|
| I-1099 | 4-isopropyloxycarbonylamino-cinnamyl | H | iPr | H | H |
| I-1100 | 3-naphthalen-2-yl-allyl | H | iPr | H | H |
| I-1101 | 3-(5-trifluoromethyl-pyridin-2-yl)-allyl | H | iPr | H | H |
| I-1102 | 3-(5-chloro-pyridin-2-yl)-allyl | H | iPr | H | H |
| I-1103 | 3-pyridin-4-yl-allyl | H | iPr | H | H |
| I-1104 | 3-(2-Chloro-pyridin-4-yl)-allyl | H | iPr | H | H |
| I-1105 | 4-chlorobenzyl | H | OCF₃ | H | H |
| I-1106 | Cinnamyl | H | OCF₃ | H | H |
| I-1107 | 4-chlorocinnamyl | H | OCF₃ | H | H |
| I-1108 | 4-fluorocinnamyl | H | OCF₃ | H | H |
| I-1109 | 4-bromocinnamyl | H | OCF₃ | H | H |
| I-1110 | 4-trifluoromethylcinnamyl | H | OCF₃ | H | H |
| I-1111 | 4-trifluoromethoxycinnamyl | H | OCF₃ | H | H |
| I-1112 | 4-pentafluoroethoxycinnamyl | H | OCF₃ | H | H |
| I-1113 | 4-methoxycinnamyl | H | OCF₃ | H | H |
| I-1114 | 4-ethoxycinnamyl | H | OCF₃ | H | H |
| I-1115 | 4-cyanocinnamyl | H | OCF₃ | H | H |
| I-1116 | 3-(6-chloro-pyridin-3-yl)-allyl | H | OCF₃ | H | H |
| I-1117 | 3-(4-chlorophenyl)-but-2-enyl | H | OCF₃ | H | H |
| I-1118 | 3-(4-chlorophenyl)-3-fluoro-allyl | H | OCF₃ | H | H |
| I-1119 | 3-chloro-4-fluoro-cinnamyl | H | OCF₃ | H | H |
| I-1120 | 3,5-dichloro-cinnamyl | H | OCF₃ | H | H |
| I-1121 | 5-phenyl-penta-2,4-dienyl | H | OCF₃ | H | H |
| I-1122 | 4-isopropyloxycarbonylamino-cinnamyl | H | OCF₃ | H | H |
| I-1123 | 3-naphthalen-2-yl-allyl | H | OCF₃ | H | H |
| I-1124 | 3-(5-trifluoromethyl-pyridin-2-yl)-allyl | H | OCF₃ | H | H |
| I-1125 | 3-(5-chloro-pyridin-2-yl)-allyl | H | OCF₃ | H | H |
| I-1126 | 3-pyridin-4-yl-allyl | H | OCF₃ | H | H |
| I-1127 | 3-(2-Chloro-pyridin-4-yl)-allyl | H | OCF₃ | H | H |

Table II provides 1127 compounds of formula Ib

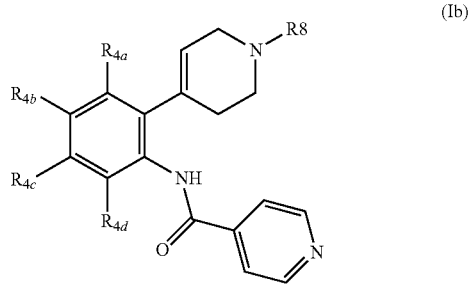

(Ib)

wherein the values of R⁸, R⁴ᵃ, R⁴ᵇ, R⁴ᶜ and R⁴ᵈ are given in Table 1.

Table III provides 1127 compounds of formula Ic

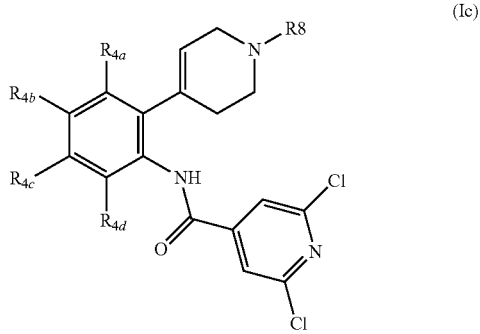

(Ic)

wherein the values of R⁸, R⁴ᵃ, R⁴ᵇ, R⁴ᶜ and R⁴ᵈ are given in Table 1

Table IV provides 1127 compounds of formula Id

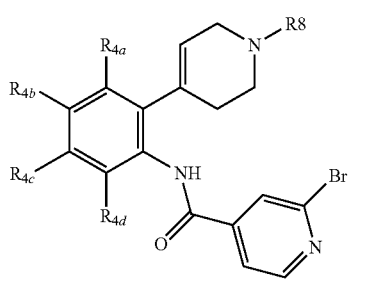

(Id)

wherein the values of R⁸, R⁴ᵃ, R⁴ᵇ, R⁴ᶜ and R⁴ᵈ are given in Table 1

Table V provides 1127 compounds of formula Ie

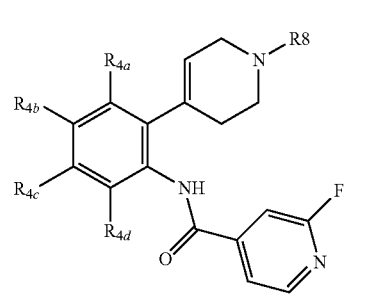

(Ie)

wherein and the values of R⁸, R⁴ᵃ, R⁴ᵇ, R⁴ᶜ and R⁴ᵈ are given in Table 1

Table VI provides 1127 compounds of formula If

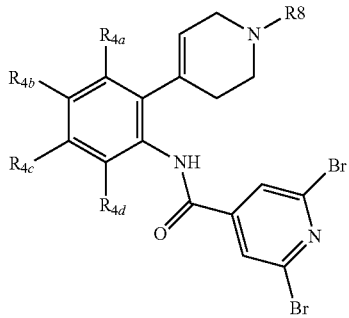

(If)

wherein the values of $R^8$, $R^{4a}$, $R^{4b}$, $R^{4c}$ and $R^{4d}$ are given in Table 1

Table VII provides 1127 compounds of formula Ig

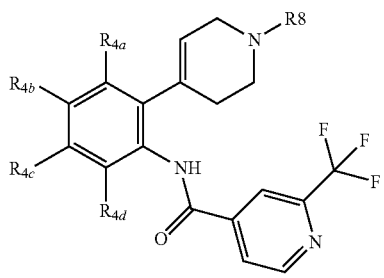

(Ig)

wherein the values of $R^8$, $R^{4a}$, $R^{4b}$, $R^{4c}$ and $R^{4d}$ are given in Table 1.

Table VIII provides 1127 compounds of formula Ih

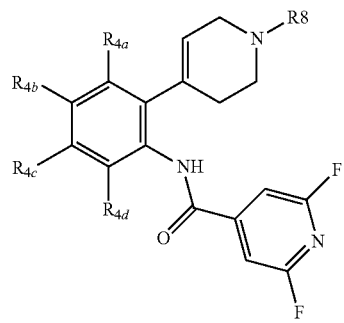

(Ih)

wherein the values of $R^8$, $R^{4a}$, $R^{4b}$, $R^{4c}$ and $R^{4d}$ are given in Table 1

Table IX provides 1127 compounds of formula Ii

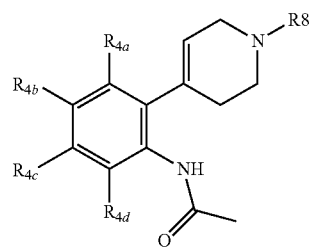

(Ii)

wherein the values of $R^8$, $R^{4a}$, $R^{4b}$, $R^{4c}$ and $R^{4d}$ are given in Table 1.

Table X provides 1127 compounds of formula Ij

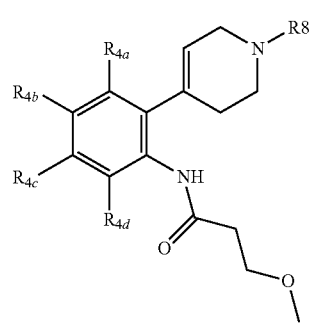

(Ij)

wherein the values of $R^8$, $R^{4a}$, $R^{4b}$, $R^{4c}$ and $R^{4d}$ are given in Table 1.

Table XI provides 1127 compounds of formula Ik

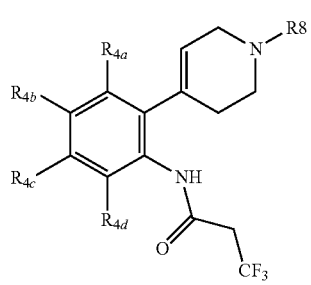

(Ik)

wherein the values of $R^8$, $R^{4a}$, $R^{4b}$, $R^{4c}$ and $R^{4d}$ are given in Table 1.

Table XII provides 1127 compounds of formula Il

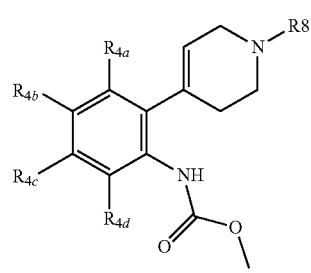

(Il)

wherein the values of $R^8$, $R^{4a}$, $R^{4b}$, $R^{4c}$ and $R^{4d}$ are given in Table 1.

Table XIII provides 1127 compounds of formula Im

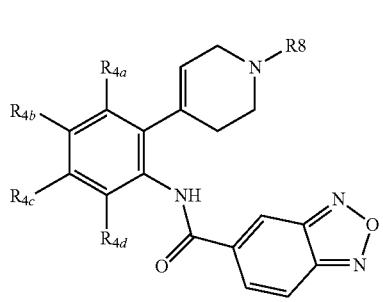

(Im)

wherein the values of $R^8$, $R^{4a}$, $R^{4b}$, $R^{4c}$ and $R^{4d}$ are given in Table 1.

Table XIV provides 1127 compounds of formula In

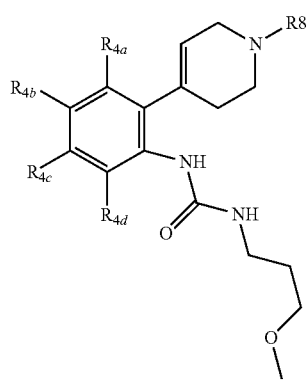

(In)

wherein the values of $R^8$, $R^{4a}$, $R^{4b}$, $R^{4c}$ and $R^{4d}$ are given in Table 1.

Table XV provides 1127 compounds of formula Io

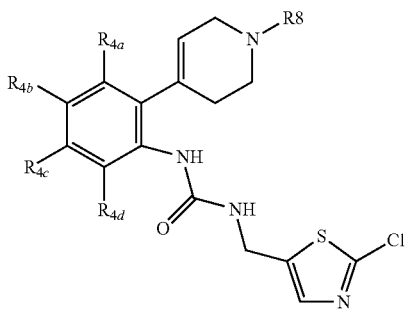

(Io)

wherein the values of $R^8$, $R^{4a}$, $R^{4b}$, $R^{4c}$ and $R^{4d}$ are given in Table 1.

Table XVI provides 1127 compounds of formula Ip

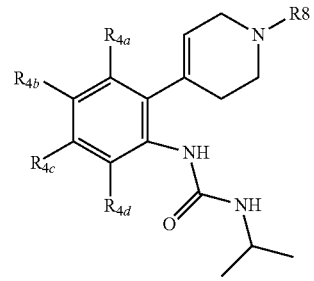

(Ip)

wherein the values of $R^8$, $R^{4a}$, $R^{4b}$, $R^{4c}$ and $R^{4d}$ are given in Table 1.

Table XVII provides 1127 compounds of formula Iq

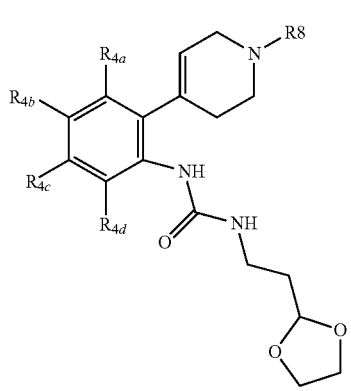

(Iq)

wherein the values of $R^8$, $R^{4a}$, $R^{4b}$, $R^{4c}$ and $R^{4d}$ are given in Table 1.

Table XVIII provides 1127 compounds of formula Ir

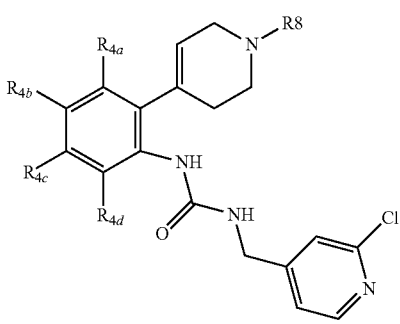

(Ir)

wherein the values of $R^8$, $R^{4a}$, $R^{4b}$, $R^{4c}$ and $R^{4d}$ are given in Table 1.

Table XIX provides 1127 compounds of formula Is

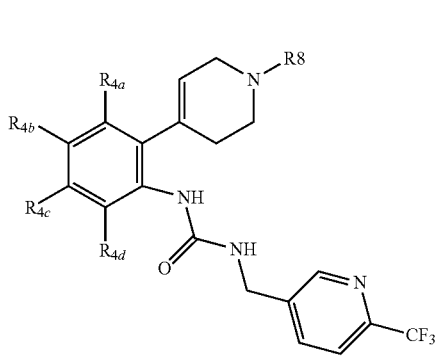
(Is)

wherein the values of $R^8$, $R^{4a}$, $R^{4b}$, $R^{4c}$ and $R^{4d}$ are given in Table 1.

Table XX provides 1127 compounds of formula It

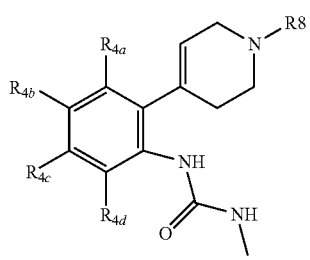
(It)

wherein the values of $R^8$, $R^{4a}$, $R^{4b}$, $R^{4c}$ and $R^{4d}$ are given in Table 1.

Table XXI provides 1127 compounds of formula Iu

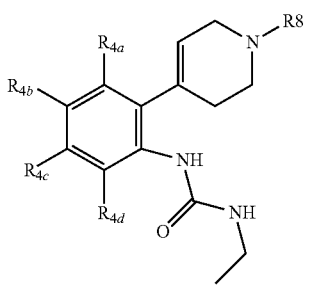
(Iu)

wherein the values of $R^8$, $R^{4a}$, $R^{4b}$, $R^{4c}$ and $R^{4d}$ are given in Table 1.

Table XXII provides 1127 compounds of formula Iv

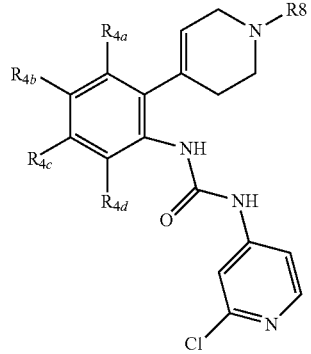
(Iv)

wherein the values of $R^8$, $R^{4a}$, $R^{4b}$, $R^{4c}$ and $R^{4d}$ are given in Table 1.

Table XXIII provides 1127 compounds of formula Iw

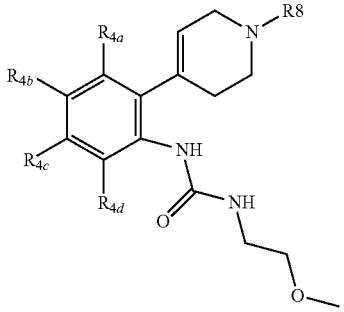
(Iw)

wherein the values of $R^8$, $R^{4a}$, $R^{4b}$, $R^{4c}$ and $R^{4d}$ are given in Table 1.

Table XXIV provides 1127 compounds of formula Ix

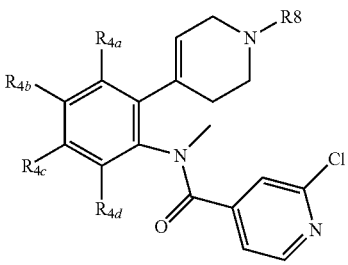
(Ix)

wherein the values of $R^8$, $R^{4a}$, $R^{4b}$, $R^{4c}$ and $R^{4d}$ are given in Table 1.

Table XXV provides 1127 compounds of formula Iaa

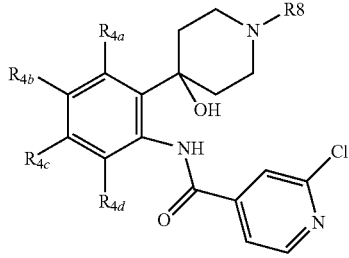
(Iaa)

wherein the values of $R^8$, $R^{4a}$, $R^{4b}$, $R^{4c}$ and $R^{4d}$ are given in Table 1.

Table XXVI provides 1127 compounds of formula Iab

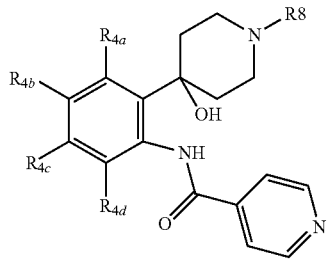
(Iab)

wherein the values of $R^8$, $R^{4a}$, $R^{4b}$, $R^{4c}$ and $R^{4d}$ are given in Table 1.

Table XXVII provides 1127 compounds of formula Iac

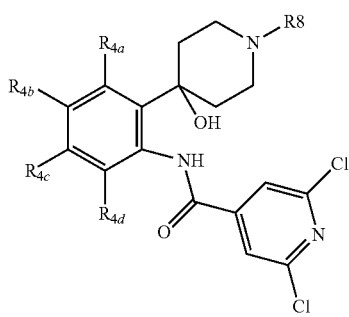
(Iac)

wherein the values of $R^8$, $R^{4a}$, $R^{4b}$, $R^{4c}$ and $R^{4d}$ are given in Table 1

Table XXVIII provides 1127 compounds of formula Iad

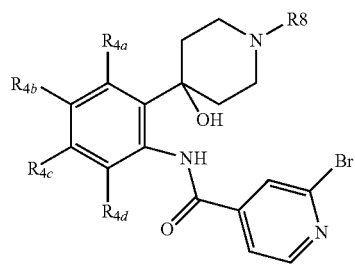
(Iad)

wherein the values of $R^8$, $R^{4a}$, $R^{4b}$, $R^{4c}$ and $R^{4d}$ are given in Table 1

Table XXIX provides 1127 compounds of formula Iae

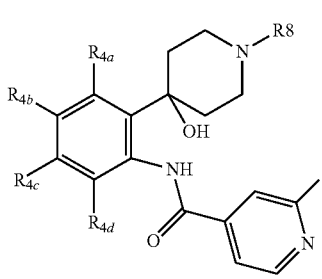
(Iae)

wherein and the values of $R^8$, $R^{4a}$, $R^{4b}$, $R^{4c}$ and $R^{4d}$ are given in Table 1

Table XXX provides 1127 compounds of formula Iaf

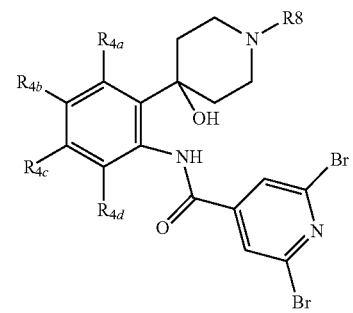
(Iaf)

wherein the values of $R^8$, $R^{4a}$, $R^{4b}$, $R^{4c}$ and $R^{4d}$ are given in Table 1

Table XXXI provides 1127 compounds of formula Iag

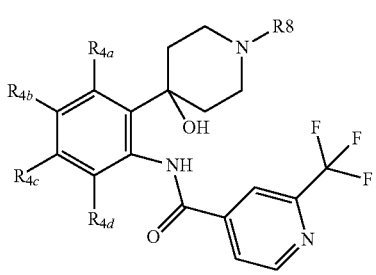
(Iag)

wherein the values of $R^8$, $R^{4a}$, $R^{4b}$, $R^{4c}$ and $R^{4d}$ are given in Table 1.

Table XXXII provides 1127 compounds of formula Iah

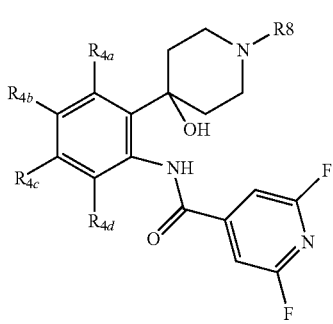
(Iah)

wherein the values of $R^8$, $R^{4a}$, $R^{4b}$, $R^{4c}$ and $R^{4d}$ are given in Table 1

Table XXXIII provides 1127 compounds of formula Iai

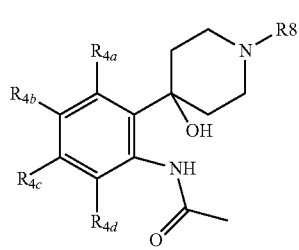
(Iai)

wherein the values of $R^8$, $R^{4a}$, $R^{4b}$, $R^{4c}$ and $R^{4d}$ are given in Table 1.

Table XXXIV provides 1127 compounds of formula Iaj

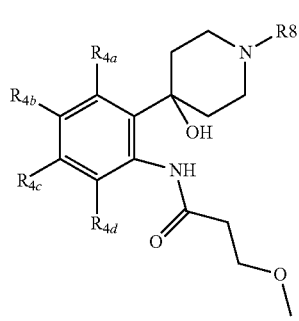
(Iaj)

wherein the values of $R^8$, $R^{4a}$, $R^{4b}$, $R^{4c}$ and $R^{4d}$ are given in Table 1.

Table XXXV provides 1127 compounds of formula Iak

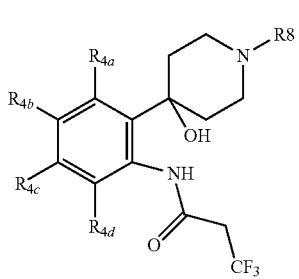
(Iak)

wherein the values of $R^8$, $R^{4a}$, $R^{4b}$, $R^{4c}$ and $R^{4d}$ are given in Table 1.

Table XXXVI provides 1127 compounds of formula Ial

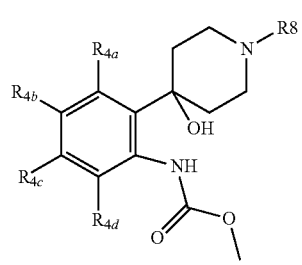
(Ial)

wherein the values of $R^8$, $R^{4a}$, $R^{4b}$, $R^{4c}$ and $R^{4d}$ are given in Table 1.

Table XXXVII provides 1127 compounds of formula Iam

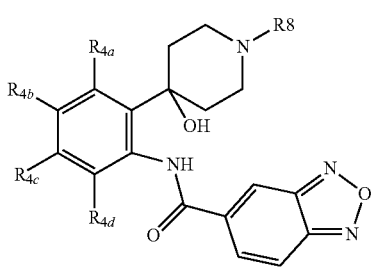
(Iam)

wherein the values of $R^8$, $R^{4a}$, $R^{4b}$, $R^{4c}$ and $R^{4d}$ are given in Table 1.

Table XXXVIII provides 1127 compounds of formula Ian

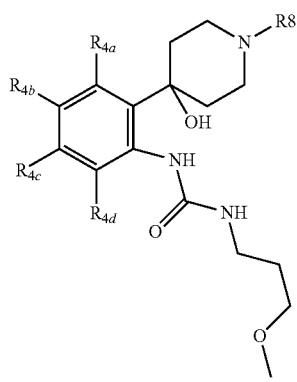
(Ian)

wherein the values of $R^8$, $R^{4a}$, $R^{4b}$, $R^{4c}$ and $R^{4d}$ are given in Table 1.

Table XXXIX provides 1127 compounds of formula Iao

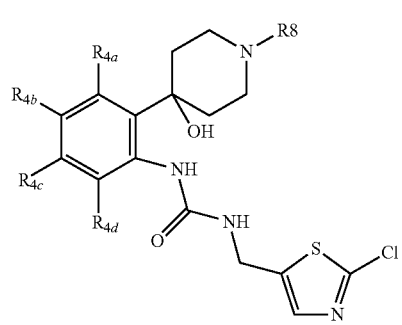
(Iao)

wherein the values of $R^8$, $R^{4a}$, $R^{4b}$, $R^{4c}$ and $R^{4d}$ are given in Table 1.

Table XL provides 1127 compounds of formula Iap

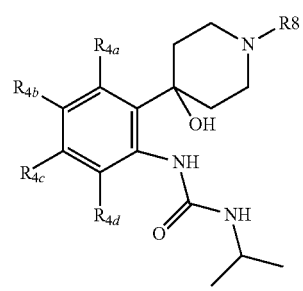 (Iap)

wherein the values of $R^8$, $R^{4a}$, $R^{4b}$, $R^{4c}$ and $R^{4d}$ are given in Table 1.

Table XLI provides 1127 compounds of formula Iaq

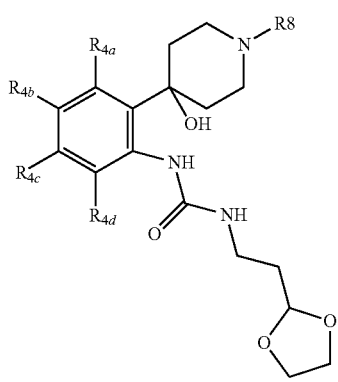 (Iaq)

wherein the values of $R^8$, $R^{4a}$, $R^{4b}$, $R^{4c}$ and $R^{4d}$ are given in Table 1.

Table XLII provides 1127 compounds of formula Iar

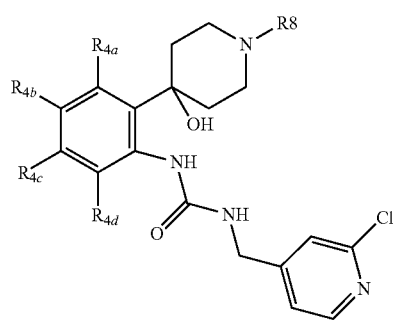 (Iar)

wherein the values of $R^8$, $R^{4a}$, $R^{4b}$, $R^{4c}$ and $R^{4d}$ are given in Table 1.

Table XLIII provides 1127 compounds of formula Ias

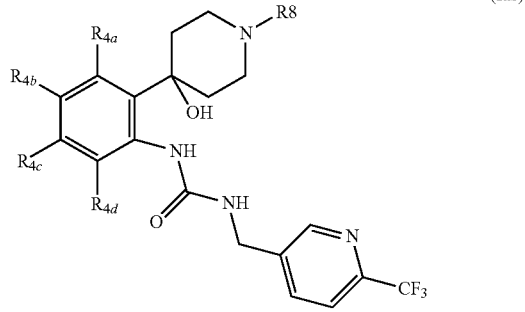 (Ias)

wherein the values of $R^8$, $R^{4a}$, $R^{4b}$, $R^{4c}$ and $R^{4d}$ are given in Table 1.

Table XLIV provides 1127 compounds of formula Iat

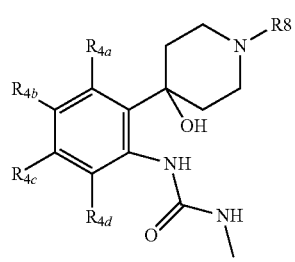 (Iat)

wherein the values of $R^8$, $R^{4a}$, $R^{4b}$, $R^{4c}$ and $R^{4d}$ are given in Table 1.

Table XLV provides 1127 compounds of formula Iau

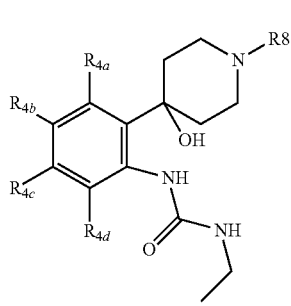 (Iau)

wherein the values of $R^8$, $R^{4a}$, $R^{4b}$, $R^{4c}$ and $R^{4d}$ are given in Table 1.

Table XLVI provides 1127 compounds of formula Iav

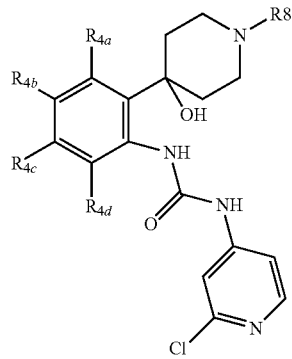
(Iav)

wherein the values of $R^8$, $R^{4a}$, $R^{4b}$, $R^{4c}$ and $R^{4d}$ are given in Table 1.

Table XLVII provides 1127 compounds of formula Iaw

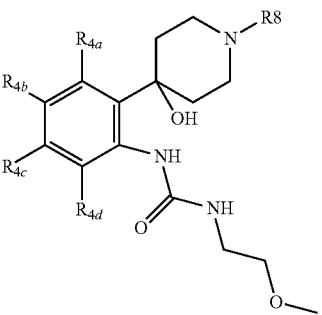
(Iaw)

wherein the values of $R^8$, $R^{4a}$, $R^{4b}$, $R^{4c}$ and $R^{4d}$ are given in Table 1.

Table XLVIII provides 1127 compounds of formula Iax

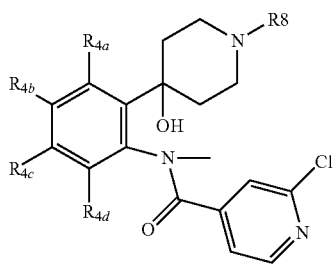
(Iax)

wherein the values of $R^8$, $R^{4a}$, $R^{4b}$, $R^{4c}$ and $R^{4d}$ are given in Table 1.

Table IL provides 1127 compounds of formula Iaaa

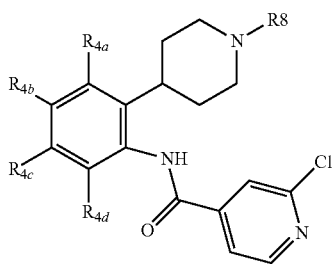
(Iaaa)

Table L provides 1127 compounds of formula Iaab

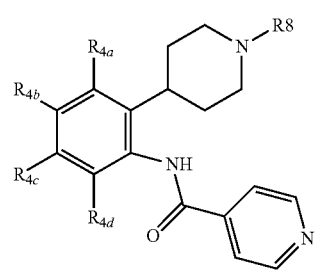
(Iaab)

wherein the values of $R^8$, $R^{4a}$, $R^{4b}$, $R^{4c}$ and $R^{4d}$ are given in Table 1.

Table LI provides 1127 compounds of formula Iaac

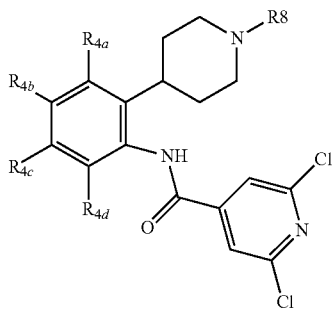
(Iaac)

wherein the values of $R^8$, $R^{4a}$, $R^{4b}$, $R^{4c}$ and $R^{4d}$ are given in Table 1

Table LII provides 1127 compounds of formula Iaad

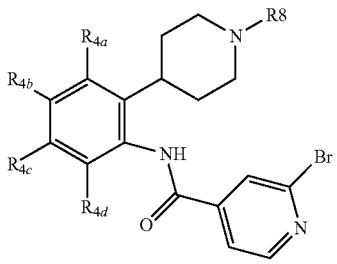
(Iaad)

wherein the values of $R^8$, $R^{4a}$, $R^{4b}$, $R^{4c}$ and $R^{4d}$ are given in Table 1

Table LIII provides 1127 compounds of formula Iaae

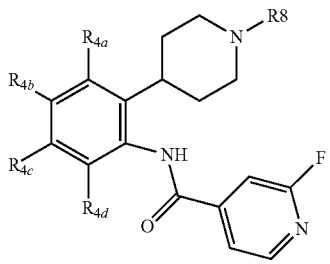
(Iaae)

wherein and the values of R$^8$, R$^{4a}$, R$^{4b}$, R$^{4c}$ and R$^{4d}$ are given in Table I Table LIV provides 1127 compounds of formula Iaaf

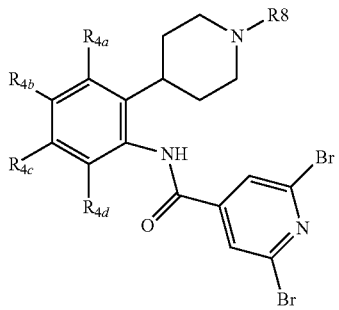
(Iaaf)

wherein the values of R$^8$, R$^{4a}$, R$^{4b}$, R$^{4c}$ and R$^{4d}$ are given in Table 1

Table LV provides 1127 compounds of formula Iaag

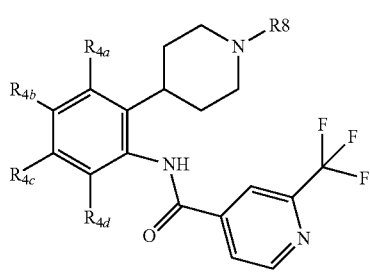
(Iaag)

wherein the values of R$^8$, R$^{4a}$, R$^{4b}$, R$^{4c}$ and R$^{4d}$ are given in Table 1.

Table LVI provides 1127 compounds of formula Iaah

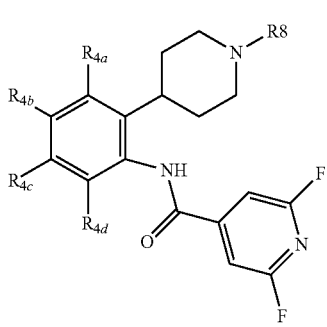
(Iaah)

wherein the values of R$^8$, R$^{4a}$, R$^{4b}$, R$^{4c}$ and R$^{4d}$ are given in Table 1

Table LVII provides 1127 compounds of formula Iaai

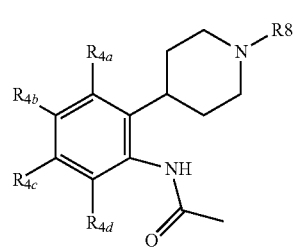
(Iaai)

wherein the values of R$^8$, R$^{4a}$, R$^{4b}$, R$^{4c}$ and R$^{4d}$ are given in Table 1.

Table LVIII provides 1127 compounds of formula Iaaj

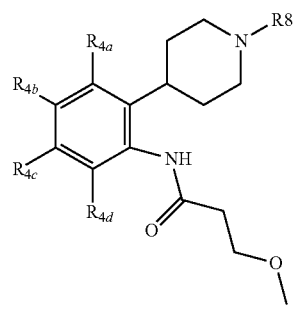
(Iaaj)

wherein the values of R$^8$, R$^{4a}$, R$^{4b}$, R$^{4c}$ and R$^{4d}$ are given in Table 1.

Table LIX provides 1127 compounds of formula Iaak

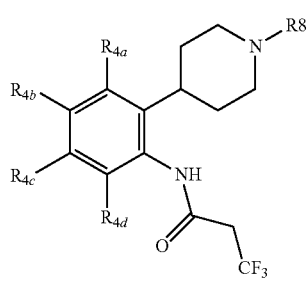
(Iaak)

wherein the values of R$^8$, R$^{4a}$, R$^{4b}$, R$^{4c}$ and R$^{4d}$ are given in Table 1.

Table LX provides 1127 compounds of formula Iaal

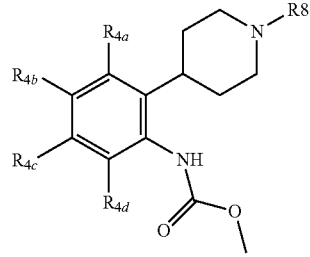
(Iaal)

wherein the values of $R^8$, $R^{4a}$, $R^{4b}$, $R^{4c}$ and $R^{4d}$ are given in Table 1.

Table LXI provides 1127 compounds of formula Iaam

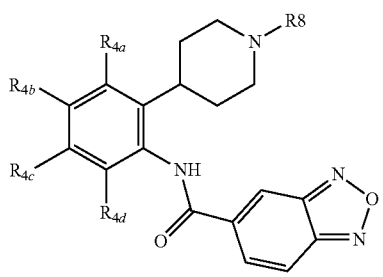
(Iaam)

wherein the values of $R^8$, $R^{4a}$, $R^{4b}$, $R^{4c}$ and $R^{4d}$ are given in Table 1.

Table LXII provides 1127 compounds of formula Iaan

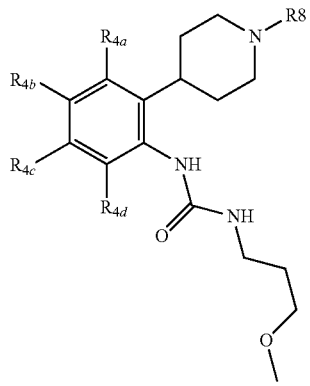
(Iaan)

wherein the values of $R^8$, $R^{4a}$, $R^{4b}$, $R^{4c}$ and $R^{4d}$ are given in Table 1.

Table LXIII provides 1127 compounds of formula Iaao

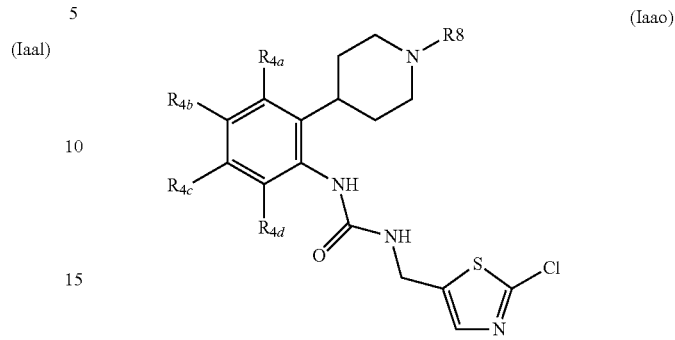
(Iaao)

wherein the values of $R^8$, $R^{4a}$, $R^{4b}$, $R^{4c}$ and $R^{4d}$ are given in Table 1.

Table LXIV provides 1127 compounds of formula Iaap

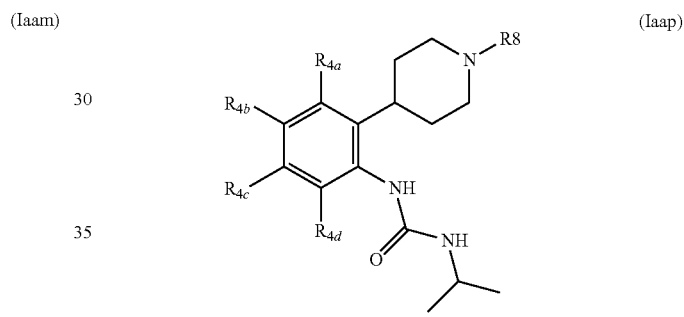
(Iaap)

wherein the values of $R^8$, $R^{4a}$, $R^{4b}$, $R^{4c}$ and $R^{4d}$ are given in Table 1.

Table LXV provides 1127 compounds of formula Iaaq

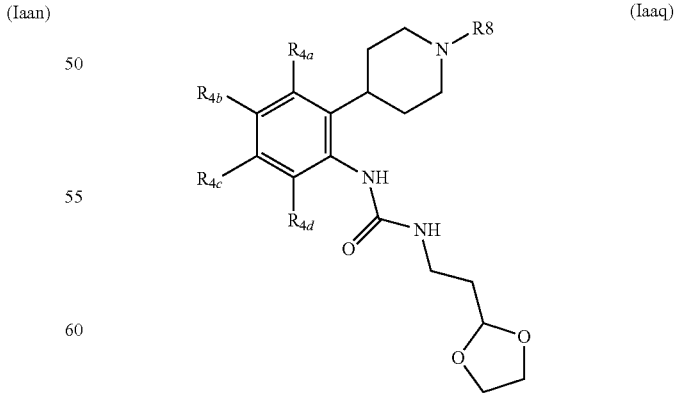
(Iaaq)

wherein the values of $R^8$, $R^{4a}$, $R^{4b}$, $R^{4c}$ and $R^{4d}$ are given in Table 1.

Table LXVI provides 1127 compounds of formula Iaar

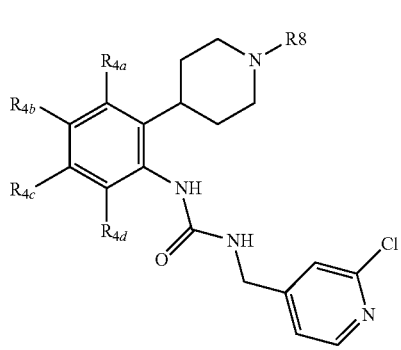
(Iaar)

wherein the values of R$^8$, R$^{4a}$, R$^{4b}$, R$^{4c}$ and R$^{4d}$ are given in Table 1.

Table LXVII provides 1127 compounds of formula Iaas

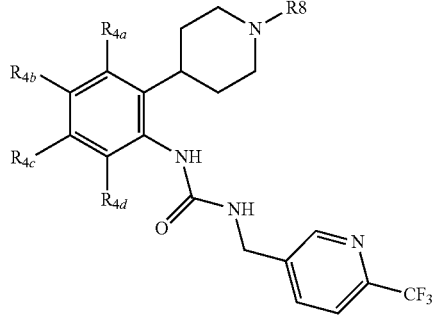
(Iaas)

wherein the values of R$^8$, R$^{4a}$, R$^{4b}$, R$^{4c}$ and R$^{4d}$ are given in Table 1.

Table LXVIII provides 1127 compounds of formula Iaat

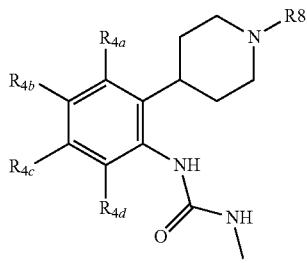
(Iaat)

wherein the values of R$^8$, R$^{4a}$, R$^{4b}$, R$^{4c}$ and R$^{4d}$ are given in Table 1.

Table LXIX provides 1127 compounds of formula Iaau

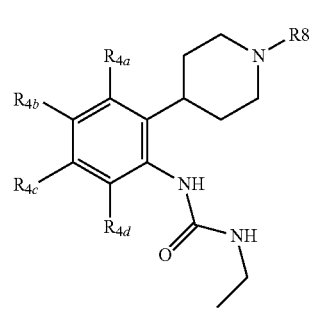
(Iaau)

wherein the values of R$^8$, R$^{4a}$, R$^{4b}$, R$^{4c}$ and R$^{4d}$ are given in Table 1.

Table LXX provides 1127 compounds of formula Iaav

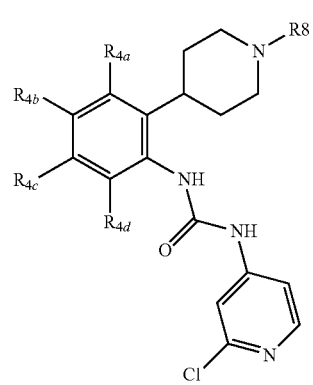
(Iaav)

wherein the values of R$^8$, R$^{4a}$, R$^{4b}$, R$^{4c}$ and R$^{4d}$ are given in Table I.

Table LXXI provides 1127 compounds of formula Iaaw

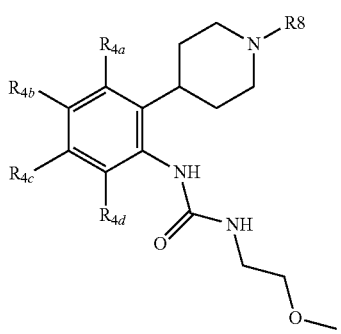
(Iaaw)

wherein the values of R$^8$, R$^{4a}$, R$^{4b}$, R$^{4c}$ and R$^{4d}$ are given in Table 1.

Table LXXII provides 1127 compounds of formula Iaax

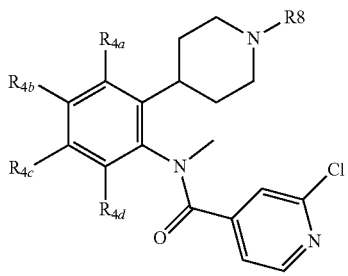

(Iaax)

wherein the values of $R^8$, $R^{4a}$, $R^{4b}$, $R^{4c}$ and $R^{4d}$ are given in Table 1.

Table LXXIII provides 506 compounds of formula Iy

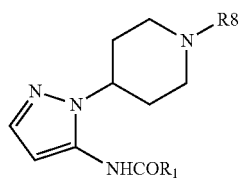

(Iy)

wherein the values of $R^8$ and $R^1$ are given in Table 73.

TABLE 73

| Compound No | $R^8$ | R1 |
|---|---|---|
| LXXIII-1 | Cinnamyl | 2-chloro-pyrid-4-yl |
| LXXIII-2 | 4-chlorocinnamyl | 2-chloro-pyrid-4-yl |
| LXXIII-3 | 4-fluorocinnamyl | 2-chloro-pyrid-4-yl |
| LXXIII-4 | 4-bromocinnamyl | 2-chloro-pyrid-4-yl |
| LXXIII-5 | 4-trifluoromethylcinnamyl | 2-chloro-pyrid-4-yl |
| LXXIII-6 | 4-trifluoromethoxycinnamyl | 2-chloro-pyrid-4-yl |
| LXXIII-7 | 4-pentafluoroethoxycinnamyl | 2-chloro-pyrid-4-yl |
| LXXIII-8 | 4-methoxycinnamyl | 2-chloro-pyrid-4-yl |
| LXXIII-9 | 4-ethoxycinnamyl | 2-chloro-pyrid-4-yl |
| LXXIII-10 | 4-cyanocinnamyl | 2-chloro-pyrid-4-yl |
| LXXIII-11 | 3-(6-chloro-pyridin-3-yl)-allyl | 2-chloro-pyrid-4-yl |
| LXXIII-12 | 3-(4-chlorophenyl)-but-2-enyl | 2-chloro-pyrid-4-yl |
| LXXIII-13 | 3-(4-chlorophenyl)-3-fluoro-allyl | 2-chloro-pyrid-4-yl |
| LXXIII-14 | 3-chloro-4-fluoro-cinnamyl | 2-chloro-pyrid-4-yl |
| LXXIII-15 | 3,5-dichloro-cinnamyl | 2-chloro-pyrid-4-yl |
| LXXIII-16 | 5-phenyl-penta-2,4-dienyl | 2-chloro-pyrid-4-yl |
| LXXIII-17 | 4-isopropyloxycarbonylamino-cinnamyl | 2-chloro-pyrid-4-yl |
| LXXIII-18 | 3-naphthalen-2-yl-allyl | 2-chloro-pyrid-4-yl |
| LXXIII-19 | 3-(5-trifluoromethyl-pyridin-2-yl)-allyl | 2-chloro-pyrid-4-yl |
| LXXIII-20 | 3-(5-chloro-pyridin-2-yl)-allyl | 2-chloro-pyrid-4-yl |
| LXXIII-21 | 3-pyridin-4-yl-allyl | 2-chloro-pyrid-4-yl |
| LXXIII-22 | 3-(2-Chloro-pyridin-4-yl)-allyl | 2-chloro-pyrid-4-yl |
| LXXIII-23 | Cinnamyl | pyrid-4-yl |
| LXXIII-24 | 4-chlorocinnamyl | pyrid-4-yl |
| LXXIII-25 | 4-fluorocinnamyl | pyrid-4-yl |
| LXXIII-26 | 4-bromocinnamyl | pyrid-4-yl |
| LXXIII-27 | 4-trifluoromethylcinnamyl | pyrid-4-yl |
| LXXIII-28 | 4-trifluoromethoxycinnamyl | pyrid-4-yl |
| LXXIII-29 | 4-pentafluoroethoxycinnamyl | pyrid-4-yl |
| LXXIII-30 | 4-methoxycinnamyl | pyrid-4-yl |
| LXXIII-31 | 4-ethoxycinnamyl | pyrid-4-yl |
| LXXIII-32 | 4-cyanocinnamyl | pyrid-4-yl |
| LXXIII-33 | 3-(6-chloro-pyridin-3-yl)-allyl | pyrid-4-yl |
| LXXIII-34 | 3-(4-chlorophenyl)-but-2-enyl | pyrid-4-yl |
| LXXIII-35 | 3-(4-chlorophenyl)-3-fluoro-allyl | pyrid-4-yl |
| LXXIII-36 | 3-chloro-4-fluoro-cinnamyl | pyrid-4-yl |
| LXXIII-37 | 3,5-dichloro-cinnamyl | pyrid-4-yl |
| LXXIII-38 | 5-phenyl-penta-2,4-dienyl | pyrid-4-yl |
| LXXIII-39 | 4-isopropyloxycarbonylamino-cinnamyl | pyrid-4-yl |
| LXXIII-40 | 3-naphthalen-2-yl-allyl | pyrid-4-yl |
| LXXIII-41 | 3-(5-trifluoromethyl-pyridin-2-yl)-allyl | pyrid-4-yl |
| LXXIII-42 | 3-(5-chloro-pyridin-2-yl)-allyl | pyrid-4-yl |
| LXXIII-43 | 3-pyridin-4-yl-allyl | pyrid-4-yl |
| LXXIII-44 | 3-(2-Chloro-pyridin-4-yl)-allyl | pyrid-4-yl |
| LXXIII-45 | Cinnamyl | 2,6-dichloro-pyrid-4-yl |
| LXXIII-46 | 4-chlorocinnamyl | 2,6-dichloro-pyrid-4-yl |
| LXXIII-47 | 4-fluorocinnamyl | 2,6-dichloro-pyrid-4-yl |
| LXXIII-48 | 4-bromocinnamyl | 2,6-dichloro-pyrid-4-yl |
| LXXIII-49 | 4-trifluoromethylcinnamyl | 2,6-dichloro-pyrid-4-yl |
| LXXIII-50 | 4-trifluoromethoxycinnamyl | 2,6-dichloro-pyrid-4-yl |
| LXXIII-51 | 4-pentafluoroethoxycinnamyl | 2,6-dichloro-pyrid-4-yl |
| LXXIII-52 | 4-methoxycinnamyl | 2,6-dichloro-pyrid-4-yl |
| LXXIII-53 | 4-ethoxycinnamyl | 2,6-dichloro-pyrid-4-yl |
| LXXIII-54 | 4-cyanocinnamyl | 2,6-dichloro-pyrid-4-yl |
| LXXIII-55 | 3-(6-chloro-pyridin-3-yl)-allyl | 2,6-dichloro-pyrid-4-yl |
| LXXIII-56 | 3-(4-chlorophenyl)-but-2-enyl | 2,6-dichloro-pyrid-4-yl |
| LXXIII-57 | 3-(4-chlorophenyl)-3-fluoro-allyl | 2,6-dichloro-pyrid-4-yl |

TABLE 73-continued

| Compound No | R8 | R1 |
|---|---|---|
| LXXIII-58 | 3-chloro-4-fluoro-cinnamyl | 2,6-dichloro-pyrid-4-yl |
| LXXIII-59 | 3,5-dichloro-cinnamyl | 2,6-dichloro-pyrid-4-yl |
| LXXIII-60 | 5-phenyl-penta-2,4-dienyl | 2,6-dichloro-pyrid-4-yl |
| LXXIII-61 | 4-isopropyloxycarbonylamino-cinnamyl | 2,6-dichloro-pyrid-4-yl |
| LXXIII-62 | 3-naphthalen-2-yl-allyl | 2,6-dichloro-pyrid-4-yl |
| LXXIII-63 | 3-(5-trifluoromethyl-pyridin-2-yl)-allyl | 2,6-dichloro-pyrid-4-yl |
| LXXIII-64 | 3-(5-chloro-pyridin-2-yl)-allyl | 2,6-dichloro-pyrid-4-yl |
| LXXIII-65 | 3-pyridin-4-yl-allyl | 2,6-dichloro-pyrid-4-yl |
| LXXIII-66 | 3-(2-Chloro-pyridin-4-yl)-allyl | 2,6-dichloro-pyrid-4-yl |
| LXXIII-67 | Cinnamyl | 2-bromo-pyrid-4-yl |
| LXXIII-68 | 4-chlorocinnamyl | 2-bromo-pyrid-4-yl |
| LXXIII-69 | 4-fluorocinnamyl | 2-bromo-pyrid-4-yl |
| LXXIII-70 | 4-bromocinnamyl | 2-bromo-pyrid-4-yl |
| LXXIII-71 | 4-trifluoromethylcinnamyl | 2-bromo-pyrid-4-yl |
| LXXIII-72 | 4-trifluoromethoxycinnamyl | 2-bromo-pyrid-4-yl |
| LXXIII-73 | 4-pentafluoroethoxycinnamyl | 2-bromo-pyrid-4-yl |
| LXXIII-74 | 4-methoxycinnamyl | 2-bromo-pyrid-4-yl |
| LXXIII-75 | 4-ethoxycinnamyl | 2-bromo-pyrid-4-yl |
| LXXIII-76 | 4-cyanocinnamyl | 2-bromo-pyrid-4-yl |
| LXXIII-77 | 3-(6-chloro-pyridin-3-yl)-allyl | 2-bromo-pyrid-4-yl |
| LXXIII-78 | 3-(4-chlorophenyl)-but-2-enyl | 2-bromo-pyrid-4-yl |
| LXXIII-79 | 3-(4-chlorophenyl)-3-fluoro-allyl | 2-bromo-pyrid-4-yl |
| LXXIII-80 | 3-chloro-4-fluoro-cinnamyl | 2-bromo-pyrid-4-yl |
| LXXIII-81 | 3,5-dichloro-cinnamyl | 2-bromo-pyrid-4-yl |
| LXXIII-82 | 5-phenyl-penta-2,4-dienyl | 2-bromo-pyrid-4-yl |
| LXXIII-83 | 4-isopropyloxycarbonylamino-cinnamyl | 2-bromo-pyrid-4-yl |
| LXXIII-84 | 3-naphthalen-2-yl-allyl | 2-bromo-pyrid-4-yl |
| LXXIII-85 | 3-(5-trifluoromethyl-pyridin-2-yl)-allyl | 2-bromo-pyrid-4-yl |
| LXXIII-86 | 3-(5-chloro-pyridin-2-yl)-allyl | 2-bromo-pyrid-4-yl |
| LXXIII-87 | 3-pyridin-4-yl-allyl | 2-bromo-pyrid-4-yl |
| LXXIII-88 | 3-(2-Chloro-pyridin-4-yl)-allyl | 2-bromo-pyrid-4-yl |
| LXXIII-89 | Cinnamyl | 2-fluoro-pyrid-4-yl |
| LXXIII-90 | 4-chlorocinnamyl | 2-fluoro-pyrid-4-yl |
| LXXIII-91 | 4-fluorocinnamyl | 2-fluoro-pyrid-4-yl |
| LXXIII-92 | 4-bromocinnamyl | 2-fluoro-pyrid-4-yl |
| LXXIII-93 | 4-trifluoromethylcinnamyl | 2-fluoro-pyrid-4-yl |
| LXXIII-94 | 4-trifluoromethoxycinnamyl | 2-fluoro-pyrid-4-yl |
| LXXIII-95 | 4-pentafluoroethoxycinnamyl | 2-fluoro-pyrid-4-yl |
| LXXIII-96 | 4-methoxycinnamyl | 2-fluoro-pyrid-4-yl |
| LXXIII-97 | 4-ethoxycinnamyl | 2-fluoro-pyrid-4-yl |
| LXXIII-98 | 4-cyanocinnamyl | 2-fluoro-pyrid-4-yl |
| LXXIII-99 | 3-(6-chloro-pyridin-3-yl)-allyl | 2-fluoro-pyrid-4-yl |
| LXXIII-100 | 3-(4-chlorophenyl)-but-2-enyl | 2-fluoro-pyrid-4-yl |
| LXXIII-101 | 3-(4-chlorophenyl)-3-fluoro-allyl | 2-fluoro-pyrid-4-yl |
| LXXIII-102 | 3-chloro-4-fluoro-cinnamyl | 2-fluoro-pyrid-4-yl |
| LXXIII-103 | 3,5-dichloro-cinnamyl | 2-fluoro-pyrid-4-yl |
| LXXIII-104 | 5-phenyl-penta-2,4-dienyl | 2-fluoro-pyrid-4-yl |
| LXXIII-105 | 4-isopropyloxycarbonylamino-cinnamyl | 2-fluoro-pyrid-4-yl |
| LXXIII-106 | 3-naphthalen-2-yl-allyl | 2-fluoro-pyrid-4-yl |
| LXXIII-107 | 3-(5-trifluoromethyl-pyridin-2-yl)-allyl | 2-fluoro-pyrid-4-yl |
| LXXIII-108 | 3-(5-chloro-pyridin-2-yl)-allyl | 2-fluoro-pyrid-4-yl |
| LXXIII-109 | 3-pyridin-4-yl-allyl | 2-fluoro-pyrid-4-yl |
| LXXIII-110 | 3-(2-Chloro-pyridin-4-yl)-allyl | 2-fluoro-pyrid-4-yl |
| LXXIII-111 | Cinnamyl | 2,6-dibromo-pyrid-4-yl |
| LXXIII-112 | 4-chlorocinnamyl | 2,6-dibromo-pyrid-4-yl |
| LXXIII-113 | 4-fluorocinnamyl | 2,6-dibromo-pyrid-4-yl |
| LXXIII-114 | 4-bromocinnamyl | 2,6-dibromo-pyrid-4-yl |
| LXXIII-115 | 4-trifluoromethylcinnamyl | 2,6-dibromo-pyrid-4-yl |
| LXXIII-116 | 4-trifluoromethoxycinnamyl | 2,6-dibromo-pyrid-4-yl |
| LXXIII-117 | 4-pentafluoroethoxycinnamyl | 2,6-dibromo-pyrid-4-yl |
| LXXIII-118 | 4-methoxycinnamyl | 2,6-dibromo-pyrid-4-yl |
| LXXIII-119 | 4-ethoxycinnamyl | 2,6-dibromo-pyrid-4-yl |
| LXXIII-120 | 4-cyanocinnamyl | 2,6-dibromo-pyrid-4-yl |
| LXXIII-121 | 3-(6-chloro-pyridin-3-yl)-allyl | 2,6-dibromo-pyrid-4-yl |
| LXXIII-122 | 3-(4-chlorophenyl)-but-2-enyl | 2,6-dibromo-pyrid-4-yl |
| LXXIII-123 | 3-(4-chlorophenyl)-3-fluoro-allyl | 2,6-dibromo-pyrid-4-yl |
| LXXIII-124 | 3-chloro-4-fluoro-cinnamyl | 2,6-dibromo-pyrid-4-yl |
| LXXIII-125 | 3,5-dichloro-cinnamyl | 2,6-dibromo-pyrid-4-yl |
| LXXIII-126 | 5-phenyl-penta-2,4-dienyl | 2,6-dibromo-pyrid-4-yl |
| LXXIII-127 | 4-isopropyloxycarbonylamino-cinnamyl | 2,6-dibromo-pyrid-4-yl |
| LXXIII-128 | 3-naphthalen-2-yl-allyl | 2,6-dibromo-pyrid-4-yl |
| LXXIII-129 | 3-(5-trifluoromethyl-pyridin-2-yl)-allyl | 2,6-dibromo-pyrid-4-yl |
| LXXIII-130 | 3-(5-chloro-pyridin-2-yl)-allyl | 2,6-dibromo-pyrid-4-yl |
| LXXIII-131 | 3-pyridin-4-yl-allyl | 2,6-dibromo-pyrid-4-yl |
| LXXIII-132 | 3-(2-Chloro-pyridin-4-yl)-allyl | 2,6-dibromo-pyrid-4-yl |
| LXXIII-133 | Cinnamyl | 2-trifluoromethyl-pyrid-4-yl |
| LXXIII-134 | 4-chlorocinnamyl | 2-trifluoromethyl-pyrid-4-yl |
| LXXIII-135 | 4-fluorocinnamyl | 2-trifluoromethyl-pyrid-4-yl |

TABLE 73-continued

| Compound No | R8 | R1 |
|---|---|---|
| LXXIII-136 | 4-bromocinnamyl | 2-trifluoromethyl-pyrid-4-yl |
| LXXIII-137 | 4-trifluoromethylcinnamyl | 2-trifluoromethyl-pyrid-4-yl |
| LXXIII-138 | 4-trifluoromethoxycinnamyl | 2-trifluoromethyl-pyrid-4-yl |
| LXXIII-139 | 4-pentafluoroethoxycinnamyl | 2-trifluoromethyl-pyrid-4-yl |
| LXXIII-140 | 4-methoxycinnamyl | 2-trifluoromethyl-pyrid-4-yl |
| LXXIII-141 | 4-ethoxycinnamyl | 2-trifluoromethyl-pyrid-4-yl |
| LXXIII-142 | 4-cyanocinnamyl | 2-trifluoromethyl-pyrid-4-yl |
| LXXIII-143 | 3-(6-chloro-pyridin-3-yl)-allyl | 2-trifluoromethyl-pyrid-4-yl |
| LXXIII-144 | 3-(4-chlorophenyl)-but-2-enyl | 2-trifluoromethyl-pyrid-4-yl |
| LXXIII-145 | 3-(4-chlorophenyl)-3-fluoro-allyl | 2-trifluoromethyl-pyrid-4-yl |
| LXXIII-146 | 3-chloro-4-fluoro-cinnamyl | 2-trifluoromethyl-pyrid-4-yl |
| LXXIII-147 | 3,5-dichloro-cinnamyl | 2-trifluoromethyl-pyrid-4-yl |
| LXXIII-148 | 5-phenyl-penta-2,4-dienyl | 2-trifluoromethyl-pyrid-4-yl |
| LXXIII-149 | 4-isopropyloxycarbonylamino-cinnamyl | 2-trifluoromethyl-pyrid-4-yl |
| LXXIII-150 | 3-naphthalen-2-yl-allyl | 2-trifluoromethyl-pyrid-4-yl |
| LXXIII-151 | 3-(5-trifluoromethyl-pyridin-2-yl)-allyl | 2-trifluoromethyl-pyrid-4-yl |
| LXXIII-152 | 3-(5-chloro-pyridin-2-yl)-allyl | 2-trifluoromethyl-pyrid-4-yl |
| LXXIII-153 | 3-pyridin-4-yl-allyl | 2-trifluoromethyl-pyrid-4-yl |
| LXXIII-154 | 3-(2-Chloro-pyridin-4-yl)-allyl | 2-trifluoromethyl-pyrid-4-yl |
| LXXIII-155 | Cinnamyl | 2,6-difluoro-pyrid-4-yl |
| LXXIII-156 | 4-chlorocinnamyl | 2,6-difluoro-pyrid-4-yl |
| LXXIII-157 | 4-fluorocinnamyl | 2,6-difluoro-pyrid-4-yl |
| LXXIII-158 | 4-bromocinnamyl | 2,6-difluoro-pyrid-4-yl |
| LXXIII-159 | 4-trifluoromethylcinnamyl | 2,6-difluoro-pyrid-4-yl |
| LXXIII-160 | 4-trifluoromethoxycinnamyl | 2,6-difluoro-pyrid-4-yl |
| LXXIII-161 | 4-pentafluoroethoxycinnamyl | 2,6-difluoro-pyrid-4-yl |
| LXXIII-162 | 4-methoxycinnamyl | 2,6-difluoro-pyrid-4-yl |
| LXXIII-163 | 4-ethoxycinnamyl | 2,6-difluoro-pyrid-4-yl |
| LXXIII-164 | 4-cyanocinnamyl | 2,6-difluoro-pyrid-4-yl |
| LXXIII-165 | 3-(6-chloro-pyridin-3-yl)-allyl | 2,6-difluoro-pyrid-4-yl |
| LXXIII-166 | 3-(4-chlorophenyl)-but-2-enyl | 2,6-difluoro-pyrid-4-yl |
| LXXIII-167 | 3-(4-chlorophenyl)-3-fluoro-allyl | 2,6-difluoro-pyrid-4-yl |
| LXXIII-168 | 3-chloro-4-fluoro-cinnamyl | 2,6-difluoro-pyrid-4-yl |
| LXXIII-169 | 3,5-dichloro-cinnamyl | 2,6-difluoro-pyrid-4-yl |
| LXXIII-170 | 5-phenyl-penta-2,4-dienyl | 2,6-difluoro-pyrid-4-yl |
| LXXIII-171 | 4-isopropyloxycarbonylamino-cinnamyl | 2,6-difluoro-pyrid-4-yl |
| LXXIII-172 | 3-naphthalen-2-yl-allyl | 2,6-difluoro-pyrid-4-yl |
| LXXIII-173 | 3-(5-trifluoromethyl-pyridin-2-yl)-allyl | 2,6-difluoro-pyrid-4-yl |
| LXXIII-174 | 3-(5-chloro-pyridin-2-yl)-allyl | 2,6-difluoro-pyrid-4-yl |
| LXXIII-175 | 3-pyridin-4-yl-allyl | 2,6-difluoro-pyrid-4-yl |
| LXXIII-176 | 3-(2-Chloro-pyridin-4-yl)-allyl | 2,6-difluoro-pyrid-4-yl |
| LXXIII-177 | Cinnamyl | methyl |
| LXXIII-178 | 4-chlorocinnamyl | methyl |
| LXXIII-179 | 4-fluorocinnamyl | methyl |
| LXXIII-180 | 4-bromocinnamyl | methyl |
| LXXIII-181 | 4-trifluoromethylcinnamyl | methyl |
| LXXIII-182 | 4-trifluoromethoxycinnamyl | methyl |
| LXXIII-183 | 4-pentafluoroethoxycinnamyl | methyl |
| LXXIII-184 | 4-methoxycinnamyl | methyl |
| LXXIII-185 | 4-ethoxycinnamyl | methyl |
| LXXIII-186 | 4-cyanocinnamyl | methyl |
| LXXIII-187 | 3-(6-chloro-pyridin-3-yl)-allyl | methyl |
| LXXIII-188 | 3-(4-chlorophenyl)-but-2-enyl | methyl |
| LXXIII-189 | 3-(4-chlorophenyl)-3-fluoro-allyl | methyl |
| LXXIII-190 | 3-chloro-4-fluoro-cinnamyl | methyl |
| LXXIII-191 | 3,5-dichloro-cinnamyl | methyl |
| LXXIII-192 | 5-phenyl-penta-2,4-dienyl | methyl |
| LXXIII-193 | 4-isopropyloxycarbonylamino-cinnamyl | methyl |
| LXXIII-194 | 3-naphthalen-2-yl-allyl | methyl |
| LXXIII-195 | 3-(5-trifluoromethyl-pyridin-2-yl)-allyl | methyl |
| LXXIII-196 | 3-(5-chloro-pyridin-2-yl)-allyl | methyl |
| LXXIII-197 | 3-pyridin-4-yl-allyl | methyl |
| LXXIII-198 | 3-(2-Chloro-pyridin-4-yl)-allyl | methyl |
| LXXIII-199 | Cinnamyl | methoxyethyl |
| LXXIII-200 | 4-chlorocinnamyl | methoxyethyl |
| LXXIII-201 | 4-fluorocinnamyl | methoxyethyl |
| LXXIII-202 | 4-bromocinnamyl | methoxyethyl |
| LXXIII-203 | 4-trifluoromethylcinnamyl | methoxyethyl |
| LXXIII-204 | 4-trifluoromethoxycinnamyl | methoxyethyl |
| LXXIII-205 | 4-pentafluoroethoxycinnamyl | methoxyethyl |
| LXXIII-206 | 4-methoxycinnamyl | methoxyethyl |
| LXXIII-207 | 4-ethoxycinnamyl | methoxyethyl |
| LXXIII-208 | 4-cyanocinnamyl | methoxyethyl |
| LXXIII-209 | 3-(6-chloro-pyridin-3-yl)-allyl | methoxyethyl |
| LXXIII-210 | 3-(4-chlorophenyl)-but-2-enyl | methoxyethyl |
| LXXIII-211 | 3-(4-chlorophenyl)-3-fluoro-allyl | methoxyethyl |
| LXXIII-212 | 3-chloro-4-fluoro-cinnamyl | methoxyethyl |
| LXXIII-213 | 3,5-dichloro-cinnamyl | methoxyethyl |

TABLE 73-continued

| Compound No | R8 | R1 |
|---|---|---|
| LXXIII-214 | 5-phenyl-penta-2,4-dienyl | methoxyethyl |
| LXXIII-215 | 4-isopropyloxycarbonylamino-cinnamyl | methoxyethyl |
| LXXIII-216 | 3-naphthalen-2-yl-allyl | methoxyethyl |
| LXXIII-217 | 3-(5-trifluoromethyl-pyridin-2-yl)-allyl | methoxyethyl |
| LXXIII-218 | 3-(5-chloro-pyridin-2-yl)-allyl | methoxyethyl |
| LXXIII-219 | 3-pyridin-4-yl-allyl | methoxyethyl |
| LXXIII-220 | 3-(2-Chloro-pyridin-4-yl)-allyl | methoxyethyl |
| LXXIII-221 | Cinnamyl | 2,2,2-trifluoroethyl |
| LXXIII-222 | 4-chlorocinnamyl | 2,2,2-trifluoroethyl |
| LXXIII-223 | 4-fluorocinnamyl | 2,2,2-trifluoroethyl |
| LXXIII-224 | 4-bromocinnamyl | 2,2,2-trifluoroethyl |
| LXXIII-225 | 4-trifluoromethylcinnamyl | 2,2,2-trifluoroethyl |
| LXXIII-226 | 4-trifluoromethoxycinnamyl | 2,2,2-trifluoroethyl |
| LXXIII-227 | 4-pentafluoroethoxycinnamyl | 2,2,2-trifluoroethyl |
| LXXIII-228 | 4-methoxycinnamyl | 2,2,2-trifluoroethyl |
| LXXIII-229 | 4-ethoxycinnamyl | 2,2,2-trifluoroethyl |
| LXXIII-230 | 4-cyanocinnamyl | 2,2,2-trifluoroethyl |
| LXXIII-231 | 3-(6-chloro-pyridin-3-yl)-allyl | 2,2,2-trifluoroethyl |
| LXXIII-232 | 3-(4-chlorophenyl)-but-2-enyl | 2,2,2-trifluoroethyl |
| LXXIII-233 | 3-(4-chlorophenyl)-3-fluoro-allyl | 2,2,2-trifluoroethyl |
| LXXIII-234 | 3-chloro-4-fluoro-cinnamyl | 2,2,2-trifluoroethyl |
| LXXIII-235 | 3,5-dichloro-cinnamyl | 2,2,2-trifluoroethyl |
| LXXIII-236 | 5-phenyl-penta-2,4-dienyl | 2,2,2-trifluoroethyl |
| LXXIII-237 | 4-isopropyloxycarbonylamino-cinnamyl | 2,2,2-trifluoroethyl |
| LXXIII-238 | 3-naphthalen-2-yl-allyl | 2,2,2-trifluoroethyl |
| LXXIII-239 | 3-(5-trifluoromethyl-pyridin-2-yl)-allyl | 2,2,2-trifluoroethyl |
| LXXIII-240 | 3-(5-chloro-pyridin-2-yl)-allyl | 2,2,2-trifluoroethyl |
| LXXIII-241 | 3-pyridin-4-yl-allyl | 2,2,2-trifluoroethyl |
| LXXIII-242 | 3-(2-Chloro-pyridin-4-yl)-allyl | 2,2,2-trifluoroethyl |
| LXXIII-243 | Cinnamyl | methoxy |
| LXXIII-244 | 4-chlorocinnamyl | methoxy |
| LXXIII-245 | 4-fluorocinnamyl | methoxy |
| LXXIII-246 | 4-bromocinnamyl | methoxy |
| LXXIII-247 | 4-trifluoromethylcinnamyl | methoxy |
| LXXIII-248 | 4-trifluoromethoxycinnamyl | methoxy |
| LXXIII-249 | 4-pentafluoroethoxycinnamyl | methoxy |
| LXXIII-250 | 4-methoxycinnamyl | methoxy |
| LXXIII-251 | 4-ethoxycinnamyl | methoxy |
| LXXIII-252 | 4-cyanocinnamyl | methoxy |
| LXXIII-253 | 3-(6-chloro-pyridin-3-yl)-allyl | methoxy |
| LXXIII-254 | 3-(4-chlorophenyl)-but-2-enyl | methoxy |
| LXXIII-255 | 3-(4-chlorophenyl)-3-fluoro-allyl | methoxy |
| LXXIII-256 | 3-chloro-4-fluoro-cinnamyl | methoxy |
| LXXIII-257 | 3,5-dichloro-cinnamyl | methoxy |
| LXXIII-258 | 5-phenyl-penta-2,4-dienyl | methoxy |
| LXXIII-259 | 4-isopropyloxycarbonylamino-cinnamyl | methoxy |
| LXXIII-260 | 3-naphthalen-2-yl-allyl | methoxy |
| LXXIII-261 | 3-(5-trifluoromethyl-pyridin-2-yl)-allyl | methoxy |
| LXXIII-262 | 3-(5-chloro-pyridin-2-yl)-allyl | methoxy |
| LXXIII-263 | 3-pyridin-4-yl-allyl | methoxy |
| LXXIII-264 | 3-(2-Chloro-pyridin-4-yl)-allyl | methoxy |
| LXXIII-265 | Cinnamyl | 2,1,3-benzoxadiazole-5-yl |
| LXXIII-266 | 4-chlorocinnamyl | 2,1,3-benzoxadiazole-5-yl |
| LXXIII-267 | 4-fluorocinnamyl | 2,1,3-benzoxadiazole-5-yl |
| LXXIII-268 | 4-bromocinnamyl | 2,1,3-benzoxadiazole-5-yl |
| LXXIII-269 | 4-trifluoromethylcinnamyl | 2,1,3-benzoxadiazole-5-yl |
| LXXIII-270 | 4-trifluoromethoxycinnamyl | 2,1,3-benzoxadiazole-5-yl |
| LXXIII-271 | 4-pentafluoroethoxycinnamyl | 2,1,3-benzoxadiazole-5-yl |
| LXXIII-272 | 4-methoxycinnamyl | 2,1,3-benzoxadiazole-5-yl |
| LXXIII-273 | 4-ethoxycinnamyl | 2,1,3-benzoxadiazole-5-yl |
| LXXIII-274 | 4-cyanocinnamyl | 2,1,3-benzoxadiazole-5-yl |
| LXXIII-275 | 3-(6-chloro-pyridin-3-yl)-allyl | 2,1,3-benzoxadiazole-5-yl |
| LXXIII-276 | 3-(4-chlorophenyl)-but-2-enyl | 2,1,3-benzoxadiazole-5-yl |
| LXXIII-277 | 3-(4-chlorophenyl)-3-fluoro-allyl | 2,1,3-benzoxadiazole-5-yl |
| LXXIII-278 | 3-chloro-4-fluoro-cinnamyl | 2,1,3-benzoxadiazole-5-yl |
| LXXIII-279 | 3,5-dichloro-cinnamyl | 2,1,3-benzoxadiazole-5-yl |
| LXXIII-280 | 5-phenyl-penta-2,4-dienyl | 2,1,3-benzoxadiazole-5-yl |
| LXXIII-281 | 4-isopropyloxycarbonylamino-cinnamyl | 2,1,3-benzoxadiazole-5-yl |
| LXXIII-282 | 3-naphthalen-2-yl-allyl | 2,1,3-benzoxadiazole-5-yl |
| LXXIII-283 | 3-(5-trifluoromethyl-pyridin-2-yl)-allyl | 2,1,3-benzoxadiazole-5-yl |
| LXXIII-284 | 3-(5-chloro-pyridin-2-yl)-allyl | 2,1,3-benzoxadiazole-5-yl |
| LXXIII-285 | 3-pyridin-4-yl-allyl | 2,1,3-benzoxadiazole-5-yl |
| LXXIII-286 | 3-(2-Chloro-pyridin-4-yl)-allyl | 2,1,3-benzoxadiazole-5-yl |
| LXXIII-287 | Cinnamyl | methoxypropylamino |
| LXXIII-288 | 4-chlorocinnamyl | methoxypropylamino |
| LXXIII-289 | 4-fluorocinnamyl | methoxypropylamino |
| LXXIII-290 | 4-bromocinnamyl | methoxypropylamino |
| LXXIII-291 | 4-trifluoromethylcinnamyl | methoxypropylamino |

TABLE 73-continued

| Compound No | R8 | R1 |
|---|---|---|
| LXXIII-292 | 4-trifluoromethoxycinnamyl | methoxypropylamino |
| LXXIII-293 | 4-pentafluoroethoxycinnamyl | methoxypropylamino |
| LXXIII-294 | 4-methoxycinnamyl | methoxypropylamino |
| LXXIII-295 | 4-ethoxycinnamyl | methoxypropylamino |
| LXXIII-296 | 4-cyanocinnamyl | methoxypropylamino |
| LXXIII-297 | 3-(6-chloro-pyridin-3-yl)-allyl | methoxypropylamino |
| LXXIII-298 | 3-(4-chlorophenyl)-but-2-enyl | methoxypropylamino |
| LXXIII-299 | 3-(4-chlorophenyl)-3-fluoro-allyl | methoxypropylamino |
| LXXIII-300 | 3-chloro-4-fluoro-cinnamyl | methoxypropylamino |
| LXXIII-301 | 3,5-dichloro-cinnamyl | methoxypropylamino |
| LXXIII-302 | 5-phenyl-penta-2,4-dienyl | methoxypropylamino |
| LXXIII-303 | 4-isopropyloxycarbonylamino-cinnamyl | methoxypropylamino |
| LXXIII-304 | 3-naphthalen-2-yl-allyl | methoxypropylamino |
| LXXIII-305 | 3-(5-trifluoromethyl-pyridin-2-yl)-allyl | methoxypropylamino |
| LXXIII-306 | 3-(5-chloro-pyridin-2-yl)-allyl | methoxypropylamino |
| LXXIII-307 | 3-pyridin-4-yl-allyl | methoxypropylamino |
| LXXIII-308 | 3-(2-Chloro-pyridin-4-yl)-allyl | methoxypropylamino |
| LXXIII-309 | Cinnamyl | 2-chloro-thiazol-5-yl |
| LXXIII-310 | 4-chlorocinnamyl | 2-chloro-thiazol-5-yl |
| LXXIII-311 | 4-fluorocinnamyl | 2-chloro-thiazol-5-yl |
| LXXIII-312 | 4-bromocinnamyl | 2-chloro-thiazol-5-yl |
| LXXIII-313 | 4-trifluoromethylcinnamyl | 2-chloro-thiazol-5-yl |
| LXXIII-314 | 4-trifluoromethoxycinnamyl | 2-chloro-thiazol-5-yl |
| LXXIII-315 | 4-pentafluoroethoxycinnamyl | 2-chloro-thiazol-5-yl |
| LXXIII-316 | 4-methoxycinnamyl | 2-chloro-thiazol-5-yl |
| LXXIII-317 | 4-ethoxycinnamyl | 2-chloro-thiazol-5-yl |
| LXXIII-318 | 4-cyanocinnamyl | 2-chloro-thiazol-5-yl |
| LXXIII-319 | 3-(6-chloro-pyridin-3-yl)-allyl | 2-chloro-thiazol-5-yl |
| LXXIII-320 | 3-(4-chlorophenyl)-but-2-enyl | 2-chloro-thiazol-5-yl |
| LXXIII-321 | 3-(4-chlorophenyl)-3-fluoro-allyl | 2-chloro-thiazol-5-yl |
| LXXIII-322 | 3-chloro-4-fluoro-cinnamyl | 2-chloro-thiazol-5-yl |
| LXXIII-323 | 3,5-dichloro-cinnamyl | 2-chloro-thiazol-5-yl |
| LXXIII-324 | 5-phenyl-penta-2,4-dienyl | 2-chloro-thiazol-5-yl |
| LXXIII-325 | 4-isopropyloxycarbonylamino-cinnamyl | 2-chloro-thiazol-5-yl |
| LXXIII-326 | 3-naphthalen-2-yl-allyl | 2-chloro-thiazol-5-yl |
| LXXIII-327 | 3-(5-trifluoromethyl-pyridin-2-yl)-allyl | 2-chloro-thiazol-5-yl |
| LXXIII-328 | 3-(5-chloro-pyridin-2-yl)-allyl | 2-chloro-thiazol-5-yl |
| LXXIII-329 | 3-pyridin-4-yl-allyl | 2-chloro-thiazol-5-yl |
| LXXIII-330 | 3-(2-Chloro-pyridin-4-yl)-allyl | 2-chloro-thiazol-5-yl |
| LXXIII-331 | Cinnamyl | i-propylamino |
| LXXIII-332 | 4-chlorocinnamyl | i-propylamino |
| LXXIII-333 | 4-fluorocinnamyl | i-propylamino |
| LXXIII-334 | 4-bromocinnamyl | i-propylamino |
| LXXIII-335 | 4-trifluoromethylcinnamyl | i-propylamino |
| LXXIII-336 | 4-trifluoromethoxycinnamyl | i-propylamino |
| LXXIII-337 | 4-pentafluoroethoxycinnamyl | i-propylamino |
| LXXIII-338 | 4-methoxycinnamyl | i-propylamino |
| LXXIII-339 | 4-ethoxycinnamyl | i-propylamino |
| LXXIII-340 | 4-cyanocinnamyl | i-propylamino |
| LXXIII-341 | 3-(6-chloro-pyridin-3-yl)-allyl | i-propylamino |
| LXXIII-342 | 3-(4-chlorophenyl)-but-2-enyl | i-propylamino |
| LXXIII-343 | 3-(4-chlorophenyl)-3-fluoro-allyl | i-propylamino |
| LXXIII-344 | 3-chloro-4-fluoro-cinnamyl | i-propylamino |
| LXXIII-345 | 3,5-dichloro-cinnamyl | i-propylamino |
| LXXIII-346 | 5-phenyl-penta-2,4-dienyl | i-propylamino |
| LXXIII-347 | 4-isopropyloxycarbonylamino-cinnamyl | i-propylamino |
| LXXIII-348 | 3-naphthalen-2-yl-allyl | i-propylamino |
| LXXIII-349 | 3-(5-trifluoromethyl-pyridin-2-yl)-allyl | i-propylamino |
| LXXIII-350 | 3-(5-chloro-pyridin-2-yl)-allyl | i-propylamino |
| LXXIII-351 | 3-pyridin-4-yl-allyl | i-propylamino |
| LXXIII-352 | 3-(2-Chloro-pyridin-4-yl)-allyl | i-propylamino |
| LXXIII-353 | Cinnamyl | 1,3-dioxolan-2-yl-ethylamino |
| LXXIII-354 | 4-chlorocinnamyl | 1,3-dioxolan-2-yl-ethylamino |
| LXXIII-355 | 4-fluorocinnamyl | 1,3-dioxolan-2-yl-ethylamino |
| LXXIII-356 | 4-bromocinnamyl | 1,3-dioxolan-2-yl-ethylamino |
| LXXIII-357 | 4-trifluoromethylcinnamyl | 1,3-dioxolan-2-yl-ethylamino |
| LXXIII-358 | 4-trifluoromethoxycinnamyl | 1,3-dioxolan-2-yl-ethylamino |
| LXXIII-359 | 4-pentafluoroethoxycinnamyl | 1,3-dioxolan-2-yl-ethylamino |
| LXXIII-360 | 4-methoxycinnamyl | 1,3-dioxolan-2-yl-ethylamino |
| LXXIII-361 | 4-ethoxycinnamyl | 1,3-dioxolan-2-yl-ethylamino |
| LXXIII-362 | 4-cyanocinnamyl | 1,3-dioxolan-2-yl-ethylamino |
| LXXIII-363 | 3-(6-chloro-pyridin-3-yl)-allyl | 1,3-dioxolan-2-yl-ethylamino |
| LXXIII-364 | 3-(4-chlorophenyl)-but-2-enyl | 1,3-dioxolan-2-yl-ethylamino |
| LXXIII-365 | 3-(4-chlorophenyl)-3-fluoro-allyl | 1,3-dioxolan-2-yl-ethylamino |
| LXXIII-366 | 3-chloro-4-fluoro-cinnamyl | 1,3-dioxolan-2-yl-ethylamino |
| LXXIII-367 | 3,5-dichloro-cinnamyl | 1,3-dioxolan-2-yl-ethylamino |
| LXXIII-368 | 5-phenyl-penta-2,4-dienyl | 1,3-dioxolan-2-yl-ethylamino |
| LXXIII-369 | 4-isopropyloxycarbonylamino-cinnamyl | 1,3-dioxolan-2-yl-ethylamino |

TABLE 73-continued

| Compound No | R8 | R1 |
|---|---|---|
| LXXIII-370 | 3-naphthalen-2-yl-allyl | 1,3-dioxolan-2-yl-ethylamino |
| LXXIII-371 | 3-(5-trifluoromethyl-pyridin-2-yl)-allyl | 1,3-dioxolan-2-yl-ethylamino |
| LXXIII-372 | 3-(5-chloro-pyridin-2-yl)-allyl | 1,3-dioxolan-2-yl-ethylamino |
| LXXIII-373 | 3-pyridin-4-yl-allyl | 1,3-dioxolan-2-yl-ethylamino |
| LXXIII-374 | 3-(2-Chloro-pyridin-4-yl)-allyl | 1,3-dioxolan-2-yl-ethylamino |
| LXXIII-375 | Cinnamyl | 2-chloro-pyrid-4-yl-methylamino |
| LXXIII-376 | 4-chlorocinnamyl | 2-chloro-pyrid-4-yl-methylamino |
| LXXIII-377 | 4-fluorocinnamyl | 2-chloro-pyrid-4-yl-methylamino |
| LXXIII-378 | 4-bromocinnamyl | 2-chloro-pyrid-4-yl-methylamino |
| LXXIII-379 | 4-trifluoromethylcinnamyl | 2-chloro-pyrid-4-yl-methylamino |
| LXXIII-380 | 4-trifluoromethoxycinnamyl | 2-chloro-pyrid-4-yl-methylamino |
| LXXIII-381 | 4-pentafluoroethoxycinnamyl | 2-chloro-pyrid-4-yl-methylamino |
| LXXIII-382 | 4-methoxycinnamyl | 2-chloro-pyrid-4-yl-methylamino |
| LXXIII-383 | 4-ethoxycinnamyl | 2-chloro-pyrid-4-yl-methylamino |
| LXXIII-384 | 4-cyanocinnamyl | 2-chloro-pyrid-4-yl-methylamino |
| LXXIII-385 | 3-(6-chloro-pyridin-3-yl)-allyl | 2-chloro-pyrid-4-yl-methylamino |
| LXXIII-386 | 3-(4-chlorophenyl)-but-2-enyl | 2-chloro-pyrid-4-yl-methylamino |
| LXXIII-387 | 3-(4-chlorophenyl)-3-fluoro-allyl | 2-chloro-pyrid-4-yl-methylamino |
| LXXIII-388 | 3-chloro-4-fluoro-cinnamyl | 2-chloro-pyrid-4-yl-methylamino |
| LXXIII-389 | 3,5-dichloro-cinnamyl | 2-chloro-pyrid-4-yl-methylamino |
| LXXIII-390 | 5-phenyl-penta-2,4-dienyl | 2-chloro-pyrid-4-yl-methylamino |
| LXXIII-391 | 4-isopropyloxycarbonylamino-cinnamyl | 2-chloro-pyrid-4-yl-methylamino |
| LXXIII-392 | 3-naphthalen-2-yl-allyl | 2-chloro-pyrid-4-yl-methylamino |
| LXXIII-393 | 3-(5-trifluoromethyl-pyridin-2-yl)-allyl | 2-chloro-pyrid-4-yl-methylamino |
| LXXIII-394 | 3-(5-chloro-pyridin-2-yl)-allyl | 2-chloro-pyrid-4-yl-methylamino |
| LXXIII-395 | 3-pyridin-4-yl-allyl | 2-chloro-pyrid-4-yl-methylamino |
| LXXIII-396 | 3-(2-Chloro-pyridin-4-yl)-allyl | 2-chloro-pyrid-4-yl-methylamino |
| LXXIII-397 | Cinnamyl | 2-trfluoromethyl-pyrid-5-yl-methylamino |
| LXXIII-398 | 4-chlorocinnamyl | 2-trfluoromethyl-pyrid-5-yl-methylamino |
| LXXIII-399 | 4-fluorocinnamyl | 2-trfluoromethyl-pyrid-5-yl-methylamino |
| LXXIII-400 | 4-bromocinnamyl | 2-trfluoromethyl-pyrid-5-yl-methylamino |
| LXXIII-401 | 4-trifluoromethylcinnamyl | 2-trfluoromethyl-pyrid-5-yl-methylamino |
| LXXIII-402 | 4-trifluoromethoxycinnamyl | 2-trfluoromethyl-pyrid-5-yl-methylamino |
| LXXIII-403 | 4-pentafluoroethoxycinnamyl | 2-trfluoromethyl-pyrid-5-yl-methylamino |
| LXXIII-404 | 4-methoxycinnamyl | 2-trfluoromethyl-pyrid-5-yl-methylamino |
| LXXIII-405 | 4-ethoxycinnamyl | 2-trfluoromethyl-pyrid-5-yl-methylamino |
| LXXIII-406 | 4-cyanocinnamyl | 2-trfluoromethyl-pyrid-5-yl-methylamino |
| LXXIII-407 | 3-(6-chloro-pyridin-3-yl)-allyl | 2-trfluoromethyl-pyrid-5-yl-methylamino |
| LXXIII-408 | 3-(4-chlorophenyl)-but-2-enyl | 2-trfluoromethyl-pyrid-5-yl-methylamino |
| LXXIII-409 | 3-(4-chlorophenyl)-3-fluoro-allyl | 2-trfluoromethyl-pyrid-5-yl-methylamino |
| LXXIII-410 | 3-chloro-4-fluoro-cinnamyl | 2-trfluoromethyl-pyrid-5-yl-methylamino |
| LXXIII-411 | 3,5-dichloro-cinnamyl | 2-trfluoromethyl-pyrid-5-yl-methylamino |
| LXXIII-412 | 5-phenyl-penta-2,4-dienyl | 2-trfluoromethyl-pyrid-5-yl-methylamino |
| LXXIII-413 | 4-isopropyloxycarbonylamino-cinnamyl | 2-trfluoromethyl-pyrid-5-yl-methylamino |
| LXXIII-414 | 3-naphthalen-2-yl-allyl | 2-trfluoromethyl-pyrid-5-yl-methylamino |
| LXXIII-415 | 3-(5-trifluoromethyl-pyridin-2-yl)-allyl | 2-trfluoromethyl-pyrid-5-yl-methylamino |
| LXXIII-416 | 3-(5-chloro-pyridin-2-yl)-allyl | 2-trfluoromethyl-pyrid-5-yl-methylamino |
| LXXIII-417 | 3-pyridin-4-yl-allyl | 2-trfluoromethyl-pyrid-5-yl-methylamino |
| LXXIII-418 | 3-(2-Chloro-pyridin-4-yl)-allyl | 2-trfluoromethyl-pyrid-5-yl-methylamino |
| LXXIII-419 | Cinnamyl | methylamino |
| LXXIII-420 | 4-chlorocinnamyl | methylamino |
| LXXIII-421 | 4-fluorocinnamyl | methylamino |
| LXXIII-422 | 4-bromocinnamyl | methylamino |
| LXXIII-423 | 4-trifluoromethylcinnamyl | methylamino |
| LXXIII-424 | 4-trifluoromethoxycinnamyl | methylamino |
| LXXIII-425 | 4-pentafluoroethoxycinnamyl | methylamino |
| LXXIII-426 | 4-methoxycinnamyl | methylamino |
| LXXIII-427 | 4-ethoxycinnamyl | methylamino |
| LXXIII-428 | 4-cyanocinnamyl | methylamino |
| LXXIII-429 | 3-(6-chloro-pyridin-3-yl)-allyl | methylamino |
| LXXIII-430 | 3-(4-chlorophenyl)-but-2-enyl | methylamino |
| LXXIII-431 | 3-(4-chlorophenyl)-3-fluoro-allyl | methylamino |
| LXXIII-432 | 3-chloro-4-fluoro-cinnamyl | methylamino |
| LXXIII-433 | 3,5-dichloro-cinnamyl | methylamino |
| LXXIII-434 | 5-phenyl-penta-2,4-dienyl | methylamino |
| LXXIII-435 | 4-isopropyloxycarbonylamino-cinnamyl | methylamino |
| LXXIII-436 | 3-naphthalen-2-yl-allyl | methylamino |
| LXXIII-437 | 3-(5-trifluoromethyl-pyridin-2-yl)-allyl | methylamino |
| LXXIII-438 | 3-(5-chloro-pyridin-2-yl)-allyl | methylamino |
| LXXIII-439 | 3-pyridin-4-yl-allyl | methylamino |
| LXXIII-440 | 3-(2-Chloro-pyridin-4-yl)-allyl | methylamino |
| LXXIII-441 | Cinnamyl | ethylamino |
| LXXIII-442 | 4-chlorocinnamyl | ethylamino |
| LXXIII-443 | 4-fluorocinnamyl | ethylamino |
| LXXIII-444 | 4-bromocinnamyl | ethylamino |
| LXXIII-445 | 4-trifluoromethylcinnamyl | ethylamino |
| LXXIII-446 | 4-trifluoromethoxycinnamyl | ethylamino |
| LXXIII-447 | 4-pentafluoroethoxycinnamyl | ethylamino |

TABLE 73-continued

| Compound No | R8 | R1 |
|---|---|---|
| LXXIII-448 | 4-methoxycinnamyl | ethylamino |
| LXXIII-449 | 4-ethoxycinnamyl | ethylamino |
| LXXIII-450 | 4-cyanocinnamyl | ethylamino |
| LXXIII-451 | 3-(6-chloro-pyridin-3-yl)-allyl | ethylamino |
| LXXIII-452 | 3-(4-chlorophenyl)-but-2-enyl | ethylamino |
| LXXIII-453 | 3-(4-chlorophenyl)-3-fluoro-allyl | ethylamino |
| LXXIII-454 | 3-chloro-4-fluoro-cinnamyl | ethylamino |
| LXXIII-455 | 3,5-dichloro-cinnamyl | ethylamino |
| LXXIII-456 | 5-phenyl-penta-2,4-dienyl | ethylamino |
| LXXIII-457 | 4-isopropyloxycarbonylamino-cinnamyl | ethylamino |
| LXXIII-458 | 3-naphthalen-2-yl-allyl | ethylamino |
| LXXIII-459 | 3-(5-trifluoromethyl-pyridin-2-yl)-allyl | ethylamino |
| LXXIII-460 | 3-(5-chloro-pyridin-2-yl)-allyl | ethylamino |
| LXXIII-461 | 3-pyridin-4-yl-allyl | ethylamino |
| LXXIII-462 | 3-(2-Chloro-pyridin-4-yl)-allyl | ethylamino |
| LXXIII-463 | Cinnamyl | 2-chloro-pyrid-4-yl-amino |
| LXXIII-464 | 4-chlorocinnamyl | 2-chloro-pyrid-4-yl-amino |
| LXXIII-465 | 4-fluorocinnamyl | 2-chloro-pyrid-4-yl-amino |
| LXXIII-466 | 4-bromocinnamyl | 2-chloro-pyrid-4-yl-amino |
| LXXIII-467 | 4-trifluoromethylcinnamyl | 2-chloro-pyrid-4-yl-amino |
| LXXIII-468 | 4-trifluoromethoxycinnamyl | 2-chloro-pyrid-4-yl-amino |
| LXXIII-469 | 4-pentafluoroethoxycinnamyl | 2-chloro-pyrid-4-yl-amino |
| LXXIII-470 | 4-methoxycinnamyl | 2-chloro-pyrid-4-yl-amino |
| LXXIII-471 | 4-ethoxycinnamyl | 2-chloro-pyrid-4-yl-amino |
| LXXIII-472 | 4-cyanocinnamyl | 2-chloro-pyrid-4-yl-amino |
| LXXIII-473 | 3-(6-chloro-pyridin-3-yl)-allyl | 2-chloro-pyrid-4-yl-amino |
| LXXIII-474 | 3-(4-chlorophenyl)-but-2-enyl | 2-chloro-pyrid-4-yl-amino |
| LXXIII-475 | 3-(4-chlorophenyl)-3-fluoro-allyl | 2-chloro-pyrid-4-yl-amino |
| LXXIII-476 | 3-chloro-4-fluoro-cinnamyl | 2-chloro-pyrid-4-yl-amino |
| LXXIII-477 | 3,5-dichloro-cinnamyl | 2-chloro-pyrid-4-yl-amino |
| LXXIII-478 | 5-phenyl-penta-2,4-dienyl | 2-chloro-pyrid-4-yl-amino |
| LXXIII-479 | 4-isopropyloxycarbonylamino-cinnamyl | 2-chloro-pyrid-4-yl-amino |
| LXXIII-480 | 3-naphthalen-2-yl-allyl | 2-chloro-pyrid-4-yl-amino |
| LXXIII-481 | 3-(5-trifluoromethyl-pyridin-2-yl)-allyl | 2-chloro-pyrid-4-yl-amino |
| LXXIII-482 | 3-(5-chloro-pyridin-2-yl)-allyl | 2-chloro-pyrid-4-yl-amino |
| LXXIII-483 | 3-pyridin-4-yl-allyl | 2-chloro-pyrid-4-yl-amino |
| LXXIII-484 | 3-(2-Chloro-pyridin-4-yl)-allyl | 2-chloro-pyrid-4-yl-amino |
| LXXIII-485 | Cinnamyl | methoxyethylamino |
| LXXIII-486 | 4-chlorocinnamyl | methoxyethylamino |
| LXXIII-487 | 4-fluorocinnamyl | methoxyethylamino |
| LXXIII-488 | 4-bromocinnamyl | methoxyethylamino |
| LXXIII-489 | 4-trifluoromethylcinnamyl | methoxyethylamino |
| LXXIII-490 | 4-trifluoromethoxycinnamyl | methoxyethylamino |
| LXXIII-491 | 4-pentafluoroethoxycinnamyl | methoxyethylamino |
| LXXIII-492 | 4-methoxycinnamyl | methoxyethylamino |
| LXXIII-493 | 4-ethoxycinnamyl | methoxyethylamino |
| LXXIII-494 | 4-cyanocinnamyl | methoxyethylamino |
| LXXIII-495 | 3-(6-chloro-pyridin-3-yl)-allyl | methoxyethylamino |
| LXXIII-496 | 3-(4-chlorophenyl)-but-2-enyl | methoxyethylamino |
| LXXIII-497 | 3-(4-chlorophenyl)-3-fluoro-allyl | methoxyethylamino |
| LXXIII-498 | 3-chloro-4-fluoro-cinnamyl | methoxyethylamino |
| LXXIII-499 | 3,5-dichloro-cinnamyl | methoxyethylamino |
| LXXIII-500 | 5-phenyl-penta-2,4-dienyl | methoxyethylamino |
| LXXIII-501 | 4-isopropyloxycarbonylamino-cinnamyl | methoxyethylamino |
| LXXIII-502 | 3-naphthalen-2-yl-allyl | methoxyethylamino |
| LXXIII-503 | 3-(5-trifluoromethyl-pyridin-2-yl)-allyl | methoxyethylamino |
| LXXIII-504 | 3-(5-chloro-pyridin-2-yl)-allyl | methoxyethylamino |
| LXXIII-505 | 3-pyridin-4-yl-allyl | methoxyethylamino |
| LXXIII-506 | 3-(2-Chloro-pyridin-4-yl)-allyl | methoxyethylamino |

Table LXXIV provides 506 compounds of formula Iya

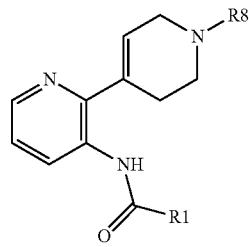
(Iya)

wherein the values of $R^8$ and $R^1$ are given in Table 73.

Table LXXV provides 506 compounds of formula Iyb

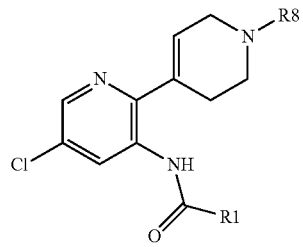
(Iyb)

wherein the values of $R^8$ and $R^1$ are given in Table 73.

Table LXXVI provides 506 compounds of formula Iyc

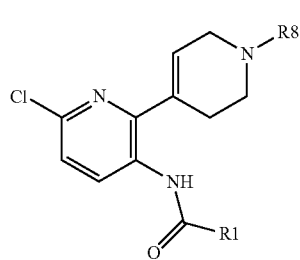
(Iyc)

wherein the values of $R^8$ and $R^1$ are given in Table 73.

Table LXXVII provides 506 compounds of formula Iyd

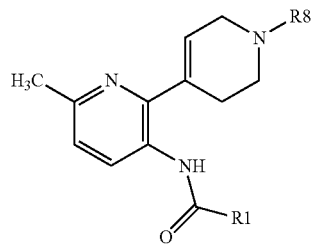
(Iyd)

wherein the values of $R^8$ and $R^1$ are given in Table 73.

Table LXXVIII provides 506 compounds of formula Iye

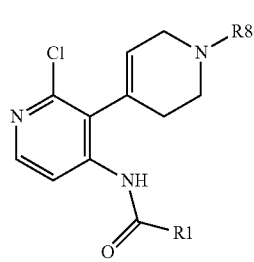
(Iye)

wherein the values of $R^8$ and $R^1$ are given in Table 73.

Table LXXIX provides 506 compounds of formula Iyf

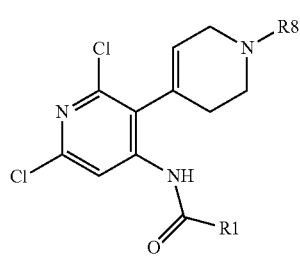
(Iyf)

wherein the values of $R^8$ and $R^1$ are given in Table 73.

Table LXXX provides 506 compounds of formula Iyg

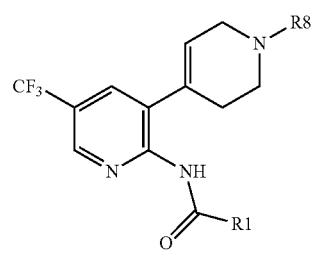
(Iyg)

wherein the values of $R^8$ and $R^1$ are given in Table 73.

Table LXXXI provides 506 compounds of formula Iyh

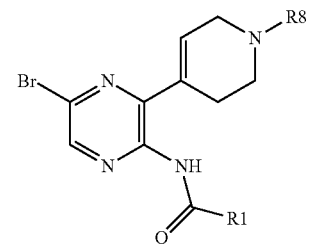
(Iyh)

wherein the values of $R^8$ and $R^1$ are given in Table 73.

Table LXXXII provides 506 compounds of formula Iyi

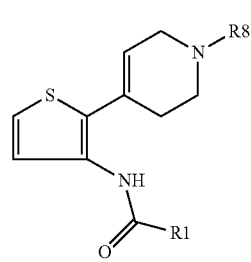
(Iyi)

wherein the values of $R^8$ and $R^1$ are given in Table 73.

Table LXXXIII provides 506 compounds of formula Iyj

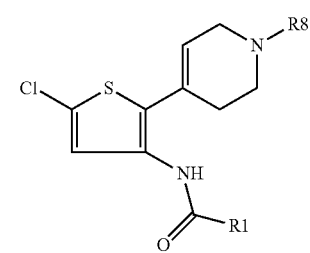
(Iyj)

wherein the values of $R^8$ and $R^1$ are given in Table 73.

Table LXXXIV provides 506 compounds of formula Iyk

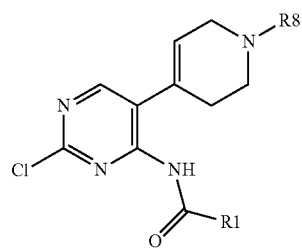

wherein the values of R$^8$ and R$^1$ are given in Table 73.

Table LXXXV provides 506 compounds of formula Iyl

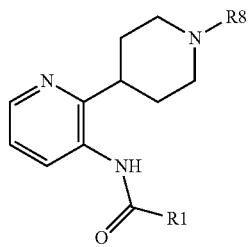

wherein the values of R$^8$ and R$^1$ are given in Table 73.

Table LXXXVI provides 506 compounds of formula Iym

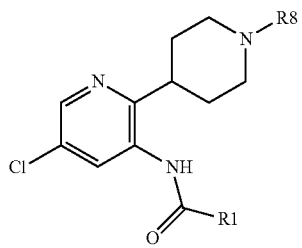

wherein the values of R$^8$ and R$^1$ are given in Table 73.

Table LXXXVII provides 506 compounds of formula Iyn

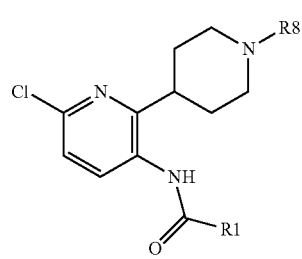

wherein the values of R$^8$ and R$^1$ are given in Table 73.

Table LXXXVIII provides 506 compounds of formula Iyo

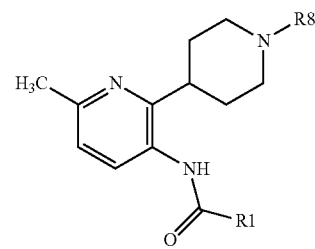

wherein the values of R$^8$ and R$^1$ are given in Table 73.

Table LXXXIX provides 506 compounds of formula Iyp

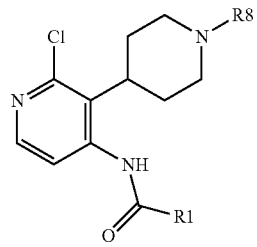

wherein the values of R$^8$ and R$^1$ are given in Table 73.

Table XC provides 506 compounds of formula Iyq

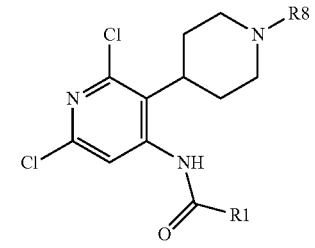

wherein the values of R$^8$ and R$^1$ are given in Table 73.

Table XCI provides 506 compounds of formula Iyr

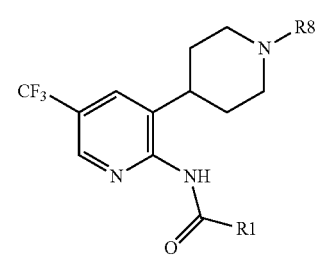

wherein the values of R$^8$ and R$^1$ are given in Table 73.

Table XCII provides 506 compounds of formula Iys

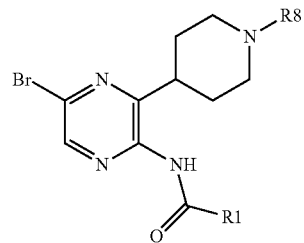

(Iys)

wherein the values of $R^8$ and $R^1$ are given in Table 73.
Table XCIII provides 506 compounds of formula Iyt

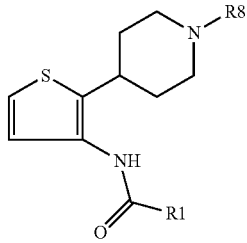

(Iyt)

wherein the values of $R^8$ and $R^1$ are given in Table 73.

Table XCIV provides 506 compounds of formula Iyu

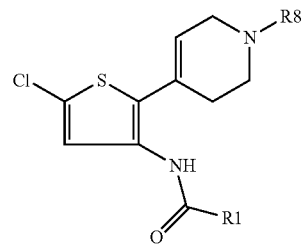

(Iyu)

wherein the values of $R^8$ and $R^1$ are given in Table 73.
Table XCV provides 506 compounds of formula Iyv

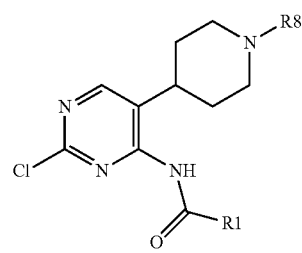

(Iyv)

wherein the values of $R^8$ and $R^1$ are given in Table 73.

The compounds of the invention may be made by a variety of methods.

For example tetrahydropyridyl compounds of the general formula 1 may be prepared according to the reactions of Scheme 1.

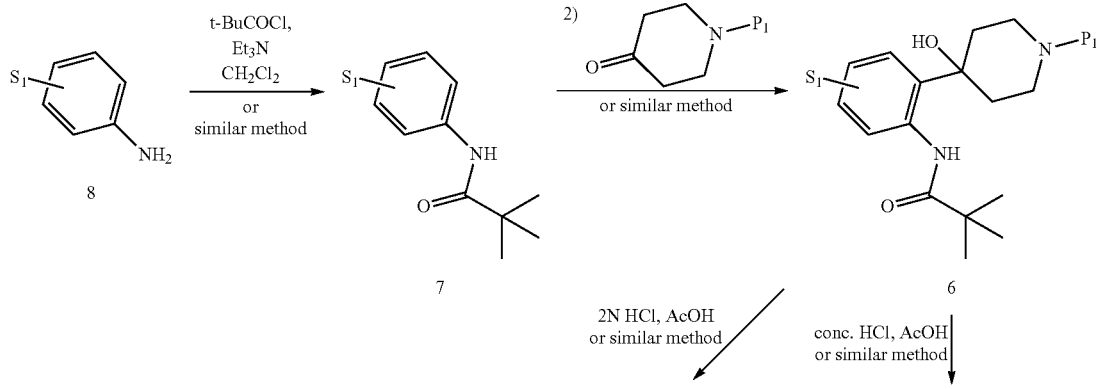

87

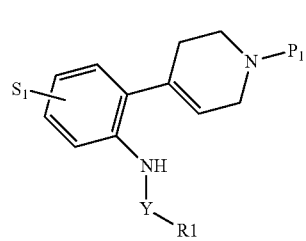

10

88

-continued

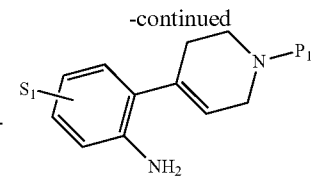

9

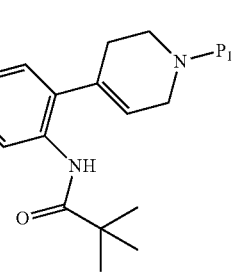

5

1) CH₃CHClOCOCl
   toluene, reflux
2) MeOH, reflux
   or similar method

6N HCl
(P1 = R8)
or similar
method

1) CH₃CHClOCOCl
   toluene, reflux
2) MeOH, reflux
   or similar method

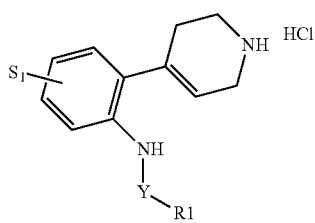

11

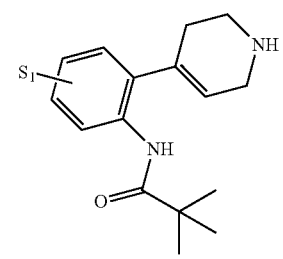

4

R8-Hal,
Hünig base, CH₃CN
or similar method

R8-Hal,
Hünig base, CH₃CN
or similar method

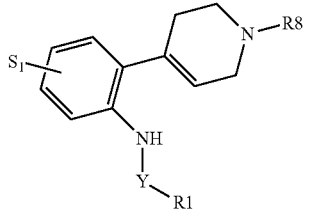

1

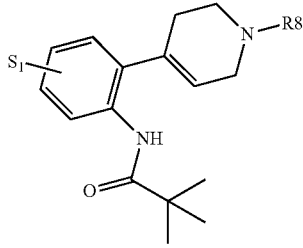

2

6N HCl
or similar
method

3

P1 is R⁸ or is a suitable protective group for example a group such as BOC, benzyl or alkyl and S₁ is the group (R⁴)n.

The synthetic route shown in Scheme 1 may also be used for the preparation of some compounds of formula I wherein the ring is a 5 or 6 membered heteroaromatic ring instead of the phenyl group.

Thus a compound of formula 1 may be obtained from a compound of formula 2 by to reaction with a suitable electrophilic species. Compounds of formula 1 where Y is a carbonyl group may be formed by the reaction of compounds of formula 2 with a carboxylic acid derivative of formula R¹—C(O)—Z' where Z' is chloride, hydroxy, alkoxy or acyloxy at a temperature between 0° C. and 150° C. optionally in an organic solvent such as dichloromethane, chloroform or 1,2-dichloroethane, optionally in the presence of a tertiary amine base such as triethylamine or diisopropylethylamine and optionally in the presence of a coupling agent such as dicyclohexylcarbodiimide. Compounds of formula 1 where Y is a carbonyl group and R¹ is an amino substituent of formula R'—NH— may be formed by the reaction of compounds of formula 2 with an isocyanate of formula R'—N=C=O under similar conditions. Compounds of formula 1 where Y is a group of formula $S(O)_m$ may be formed from compounds of formula 2 by treatment with compounds of formula of R¹—S(O)$_m$—Cl under similar conditions. Compounds of formula 1 where Y is a thiocarbonyl group and R¹ is an amino substituent of formula R'—NH— may be formed by the reaction of compounds of formula 2 with an isothiocyanate of formula R'—N=C=S under similar conditions.

Alternatively compounds of formula 1 where Y is a thiocarbonyl group and $R^1$ is a carbon substituent may be formed by treatment of compounds of formula 1 where Y is a carbonyl group and $R^1$ is a carbon substituent with a suitable thionating agent such as Lawesson's reagent.

In the above procedures, acid derivatives of the formula $R^1$—C(O)—Z', isocyanates of formula R'—N=C=O, isothiocyanates of formula R'—N=C=S and sulfur electrophiles of formula $R^1$—S(O)$_m$—Cl are either known compounds or may be formed from known compounds by known methods by a person skilled in the art.

Compounds of formula 2 may be prepared from compounds of formula 3 by cleavage of the amide bond, according to known methods by a person skilled in the art.

Alternatively compounds of formula 2 may be prepared from compounds of formula 5 where P1 is $R^8$ by cleavage of the amide bond, according to known methods by a person skilled in the art.

Compounds of formula 3 may be obtained from compounds of formula 4 by reaction with an alkylating agent of the formula $R^8$-L, where L is chloride, bromide, iodide or a sulfonate (e.g. mesylate or tosylate) or similar leaving group at a temperature of between ambient temperature and 100° C., typically 65° C., in an organic solvent such as dichloromethane, chloroform or 1,2-dichloroethane in the presence of a tertiary amine base such as triethylamine or diisopropylethylamine and optionally catalysed by halide salts such as sodium iodide, potassium iodide or tetrabutylammonium iodide. Alternatively, a compound of formula 4 may be reacted with an aldehyde of the formula $R^8$—CHO at a temperature between ambient temperature and 100° C. in an organic solvent such as tetrahydrofuran or ethanol or mixtures of solvents in the presence of a reducing agent such as borane-pyridine complex, sodium borohydride, sodium (triacetoxy)borohydride, sodium cyanoborohydride or such like, to produce a compound of formula 3 where $R^8$ is $CH_2$—R.

Compounds of formula 4 may be prepared from compounds of formula 5 where P1 is benzyl or alkyl by a dealkylation reaction, according to known methods by a person skilled in the art. Compounds of formula 4 may be prepared from compounds of formula 5 where P1 is BOC by treatment with an acid such as $CF_3COOH$, according to known methods by a person skilled in the art.

Alternatively, compounds of formula 4 may be formed by the reaction of compounds of formula 6 where P1 is BOC by treatment with HCl or $H_2SO_4$ in AcOH at a temperature between 0° C. and 150° C. optionally in an inert organic solvent.

Compounds of formula 5 may be prepared from compounds of formula 6 where P1 is benzyl or alkyl by a $H_2O$ elimination reaction, according to known methods by a person skilled in the art. Most favourable is the treatment of a compound of formula 6 with conc. HCl or $H_2SO_4$ in AcOH at a temperature between 0° C. and 150° C.

Alternatively, compounds of formula 5 may be prepared from compounds of formula 6 by treatment with $SOCl_2$, according to known methods by a person skilled in the art.

Alternatively, compounds of formula 5 may be formed by the reaction of compounds of formula 9 with a carboxylic acid derivative of formula t-Bu-C(O)—Z" where Z" is chloride, hydroxy, alkoxy or acyloxy at a temperature between 0° C. and 150° C. optionally in an inert organic solvent.

Compounds of formula 6 may be prepared from compounds of formula 7 by treatment of lithiated compounds of formula 7 with a piperidinone at a temperature between −100° C. and 0° C. optionally in an inert organic solvent, according to known methods by a person skilled in the art.

Compounds of formula 7 and formula 8 are known or may be made from known compounds by known methods.

Alternatively compounds of formula 1 may be formed by alkylation of compounds of formula 11 as described above for compounds of formula 3.

Compounds of formula 11 may be prepared from compounds of formula 10 where P1 is benzyl or alkyl by a dealkylation reaction, according to known methods by a person skilled in the art.

Compounds of formula 10 may be prepared from compounds of formula 9 by methods described above for the conversion of compounds of formula 2 to compounds of formula 1.

Compounds of formula 9 may be prepared from compounds of formula 6 by a $H_2O$ elimination reaction, according to known methods by a person skilled in the art. Most favourable is the treatment of a compound of formula 6 with aqueous HCl or $H_2SO_4$ in AcOH at a temperature between 0° C. and 150° C. or with a base in $H_2O$ and an appropriate solvent.

Certain compounds of formula 2, formula 3, formula 4, formula 5, formula 6, formula 9, formula 10 and formula 11 are novel and as such form a further aspect of the invention.

4-Hydroxy-piperidinyl compounds of the general formula 1 may be prepared according to the reactions of Scheme 2 using synthetic methodologies known by a person skilled in the art and as described above.

Scheme 2

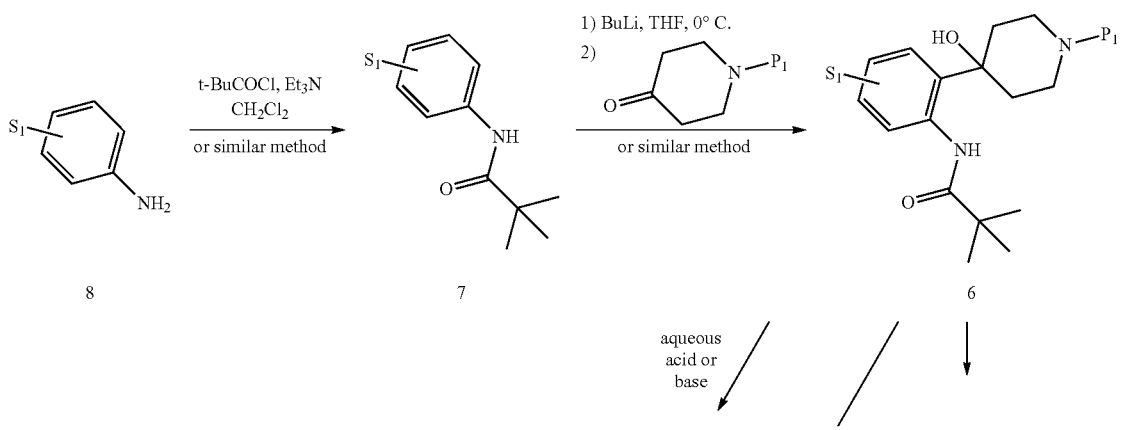

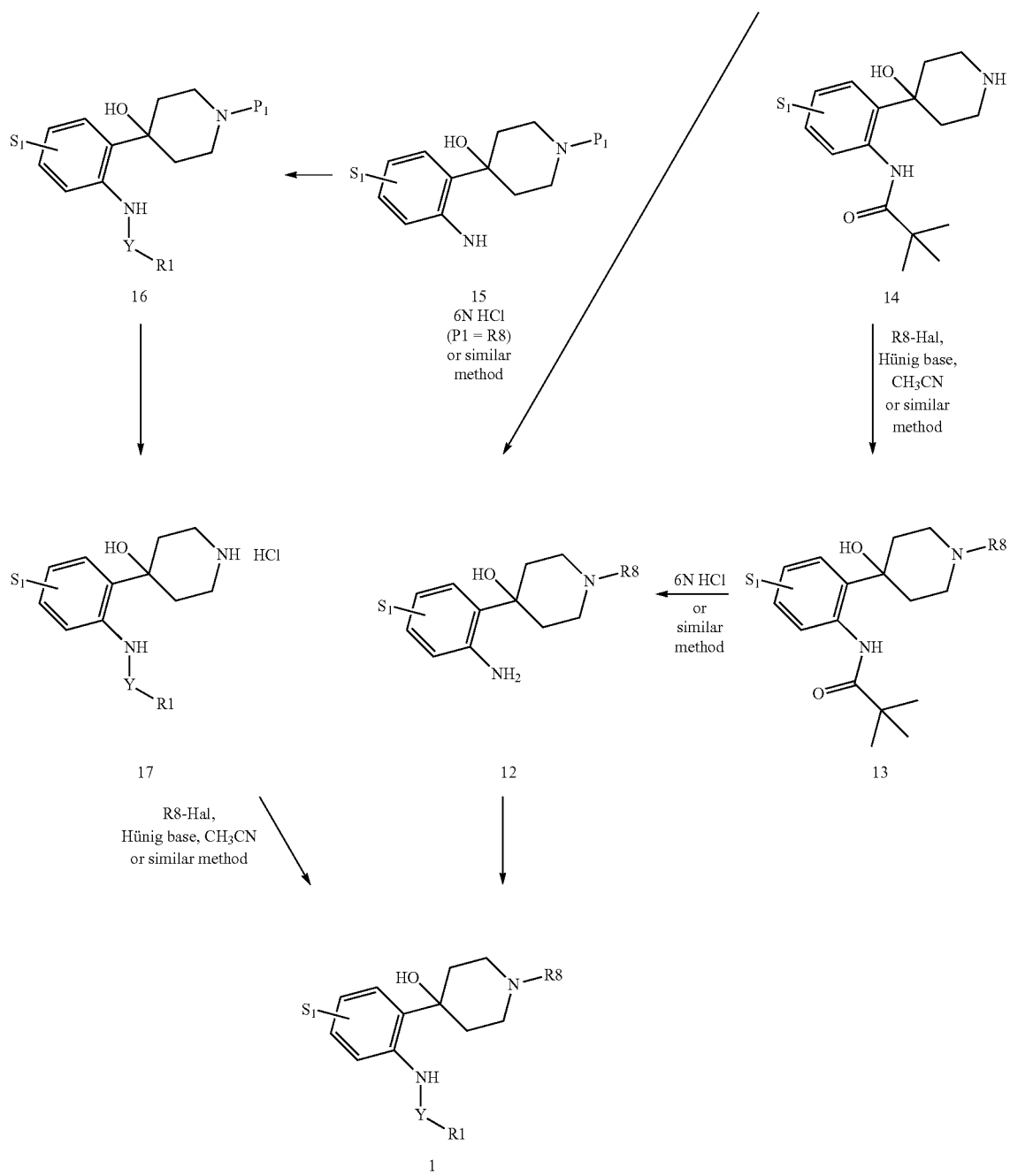

P1 is R8 or is a suitable protective group for example a group such as BOC, benzyl or alkyl and $S_1$ is the group $(R^4)n$.

The synthetic route shown in Scheme 2 may also be used for the preparation of some compounds of formula 1 wherein the ring

is a 5 or 6 membered heteroaromatic ring instead of the phenyl group.

Certain compounds of formula 12, formula 13, formula 14, formula 15, formula 16, and formula 17 are novel and as such form a further aspect of the invention.

Piperidinyl compounds of the general formula 1 may be prepared according to the reactions of Scheme 3 using synthetic methodologies known by a person skilled in the art and as described above.

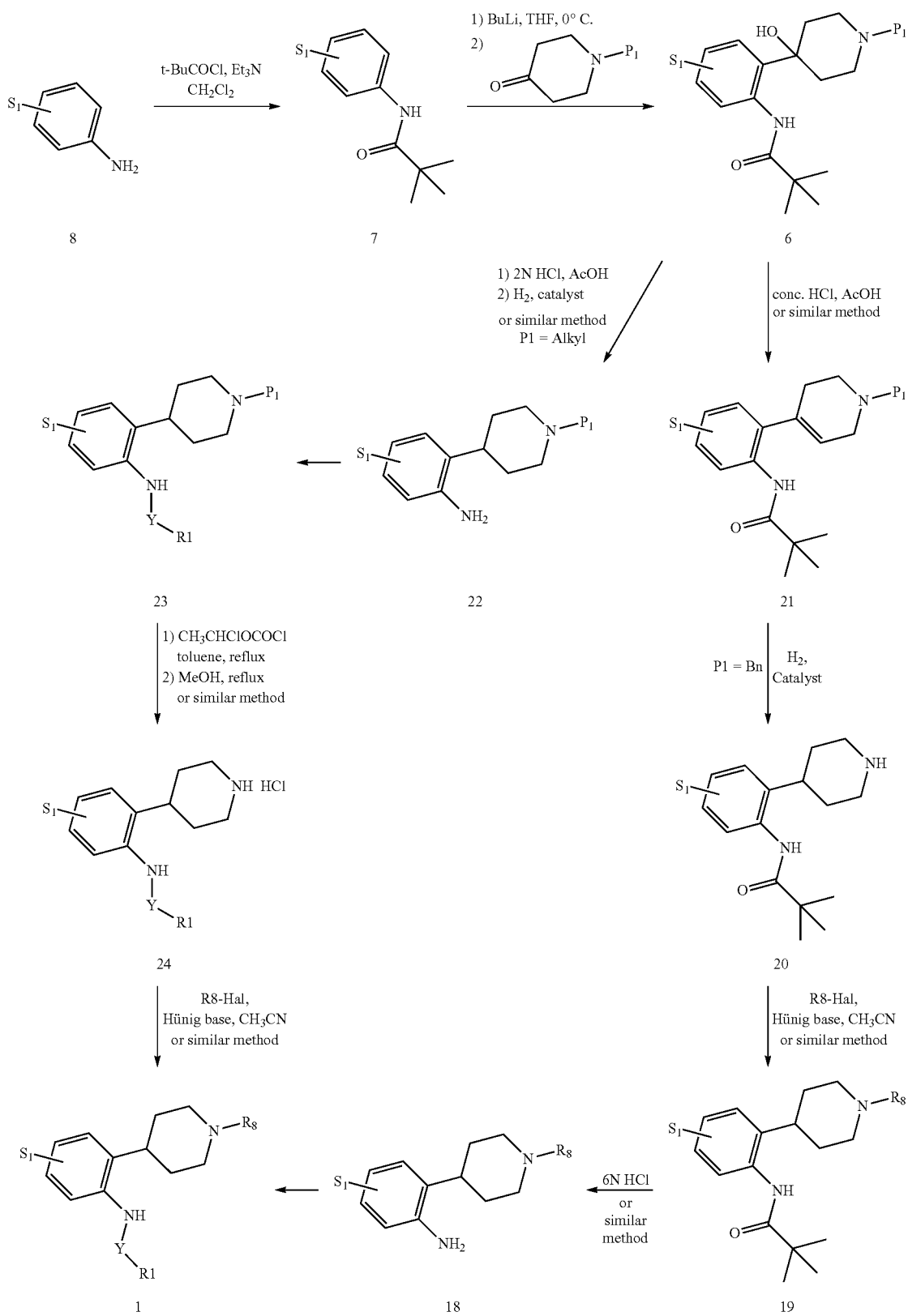

P1 is R8 or is a suitable protective group for example a group such as BOC, benzyl or alkyl and $S_1$ is the group $(R^4)n$.

The synthetic route shown in Scheme 3 may also be used for the preparation of some compounds of formula I wherein the ring

is a 5 or 6 membered heteroaromatic ring instead of the phenyl group.

Certain compounds of formula 18, formula 19, formula 20, formula 21, formula 22, formula 23 and formula 24 are novel and as such form a further aspect of the invention.

Compounds where the ring

is a 5 or 6 membered heteroaromatic ring instead of the phenyl group can be prepared by synthetic routes shown in Scheme 1-3 or many other routes and methods known to a person skilled in the art. For example 2H-pyrazol-3-yl derivatives can be prepared as shown in Scheme 4.

Scheme 4

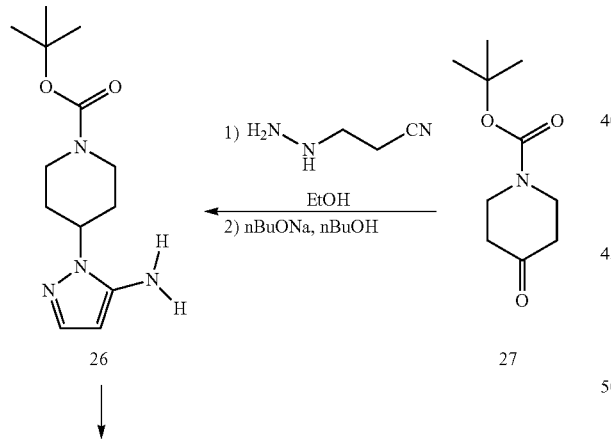

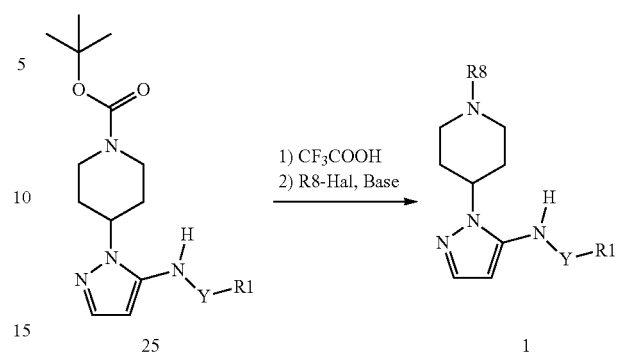

Certain compounds of formula 25 are novel and as such form a further aspect of the invention.

The skilled person will readily recognise that it is possible to convert one compound of formula 1 wherein R2 is H or an intermediate of Schemes 1-4 to other compounds of formula I or intermediates thereof. Examples of such transformations are given in Schemes 5, 6 and 7 in which the R groups have the meanings as defined for a compound of formula I above.

Scheme 5

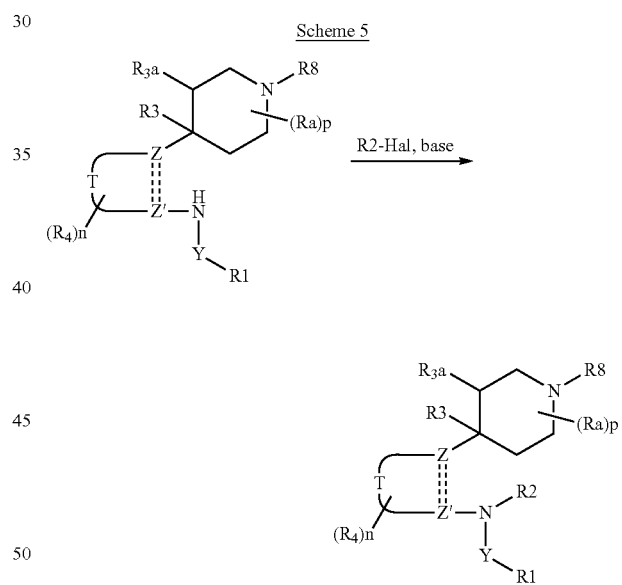

Scheme 6

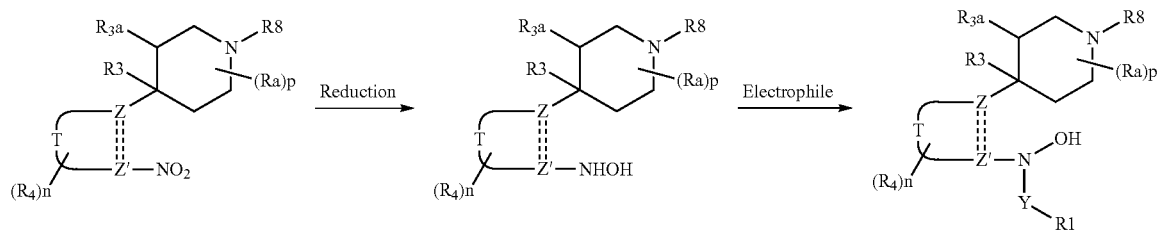

-continued
Scheme 7

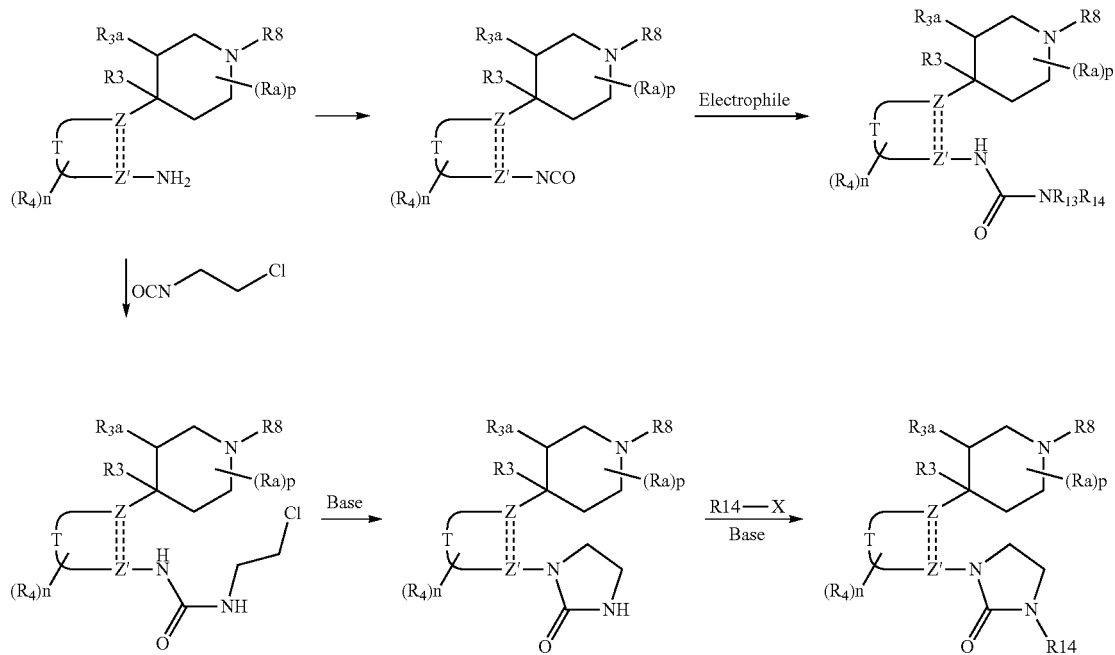

Alternatively piperidinyl-aniline derivatives of the general formula 1 may be prepared according to the reactions of Schemes 8-13 where S is the group (R⁴)n using synthetic methodologies known by a person skilled in the art and as described above.

A key step in these synthetic routes is a Suzuki coupling reaction to prepare tetrahydropyridin-4-yl-aniline derivatives. Other cross coupling reactions, such as Stille and Negishi couplings, may be applied as well. The boronate reagents may be prepared as described in the literature; for example P. R Eastwood, THL 41, 3705 (2000). Examples of coupling reactions are given in Examples 21-23 which describe the synthesis of the compounds in Tables EX23.1-EX23.11.

Scheme 8:

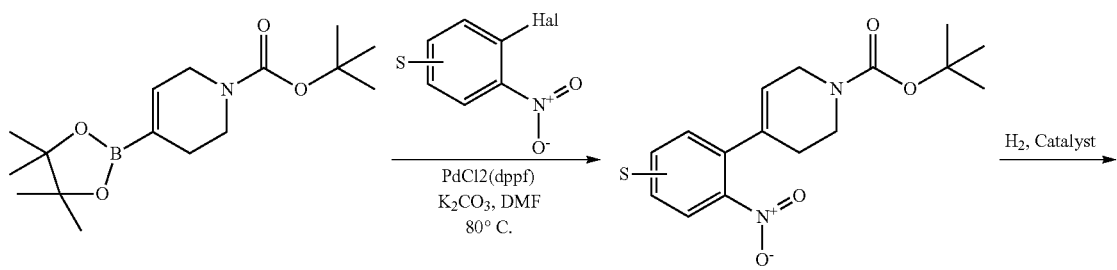

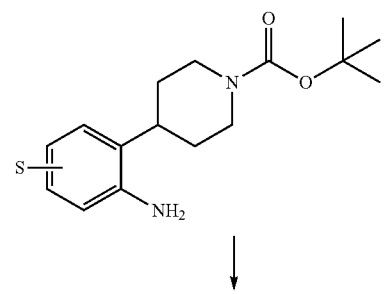

-continued
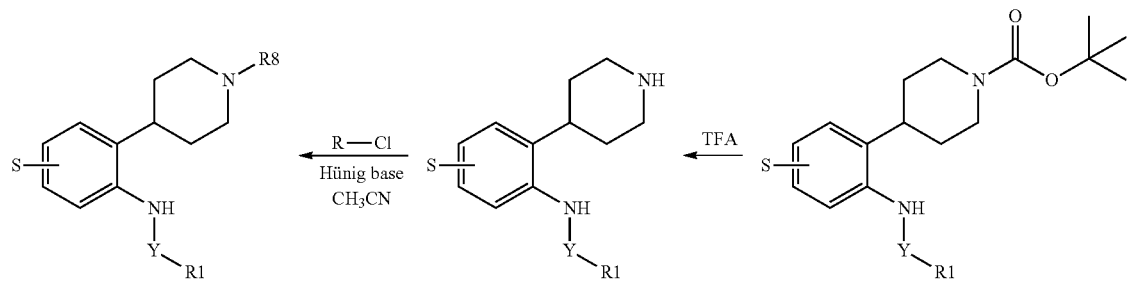
Scheme 9:
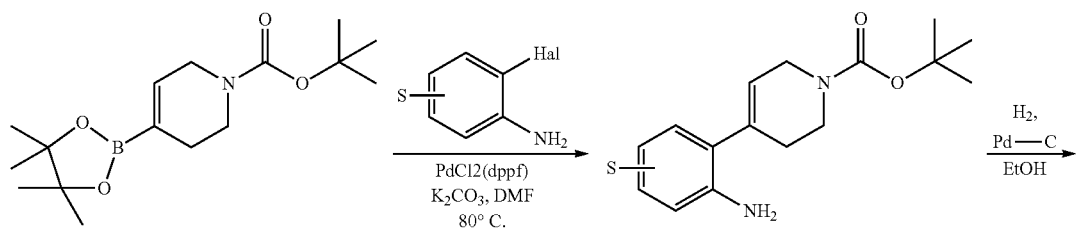
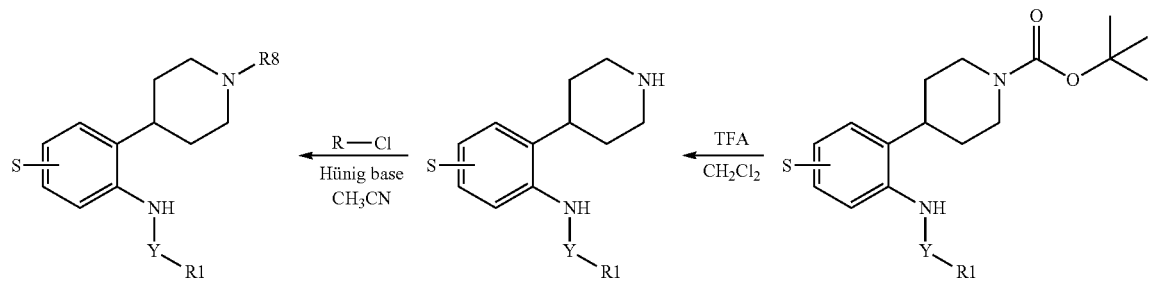

Scheme 10:
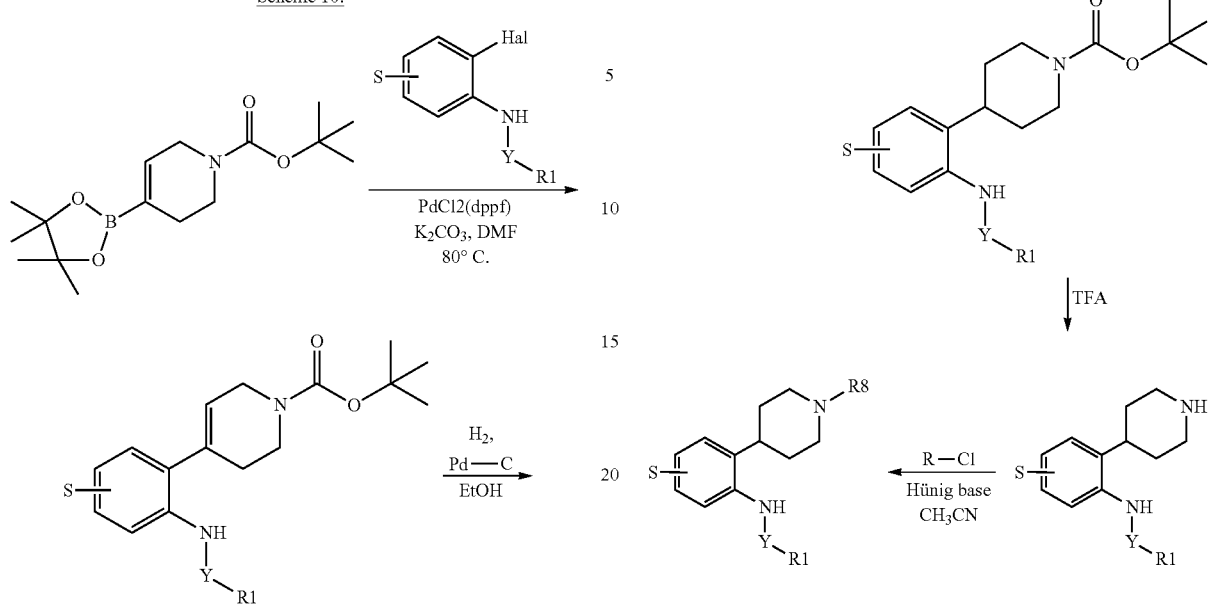
Scheme 11:
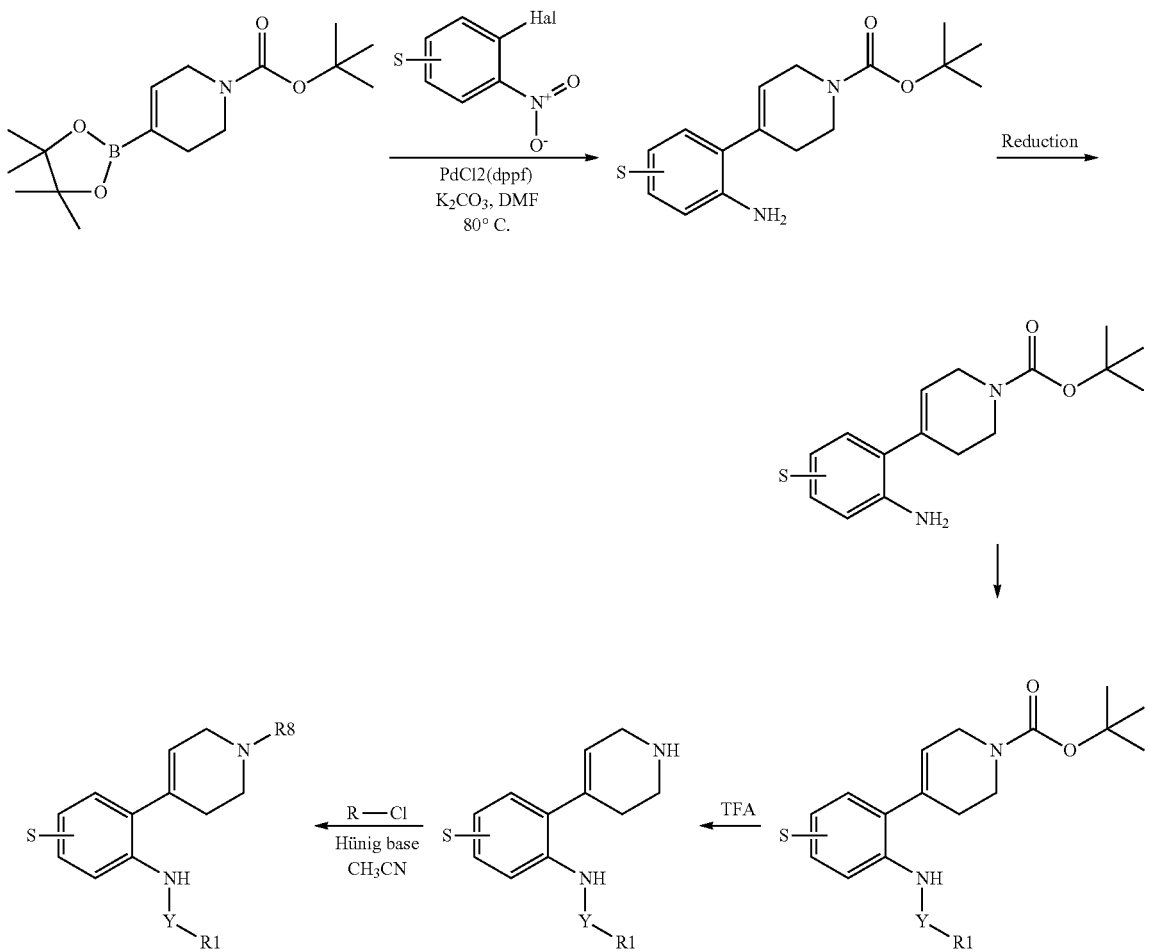

Scheme 12:

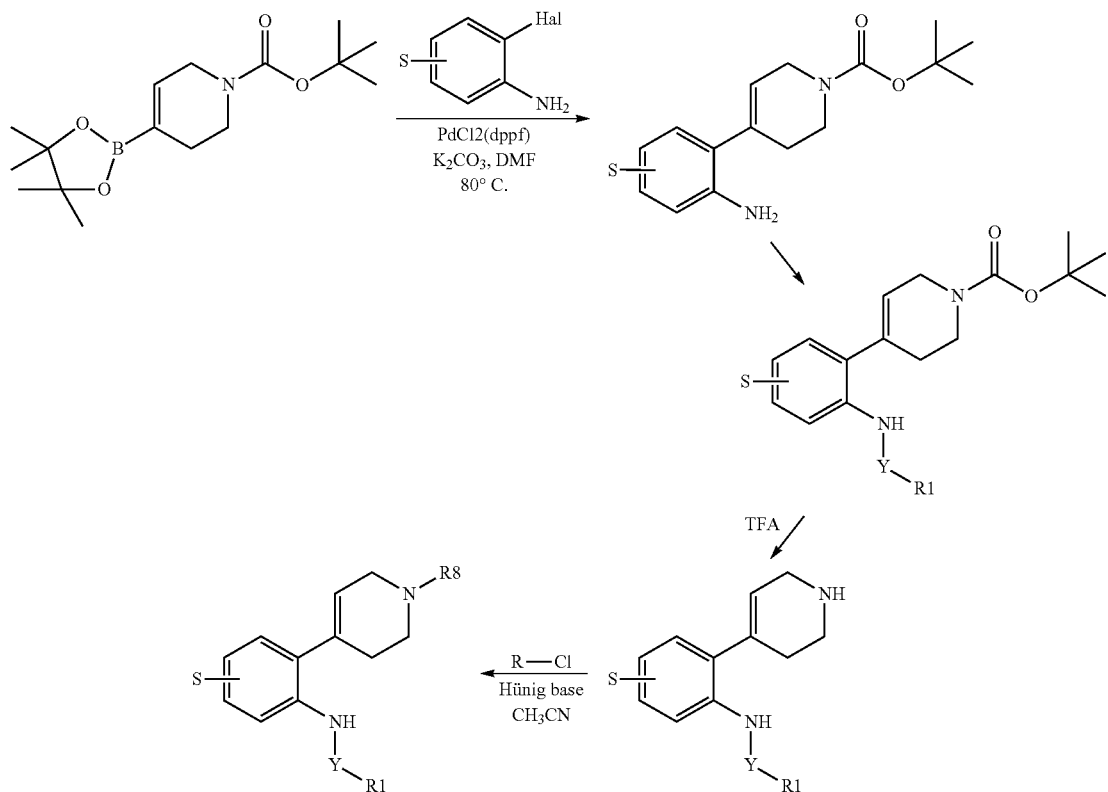

Scheme 13:

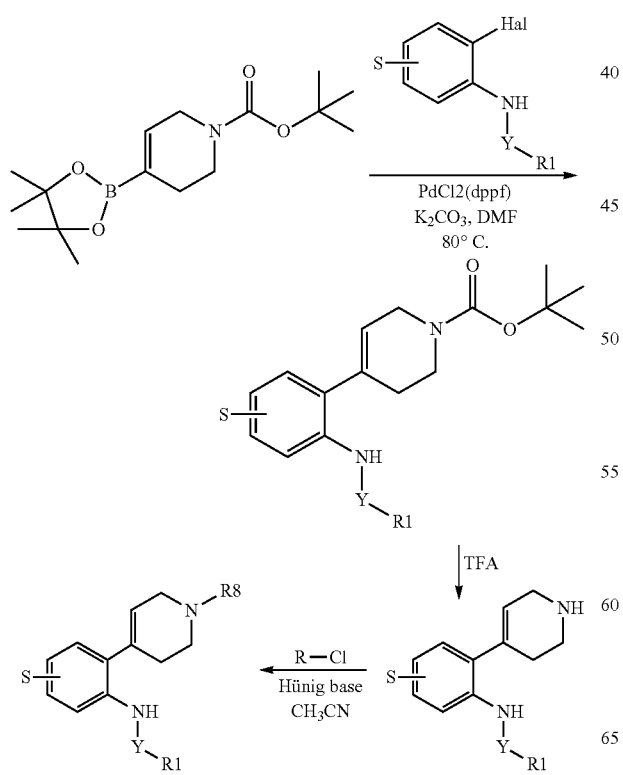

Instead of the BOC group other suitable protective groups may be used.

The synthetic routes shown in Scheme 8-13 may also be used for the preparation of compounds of formula I wherein the ring is a 5 or 6 membered heteroaromatic ring instead of the phenyl group.

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp.

(capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu, R. virginicus, R. hesperus*, and *R. santonensis*) and the Termitidae (for example *Globitermes sulphureus*), *Solenopsis geminata* (fire ant), *Monomorium pharaonic* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegan* (vinegar celworm), *Trichostrongylus* spp. (gastro intestinal nematodes) and *Deroceras reticulatum* (slug).

The invention therefore provides a method of combating and controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, or to a plant susceptible to attack by a pest, The compounds of formula (I) are preferably used against insects, acarines or nematodes.

The term "plant" as used herein includes seedlings, bushes and trees.

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

In a still further aspect the invention provides a method of combating and controlling pests at a locus which comprises treating the pests or the locus of the pests with an insecticidally, acaricidally, nematicidally or molluscicidally effective amount of a composition comprising a compound of formula (I). The compounds of formula (I) are preferably used against insects, acarines or nematodes.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifiying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurised, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilisers (for example nitrogen-, potassium- or phosphorus-containing fertilisers). Suitable formulation types include granules of fertiliser. The mixtures suitably contain up to 25% by weight of the compound of formula (I).

The invention therefore also provides a fertiliser composition comprising a fertiliser and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;

b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad or azadirachtin;

h) Hormones or pheromones;

i) Organochlorine compounds such as endosulfan, benzene hexachloride, DDT, chlordane or dieldrin;

j) Amidines, such as chlordimeform or amitraz;

k) Fumigant agents, such as chloropicrin, dichloropropane, methyl bromide or metam;

l) Chloronicotinyl compounds such as imidacloprid, thiacloprid, acetamiprid, nitenpyram or thiamethoxam;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr; or q) Pymetrozine.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxy-iminoacetamide (SSF-129), 4-bromo-2-cyano-N,N-dimethyl-6-trifluoromethylbenzimidazole-1-sulphonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy)propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulphate, copper tallate and Bordeaux mixture, cymoxanil, cyproconazole, cyprodinil, dcbacarb, di-2-pyridyl disulphide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)—N-benzyl-N([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-A1, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulphur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The invention is illustrated by the following Examples:

Mass spectra data were obtained for selected compounds of the following examples using LCMS: LC5: 254 nm—gradient 10% A to 100% B A=H2O+0.01% HCOOH B=CH3CN/CH3OH+0.01% HCOOH positive electrospray 150-1000 m/z.

EXAMPLE 1

This Example illustrates the preparation of N-(4-Chloro-2-{1-[(E)-3-(4-chloro-phenyl)-allyl]-4-hydroxy-piperidin-4-yl}-phenyl)-2,2-dimethyl-propionamide

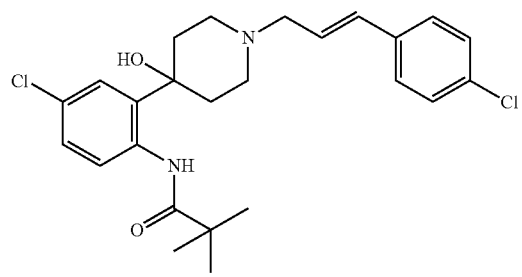 [SMILES: CC(C)(C)C(=O)Nc1ccc(Cl)cc1C1(O)CCN(C/C=C/c2ccc(Cl)cc2)CC1]

Step A: Preparation of
N-(4-Chloro-phenyl)-2,2-dimethyl-propionamide

To a solution of 4-chloroaniline (25.51 g) and triethylamine (69.73 ml) in chloroform (350 ml) were added 2,2-dimethyl-propionyl chloride (25.32 g) over a 30 minutes period. The resulting solution was stirred at r.t. for 1 hour, then water was added and the mixture extracted three times with ethyl acetate. The combined organic layers were dried over sodium sulfate and concentrated in vacuo to afford 35.8 g of product. M.p. 149-150° C.; Retention Time HPLC 2.83 min; MS (ES+) 212 (M+H$^+$).

Step B: Preparation of N-(4-Chloro-2-{1-[(E)-3-(4-chloro-phenyl)-allyl]-4-hydroxy-piperidin-4-yl}-phenyl)-2,2-dimethyl-propionamide A solution of n-buthyllithium in hexane (47.0 ml of a 1.6 M solution) was added dropwise to a solution of N-(4-chloro-phenyl)-2,2-dimethyl-propionamide (6.35 g) in dry THF (100 ml) at −5° C. under a N₂ atmosphere over 15 min. The resulting solution was stirred at 0° C. for 2 hours, and then a solution of 1-[(E)-3-(4-chloro-phenyl)-allyl]-piperidin-4-one (7.49 g) in THF (15 ml) was added dropwise to the above solution of the dianion at 0° C. over a 1 hour period. The reaction mixture was stirred for 2 hours at 0° C. and then overnight at r.t. The solution was then poured into ice water, made acidic with conc. HCl and extracted with ethyl acetate. The water layer was made basic and extracted three times with ethyl acetate. The combined organic layers were washed with water, dried over sodium sulfate and concentrated in vacuo. The residue was subjected to silica gel chromatography (hexane:ethyl acetate:triethyl amine 49:49:2) to afford the title product (6.2 g). M.p. 177-179° C.; Retention Time HPLC 2.19 min; MS (ES+) 461 (M+H⁺).

EXAMPLE 2

This Example illustrates the preparation of 4-Chloro-2-{1-[(E)-3-(4-chloro-phenyl)-allyl]-1,2,3,6-tetrahydro-pyridin-4-yl}-phenylamine and 4-(2-Amino-5-chloro-phenyl)-1-[(E)-3-(4-chloro-phenyl)-allyl]-piperidin-4-ol.

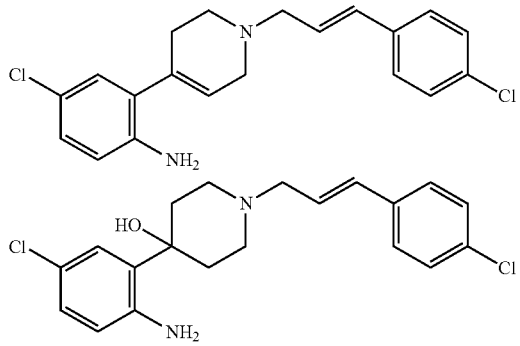

A suspension of N-(4-chloro-2-{1-[(E)-3-(4-chloro-phenyl)-allyl]-4-hydroxy-piperidin-4-yl}-phenyl)-2,2-dimethyl-propionamide (1.00 g) in 3N H2SO4 (7.5 ml) and DMSO (3 ml) was heated to reflux temperature for 48 hours. Then, water was added and the mixture extracted three times with CH₂Cl₂, the combined organic layers were dried over sodium sulfate and concentrated in vacuo. The residue was subjected to silica gel chromatography (CH₂Cl₂:MeOH 95:5) to afford 4-chloro-2-{1-[(E)-3-(4-chloro-phenyl)-allyl]-1,2,3,6-tetrahydro-pyridin-4-yl}-phenylamine (0.205 g; viscous oil; Retention Time HPLC 2.15 min; MS (ES+) 359 (M+H⁺) and 4-(2-amino-5-chloro-phenyl)-1-[(E)-3-(4-chloro-phenyl)-allyl]-piperidin-4-ol (0.182 g; M.p. 168-170° C.; Retention Time HPLC 1.95 min; MS (ES+) 377 (M+H⁺).

EXAMPLE 3

This Example illustrates the preparation 2-Chloro-N-(4-chloro-2-{1-[(E)-3-(4-chloro-phenyl)-allyl]-1,2,3,6-tetrahydro-pyridin-4-yl}-phenyl)-isonicotinamide

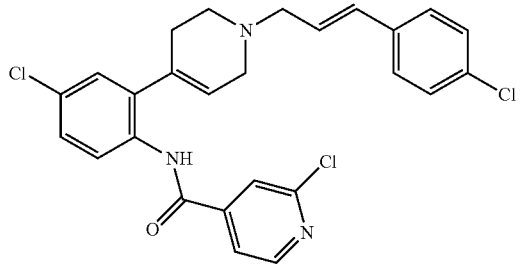 [SMILES: O=C(Nc1ccc(Cl)cc1C1=CCN(C/C=C/c2ccc(Cl)cc2)CC1)c1ccnc(Cl)c1]

To a solution of 4-chloro-2-{1-[(E)-3-(4-chloro-phenyl)-allyl]-1,2,3,6 tetrahydro-pyridin-4-yl}-phenylamine (60 mg) and triethylamine (0.059 ml) in CH₂Cl₂ (10 ml) were added 2-chloro-isonicotinoyl chloride (1.5 equivalents; as a 0.2 M solution in CH₂Cl₂) over a 10 minutes period. The resulting solution was stirred at r.t. for 2 hour, poured into saturated aqueous NaHCO₃ solution and the mixture extracted three times with CH₂Cl₂. The combined organic layers were dried over sodium sulfate and concentrated in vacuo. The residue was subjected to silica gel chromatography (hexane:ethyl acetate:triethyl amine 25:73:2) to afford the title product (28 mg). Viscous oil; Retention Time HPLC 2.28 min; MS (ES+) 500, 498 (M+H⁻).

EXAMPLE 4

This Example illustrates the preparation of N-[2-(1-Benzyl-4-hydroxy-piperidin-4-yl)-4-chloro-phenyl]-2,2-dimethyl-propionamide

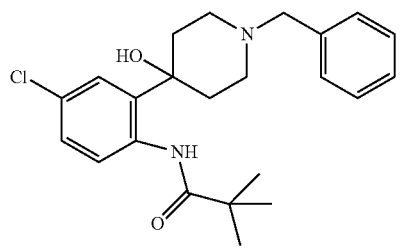 [SMILES: CC(C)(C)C(=O)Nc1ccc(Cl)cc1C1(O)CCN(Cc2ccccc2)CC1]

A solution of n-buthyllithium in hexane (22.6 ml of a solution containing 15% n-buthyllithium) was added dropwise to a solution of N-(4-chloro-phenyl)-2,2-dimethyl-propionamide (3.00 g) in dry THF (80 ml) at −5° C. under a N2 atmosphere over 15 min. The resulting solution was stirred at 0° C. for 2 hours, and then a solution of 1-benzyl-piperidin-4-one (2.67) in THF (4.5 ml) was added dropwise to the above solution of the dianion at 0° C. over a 1 hour period. The reaction mixture was stirred for 2 hours at 0° C. and then overnight at r.t. The solution was then poured into ice water, made acidic with conc. HCl and extracted with ethyl acetate. The water layer was made basic and extracted three times with ethyl acetate. The combined organic layers were washed with water, dried over sodium sulfate and concentrated in vacuo. The residue was recrystallized from ethyl acetate/THF to afford the title product (2.6 g). M.p. 252-255° C.

EXAMPLE 5

This Example illustrates the preparation of 2-(1-Benzyl-1,2,3,6-tetrahydro-pyridin-4-yl)-4-chloro-phenylamine and 4-(2-Amino-5-chloro-phenyl)-1-benzyl-piperidin-4-ol.

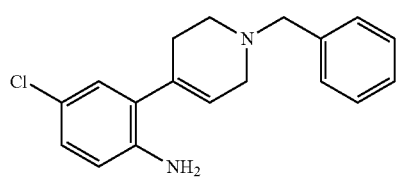

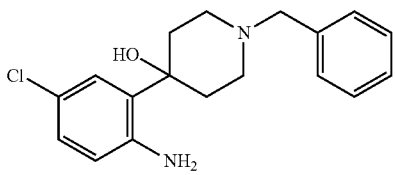

A suspension of N-[2-(1-benzyl-4-hydroxy-piperidin-4-yl)-4-chloro-phenyl]-2,2-dimethyl-propionamide (6.00 g) in n-BuOH (50 ml) and 6N HCl (120 ml) was heated to reflux temperature for 5 days. The solution was then poured into ice water, made acidic with conc. HCl and extracted with ethyl acetate. The water layer was made basic and extracted three times with $CH_2Cl_2$, dried over sodium sulfate and concentrated in vacuo. The residue was subjected to silica gel chromatography (hexane:ethyl acetate:triethyl amine 49:49:2) to afford 2-(1-benzyl-1,2,3,6-tetrahydro-pyridin-4-yl)-4-chloro-phenylamine (2.11 g; viscous oil; Retention Time HPLC 1.81 min; MS (ES+) 299 (M+H$^+$)) and 4-(2-amino-5-chloro-phenyl)-1-benzyl-piperidin-4-ol (2.11 g; viscous oil; Retention Time HPLC 1.58 min; MS (ES+) 317 (M+H$^-$).

EXAMPLE 6

This Example illustrates the preparation of N-[2-(1-Benzyl-1,2,3,6-tetrahydro-pyridin-4-yl)-4-chloro-phenyl]-2-chloro-isonicotinamide.

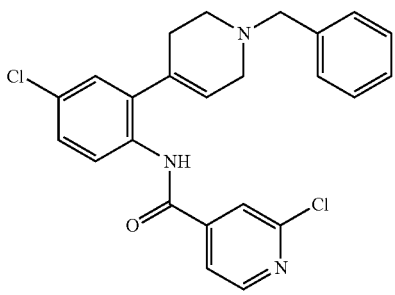 [SMILES: O=C(Nc1ccc(Cl)cc1C1=CCN(Cc2ccccc2)CC1)c1ccnc(Cl)c1]

To a solution of 2-(1-benzyl-1,2,3,6-tetrahydro-pyridin-4-yl)-4-chloro-phenylamine (500 mg) and triethylamine (0.350 ml) in $CHCl_3$ (25 ml) were added 2-chloro-isonicotinoyl chloride (1.2 equivalents; as a 1.0 M solution in $CH_2Cl_2$) over a 10 minutes period. The resulting solution was stirred at r.t. overnight, poured into saturated aqueous $NaHCO_3$ solution and the mixture extracted three times with $CH_2Cl_2$. The combined organic layers were dried over sodium sulfate and concentrated in vacuo. The residue was subjected to silica gel chromatography (hexane:ethyl acetate:triethyl amine 49:49:2) to afford the title product (595 mg). White solid; Retention Time HPLC 1.89 min; MS (ES+) 440, 438 (M+H$^+$).

EXAMPLE 7

This Example illustrates the preparation of 2-Chloro-N-[4-chloro-2-(1,2,3,6-tetrahydro-pyridin-4-yl)-phenyl]-isonicotinamide hydrochloride.

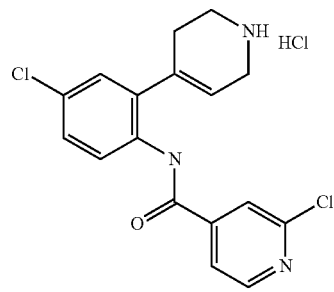 [SMILES: O=C(Nc1ccc(Cl)cc1C1=CCNCC1)c1ccnc(Cl)c1 ; Cl]

Step A: Preparation of 4-{5-Chloro-2-[(2-chloro-pyridine-4-carbonyl)-amino]phenyl}-3,6-dihydro-2H-pyridine-1-carboxylic acid 1-chloro-ethyl ester 1-Chloroethyl chloroformate (2.64 ml) was added to a suspension of N-[2-(1-benzyl-1,2,3,6-tetrahydro-pyridin-4-yl)-4-chloro-phenyl]-2-chloro-isonicotinamide (530 mg) in toluene (30 ml). After 15 min. the solution was heated to reflux for 16 hours, then poured into saturated aqueous NaHCO3 solution and the mixture extracted three times with $CH_2Cl_2$. The combined organic layers were dried over sodium sulfate and concentrated in vacuo to afford the crude title product (550 mg).

Step B: Preparation of 2-Chloro-N-[4-chloro-2-(1,2,3,6-tetrahydro-pyridin-4-yl)-phenyl]-isonicotinamide hydrochloride Crude 4-{5-chloro-2-[(2-chloro-pyridine-4-carbonyl)-amino]phenyl}-3,6-dihydro-2H-pyridine-1-carboxylic acid 1-chloro-ethyl ester (550 mg) was dissolved in methanol (25 ml) in and heated to reflux for 16 hours. Evaporation afforded the crude title product (465 mg). Retention Time HPLC 1.48 min; MS (ES+) 350, 348 (M+H$^+$).

EXAMPLE 8

This Example illustrates the preparation of 2-Chloro-N-(4-chloro-2-{1-[(E)-3-(4-fluoro-phenyl)-allyl]-1,2,3,6-tetrahydro-pyridin-4-yl}-phenyl)-isonicotinamide

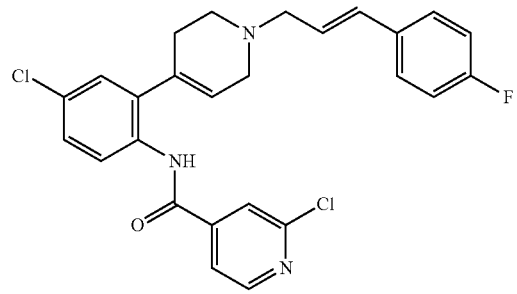 [SMILES: O=C(Nc1ccc(Cl)cc1C1=CCN(C/C=C/c2ccc(F)cc2)CC1)c1ccnc(Cl)c1]

Crude 4-{5-chloro-2-[(2-chloro-pyridine-4-carbonyl)-amino]-phenyl}-1-methyl-1,2,3,6-tetrahydro-pyridinium hydrochloride (69 mg; product obtained in Example 7) was dissolved in acetonitrile (5 ml) and treated with K₂CO₃ (87 mg). Then a solution of 1-((E)-3-chloro-propenyl)-4-fluoro-benzene in acetonitrile (1.0 ml) was added. After stirring for 3 hours at r.t. and 16 hours at 50° C. and heated to reflux for 16 hours the mixture was filtrated and concentrated in vacuo. The residue was subjected to silica gel chromatography (hexane:ethyl acetate:triethyl amine 74:24:2) to afford the title product (51 mg). Viscous oil; Retention Time HPLC 2.02 min; MS (ES+) 484, 482 (M+H⁺).

EXAMPLE 9

This Example illustrates the preparation of 2-Chloro-N-(4-chloro-2-{1-[(E)-3-(4-trifluoromethyl-phenyl)-allyl]-1,2,3,6-tetrahydro-pyridin-4-yl}-phenyl)-isonicotinamide

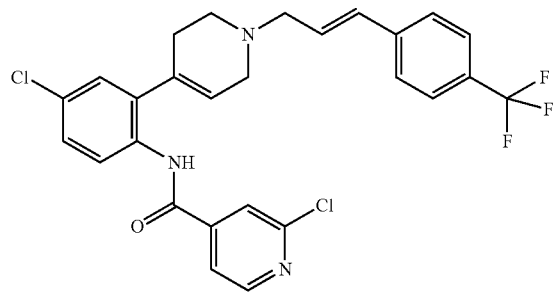 [SMILES: O=C(Nc1ccc(Cl)cc1C1=CCN(C/C=C/c2ccc(C(F)(F)F)cc2)CC1)c1ccnc(Cl)c1]

Crude 4-{5-chloro-2-[(2-chloro-pyridine-4-carbonyl)-amino]-phenyl}-1-methyl-1,2,3,6-tetrahydro-pyridinium hydrochloride (69 mg; product obtained in Example 7) was dissolved in acetonitrile (5 ml) and treated with Hünig's base (0.068 ml). Then a solution of 1-((E)-3-chloro-propenyl)-4-trifluoromethyl-benzene (53 mg) in CHCl₃ (1.0 ml) was added. After stirring for 3 hours at r.t. and 16 hours at 50° C. and heated to reflux for 16 hours the mixture was filtrated and concentrated in vacuo. The residue was subjected to silica gel chromatography (hexane:ethyl acetate:triethyl amine 74:24:2) to afford the title product (23 mg). Viscous oil; Retention Time HPLC 2.02 min; MS (ES+) 534, 532 (M+H⁺).

EXAMPLE 10

This Example illustrates the preparation of 2-Chloro-N-(4-chloro-2-{1-[(E)-3-(4-trifluoromethoxy-phenyl)-allyl]-1,2,3,6-tetrahydro-pyridin-4-yl}-phenyl)-isonicotinamide

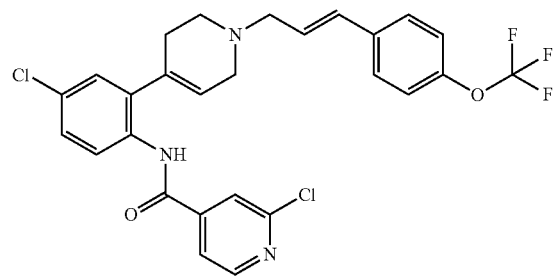 [SMILES: O=C(Nc1ccc(Cl)cc1C1=CCN(C/C=C/c2ccc(OC(F)(F)F)cc2)CC1)c1ccnc(Cl)c1]

Crude 4-{5-chloro-2-[(2-chloro-pyridine-4-carbonyl)-amino]-phenyl}-1-methyl-1,2,3,6-tetrahydro-pyridinium hydrochloride (69 mg; product obtained in Example 7) was dissolved in acetonitrile (5 ml) and treated with Hünig's base (0.068 ml). Then a solution of 1-((E)-3-chloro-propenyl)-4-trifluoromethoxy-benzene (56 mg) in CHCl₃ (1.0 ml) was added. After stirring for 3 hours at r.t. and 16 hours at 50° C. and heated to reflux for 16 hours the mixture was filtrated and concentrated in vacuo. The residue was subjected to silica gel chromatography (hexane:ethyl acetate:triethyl amine 74:24:2) to afford the title product (46 mg). Viscous oil; Retention Time HPLC 2.33 min; MS (ES+) 550, 548 (M+H⁺).

EXAMPLE 11

This Example illustrates the preparation of 2-Chloro-N-{4-chloro-2-[1-((E)-3-phenyl-allyl)1,2,3,6-tetrahydro-pyridin-4-yl]-phenyl}-isonicotinamide

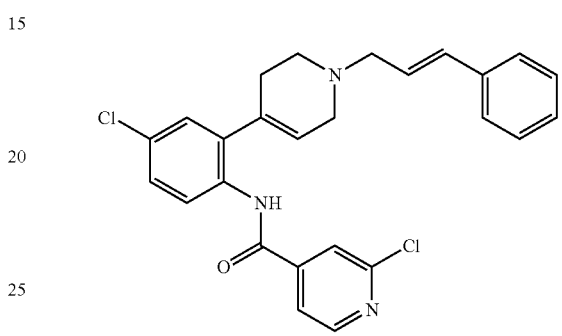

Crude 4-{5-chloro-2-[(2-chloro-pyridine-4-carbonyl)-amino]-phenyl}-1-methyl-1,2,3,6-tetrahydro-pyridinium hydrochloride (69 mg; product obtained in Example 7) was dissolved in acetonitrile (5 ml) and treated with Hünig's base (0.068 ml). Then a solution of ((E)-3-chloro-propenyl)-benzene (32 mg) in CHCl₃ (1.0 ml) was added. After stirring for 3 hours at r.t. and 16 hours at 50° C. and heated to reflux for 16 hours the mixture was filtrated and concentrated in vacuo. The residue was subjected to silica gel chromatography (hexane:ethyl acetate:triethyl amine 74:24:2) to afford the title product (36 mg). Viscous oil; Retention Time HPLC 2.01 min; MS (ES+) 466, 464 (M+H⁺).

EXAMPLE 12

This Example illustrates the preparation of N-[2-(1-Benzyl-4-hydroxy-piperidin-4-yl)-4-fluoro-phenyl]-2,2-dimethyl-propionamide

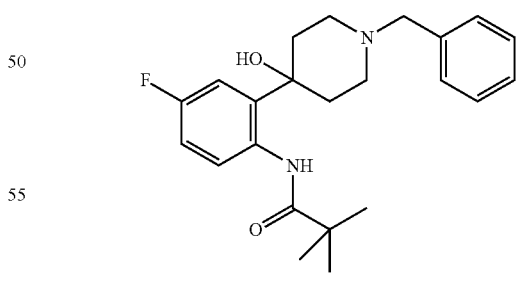

Step A: Preparation of N-(4-Fluoro-phenyl)-2,2-dimethyl-propionamide

To a solution of 4-fluoroaniline (50.0 g) and triethylamine (157 ml) in CH₂Cl₂ (700 ml) were added 2,2-dimethyl-propionyl chloride (58.0 ml) over a 30 minutes period. The resulting solution was stirred at r.t. for 2 hour, then water was added and the mixture extracted three times with ethyl acetate. The combined organic layers were dried over sodium sulfate and concentrated in vacuo to afford 86.0 g of the title compound. M.p. 124-125° C.; Retention Time HPLC 2.57 min; MS (ES+) 196 (M+H+).

Step B: Preparation of N-(4-Fluoro-2-{1-[(E)-3-(4-chloro-phenyl)-allyl]-4-hydroxy-piperidin-4-yl}-phenyl)-2,2-dimethyl-propionamide A solution of n-buthyllithium in hexane (80.0 ml of a 1.6 M solution) was added dropwise to a solution of N-(4-fluoro-phenyl)-2,2-dimethyl-propionamide (10.0 g) in dry THF (200 ml) at −5° C. under a N2 atmosphere over 15 min. The resulting solution was stirred at 0° C. for 2 hours, and then a solution of 1-benzyl-piperidin-4-one (9.20 ml) in THF (20 ml) was added dropwise to the above solution of the dianion at 0° C. over a 1 hour period. The reaction mixture was stirred for 2 hours at 0° C. and then overnight at r.t. The solution was the poured into ice water, made acidic with conc. HCl and extracted with ethyl acetate. The water layer was made basic and extracted three times with ethyl acetate. The combined organic layers were washed with water, dried over sodium sulfate and concentrated in vacuo. The residue was subjected to silica gel chromatography (hexane:ethyl acetate:triethyl amine 49:49:2) to afford the title product (8.3 g). M.p. 172-173° C.; Retention Time HPLC 1.47 min; MS (ES+) 385 (M+H+).

EXAMPLE 13

This Example illustrates the preparation of N-[2-(1-Benzyl-1,2,3,6-tetrahydro-pyridin-4-yl)-4-fluoro-phenyl]-2,2-dimethyl-propionamide

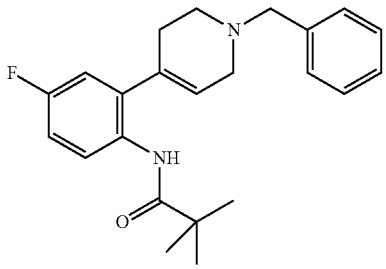 [SMILES: CC(C)(C)C(=O)Nc1ccc(F)cc1C1=CCN(Cc2ccccc2)CC1]

A solution of N-(4-fluoro-2-{1-[(E)-3-(4-chloro-phenyl)-allyl]-4-hydroxy-piperidin-4-yl}-phenyl)-2,2-dimethyl-propionamide (4.00 g) in conc HCl (2.4 ml) and conc. AcOH (30 ml) was heated to reflux temperature for 24 hours. Then, water was added and the mixture extracted three times with CH2Cl2, the combined organic layers were dried over sodium sulfate and concentrated in vacuo. The residue was dissolved in CH2Cl2 (30 ml) and treated with triethylamine (2.8 ml) and 2,2-dimethyl-propionyl chloride (0.61 ml). The resulting solution was stirred at r.t. for 2 hour, then water was added and the mixture extracted three times with ethyl acetate. The combined organic layers were dried over sodium sulfate and concentrated in vacuo. The residue was subjected to silica gel chromatography (hexane:ethyl acetate:triethyl amine 79:19:2) to afford the title product (3.1 g). Viscous oil; Retention Time HPLC 2.00 min; MS (ES+) 367 (M+H+).

EXAMPLE 14

This Example illustrates the preparation of N-(4-Fluoro-2-piperidin-4-yl-phenyl)-2,2-dimethyl-propionamide

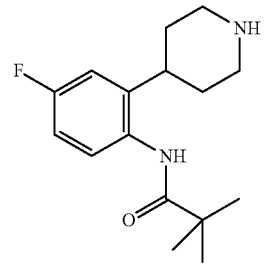 [SMILES: CC(C)(C)C(=O)Nc1ccc(F)cc1C1CCNCC1]

A suspension of N-[2-(1-Benzyl-1,2,3,6-tetrahydro-pyridin-4-yl)-4-fluoro-phenyl]-2,2-dimethyl-propionamide (500 mg) and 10% Pd—C (50 mg) in EtOH (50 ml) was stirred in a H2 atmosphere for 16 hours. Then, the mixture was filtered and the resulting solution concentrated in vacuo to afford the title compound (380 mg). Viscous oil; Retention Time HPLC 1.61 min; MS (ES+) 279 (M+H+).

EXAMPLE 15

This Example illustrates the preparation of N-(2-{1-[(E)-3-(4-Chloro-phenyl)-allyl]-piperidin-4-yl}-4-fluoro-phenyl)-2,2-dimethyl-propionamide

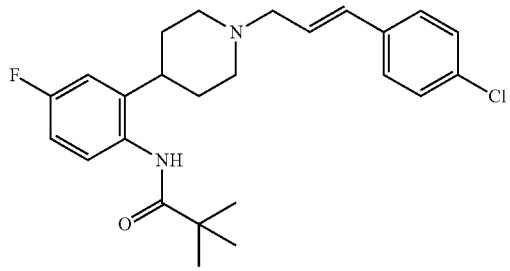 [SMILES: CC(C)(C)C(=O)Nc1ccc(F)cc1C1CCN(C/C=C/c2ccc(Cl)cc2)CC1]

N-(4-Fluoro-2-piperidin-4-yl-phenyl)-2,2-dimethyl-propionamide (380 mg) was dissolved in CHCl3 (20 ml) and treated with triethyl amine (0.260 mg). Then, a solution of 1-((E)-3-chloro-propenyl)-4-chloro-benzene (255 mg) was added. After stirring for 16 hours at r.t. the mixture was filtrated and concentrated in vacuo. The residue was subjected to silica gel chromatography (hexane:ethyl acetate:triethyl amine 74:24:2) to afford the title product (380 mg). M.p. 174-176° C.; Retention Time HPLC 2.37 min; MS (ES+) 4.29 (M+H+).

EXAMPLE 16

This Example illustrates the preparation of 2-{1-[(E)-3-(4-Chloro-phenyl)-allyl]-piperidin-4-yl}-4-fluoro-phenylamine

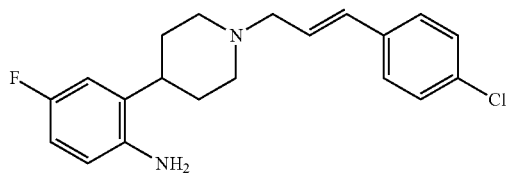 [SMILES: Nc1ccc(F)cc1C1CCN(C/C=C/c2ccc(Cl)cc2)CC1]

A solution of N-(2-{1-[(E)-3-(4-chloro-phenyl)-allyl]-piperidin-4-yl}-4-fluoro-phenyl)-2,2-dimethyl-propionamide (315 mg) in 6N HCl (25 ml) and conc. AcOH (25 ml) was heated to reflux temperature for 20 hours. Then, the solution was made basic (pH=12) by the addition of solid NaOH, and extracted three times with CH₂Cl₂. The combined organic layers were dried over sodium sulfate and concentrated in vacuo. The residue was subjected to silica gel chromatography (hexane:ethyl acetate:triethyl amine 79:19:2) to afford the title product (201 mg). M.p. 93-94° C.; Retention Time HPLC 2.18 min; MS (ES+) 345 (M+H⁺).

EXAMPLE 17

This Example illustrates the preparation of 2-Chloro-N-(2-{1-[(E)-3-(4-chloro-phenyl)-allyl]-piperidin-4-yl}-4-fluoro-phenyl)-isonicotinamide

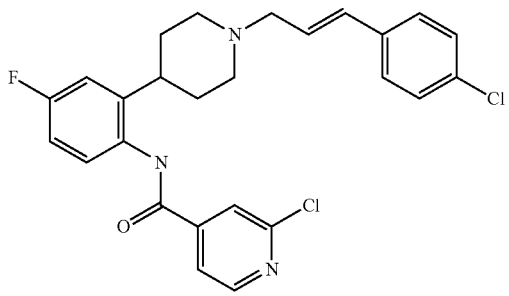 [SMILES: O=C(Nc1ccc(F)cc1C1CCN(C/C=C/c2ccc(Cl)cc2)CC1)c1ccnc(Cl)c1]

To a solution of 2-{1-[(E)-3-(4-chloro-phenyl)-allyl]-piperidin-4-yl}-4-fluoro-phenylamine (40 mg) and triethylamine (0.025 ml) in CHCl₃ (10 ml) were added 2-chloro-isonicotinoyl chloride (1.2 equivalents; as a 1.0 M solution in CH₂Cl₂) over a 10 minute period. The resulting solution was stirred at r.t. over night, poured into saturated aqueous NaHCO₃ solution and the mixture extracted three times with CH₂Cl₂. The combined organic layers were dried over sodium sulfate and concentrated in vacuo. The residue was subjected to silica gel chromatography (ethyl acetate:methanol 9:1) to afford the title product (43 mg). White solid; Retention Time HPLC 2.36 min; MS (ES+) 486, 484 (M+H⁺).

According to this method the following compounds have been prepared starting from 2-{1-[(E)-3-(4-chloro-phenyl)-allyl]-piperidin-4-yl}-4-fluoro-phenylamine:
2,6-Dichloro-N-(2-{1-[(E)-3-(4-chloro-phenyl)-allyl]-piperidin-4-yl}-4-fluoro-phenyl)-isonicotinamide
White solid; Retention Time HPLC 2.67 min; MS (ES+) 520, 518 (M+H⁺).

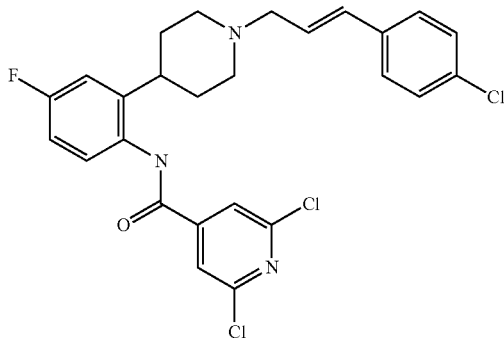 [SMILES: O=C(Nc1ccc(F)cc1C1CCN(C/C=C/c2ccc(Cl)cc2)CC1)c1cc(Cl)nc(Cl)c1]

N-(2-{1-[(E)-3-(4-Chloro-phenyl)-allyl]-piperidin-4-yl}-4-fluoro-phenyl)-isonicotinamide
White solid; Retention Time HPLC 2.07 min; MS (ES+) 450 (M+H⁺).

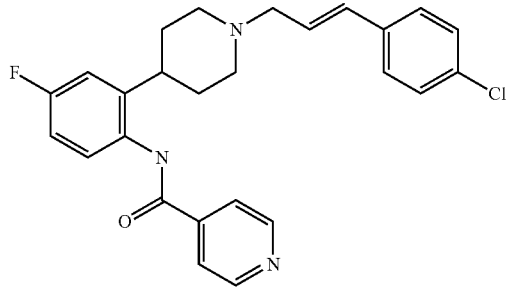 [SMILES: O=C(Nc1ccc(F)cc1C1CCN(C/C=C/c2ccc(Cl)cc2)CC1)c1ccncc1]

EXAMPLE 18

This Example illustrates the preparation of 4-(5-Amino-pyrazol-1-yl)-piperidine-1-carboxylic acid tert-butyl ester

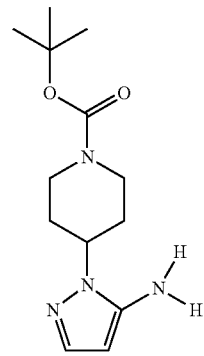 [SMILES: CC(C)(C)OC(=O)N1CCC(n2nccc2N)CC1]

A solution of 2-cyanoethyl hydrazine (5.1 g) in absolute ethanol (20 ml) was added dropwise to a solution of N—BOC-piperidone (12 g) in absolute ethanol at room temperature. The resulting solution was stirred at room temperature for 1 hour then the solvent was removed in vacuo. The resulting oil was then added to a solution of sodium butoxide (prepared from 2.8 g of sodium and 60 ml of n-butanol) and the reaction mixture was refluxed for 3 hours, cooled to room temperature, washed with saturated aqueous ammonium chloride then with water, and the solvent was removed in vacuo. Precipitation from hexane afforded the title compound (11.5 g) as a yellow powder. M.p. 145-147° C.; ¹H NMR (400 MHz, CDCl₃) 1.5 (s, 9H), 1.9 (m, 2H), 2.1 (m, 2H), 2.9 (m, 2H), 3.5 (m, 2H), 4.0 (m, 1H), 4.2 (m, 2H), 5.5 (s, 1H), 7.3 (s, 1H).

EXAMPLE 19

This Example illustrates the preparation of 4-{5-[(2-Chloro-pyridine-4-carbonyl)-amino]-pyrazol-1-yl}-piperidine-1-carboxylic acid tert-butyl ester

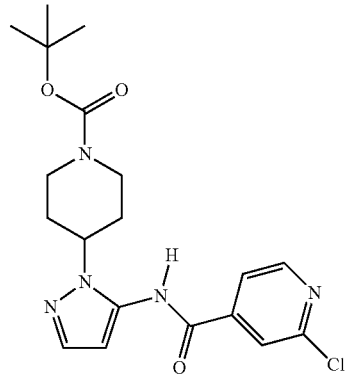 [SMILES: CC(C)(C)OC(=O)N1CCC(n2nccc2NC(=O)c2ccnc(Cl)c2)CC1]

Triethylamine (2.8 ml) was added to a stirred solution of the compound obtained in example 18 (2.66 g) in dichloromethane (100 ml); the solution was cooled to 0° C. and 2-chloroisonicotinoyl chloride (prepared from 2.05 g of 2-chloroisonicotinic acid and 1.46 ml of oxalyl chloride in 50 ml dichloromethane) was added. The resulting mixture was stirred at room temperature for 12 hours, poured into water, extracted two times with dichloromethane; the combined organic layers were dried over sodium sulfate and concentrated in vacuo. The residue was precipitated from ethyl acetate/hexane to afford the title compound as a pale yellow powder (3.4 g). M.p. 209-210° C.; $^1$H NMR (400 MHz, CDCl$_3$) 1.5 (s, 9H), 1.9 (m, 2H), 2.1 (m, 2H), 2.9 (m, 2H), 3.5 (m, 2H), 4.0 (m, 1H), 4.2 (m, 2H), 6.1 (s, 1H), 7.5 (s, 1H), 7.6 (m, 1H), 7.7 (s, 1H), 8.2 (sm, 1H), 8.5 (d, J=6 Hz, 1H).

EXAMPLE 20

This Example illustrates the preparation of 2-Chloro-N-(2-{1-[3-(4-chloro-phenyl)-allyl]-piperidin-4-yl}-2H-pyrazol-3-yl)-isonicotinamide

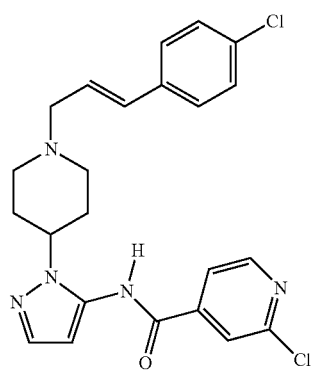 [SMILES: O=C(Nc1ccnn1C1CCN(C/C=C/c2ccc(Cl)cc2)CC1)c1ccnc(Cl)c1]

A solution of the compound obtained in Example 19 (2.7 g) in dichloromethane (150 ml) was treated with trifluoroacetic acid (3.8 ml) for 6 hours at room temperature and the solvent was removed in vacuo. The residue was dissolved in acetonitrile (100 ml), N,N-diisopropylethylamine (9 ml) and 4-chlorocinnamyl chloride (1.9 g) were added. The resulting solution was stirred for 24 hours at room temperature, the solvent was removed in vacuo and the residue was subjected to silica gel chromatography (ethyl acetate:methanol 95:5) to afford a product identified as 2-{1-[3-(4-Chloro-phenyl)-allyl]-piperidin-4-yl}-2H-pyrazol-3-ylamine. This product was re-acylated using 1.05 g of 2-chloroisonicotinoyl chloride, 0.7 ml of triethylamine in 50 ml dichloromethane according to the method described in Step B. Silica gel chromatography of the residue (ethyl acetate:methanol 95:5) finally afforded the title product (370 mg). M.p. 69-70° C. $^1$H NMR (400 MHz, CDCl$_3$) 1.9-2.4 (m, 6H), 3.0 (d, J=11.6 Hz, 2H), 3.1 (d, J=6.4 Hz, 2H), 3.9 (m, 1H), 6.2 (m, 2H), 6.5 (d, J=16.0 Hz, 1H), 7.3 (m, 4H), 7.5 (s, 1H), 7.6 (s, 1H), 7.7 (br s, 1H), 8.6 (d, J=4.8 Hz, 1H). Retention Time HPLC 2.32 min; MS (ES+) 456/458 (M+H$^+$).

The invention is further illustrated by the following Examples applying cross coupling reactions.

EXAMPLE 21

This Example illustrates the preparation of 2-Chloro-N-{1'-[(E)-3-(4-chloro-phenyl)-allyl]-1',2',3',4',5',6'-hexahydro-[2,4']bipyridinyl-3-yl}-isonicotinamide.

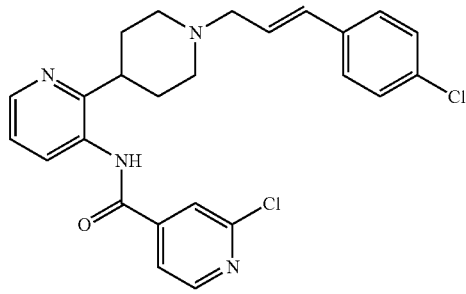 [SMILES: O=C(Nc1cccnc1C1CCN(C/C=C/c2ccc(Cl)cc2)CC1)c1ccnc(Cl)c1]

Step A: 1-(t-Butoxycarbonyl)-4-tributylstannyl-1,2,3,6-tetrahydropyridine (2.12 g, prepared in 2 steps from 1-(t-butoxycarbonyl)-piperidin-4-one according to WO 0123381) was dissolved in toluene (45 ml) in a dried, nitrogen-flushed flask. 2-Chloro-3-nitropyridine (712 mg) and palladium tetrakis(triphenylphosphine) (130 mg) were added and the solution was heated at 110° C. for 16 hours. The reaction mixture was cooled to room temperature, the solvent removed in vacuo and the residue partitioned between ethyl acetate (100 ml) and NaOH 2N (100 ml). After 30 min stirring at room temperature, the organic layer was separated, washed with NaOH 2N then water, dried over sodium sulfate and concentrated in vacuo. The residue was subjected to silica gel chromatography (ethyl acetate:cyclohexane 3:7) to afford 3-nitro-3',6'-dihydro-2'H-[2,4']bipyridinyl-1'-carboxylic acid tert-butyl (1.1 g) as light yellow crystals. M.p. 104-105° C.; $^1$H NMR (400 MHz, CDCl$_3$) 1.4 (s, 9H), 2.5 (m, 2H), 3.6 (m, 2H), 4.0 (m, 214), 5.9 (m, 1H), 7.3 (dd, J=4.8, 8.4 Hz, 1H), 8.0 (d, J=8.4 Hz, 1H), 8.7 (d, J=4.8 Hz, 1H); MS (ES+) 206 (MH+—BOC), 248 (MH+-isoprene).

Step B: Hydrazine monohydrate (0.4 ml) was added to a suspension of Raney nickel (50% slurry in water, 200 mg) and the product obtained in Step A (240 mg) in ethanol (10 ml). After 4 hours stirring, the reaction mixture was filtered over Hyflo and the solvent removed in vacuo. The residue was dissolved in ethyl acetate, dried over sodium sulfate, filtered and concentrated in vacuo to afford 3-amino-3',6'-dihydro-2'H-[2,4']bipyridinyl-1'-carboxylic acid tert-butyl ester (200 mg) as white crystals. M.p. 104-105° C.; $^1$H NMR (400 MHz, CDCl$_3$) 1.4 (s, 9H), 2.5 (m, 2H), 3.6 (m, 2H), 3.7 (brs, 2H), 4.0 (m, 2H), 5.9 (m, 1H), 6.9 (m, 2H), 8.0 (m, 1H); MS (ES+) 176 (MH+—BOC), 220 (MH+-isoprene), 276 (MH+).

Step C: The product obtained in Step B (815 mg) was reduced by transfer hydrogenation using 10% Pd/C (200 mg) and ammonium formate (935 mg) in ethanol (40 ml) at 60° C. for 45 min. After filtration over Hyflo, the solvent was removed in vacuo. The residue was portioned between ethyl acetate and water, the organic layer separated, washed with water, dried over sodium sulfate and concentrated in vacuo to give 3-amino-3',4',5',6'-dihydro-2'H-[2,4']bipyridinyl-1'-carboxylic acid tert-butyl ester (785 mg) as an oil. $^1$H NMR (400 MHz, CDCl$_3$) 1.4 (s, 9H), 1.6 (m, 4H), 2.7 (m, 3H), 3.5 (brs, 2H), 4.0 (m, 2H), 6.9 (m, 2H), 8.0 (m, 1H); MS (ES+) 178 (MH+—BOC), 222 (MH+-isoprene), 278 (MH+).

Step D: sodium bicarbonate (714 mg) was added to a stirred solution of the compound obtained in Step C (785 mg) in dichloromethane (30 ml); the solution was then treated with 2-chloro-isonicotinoyl chloride (500 mg) and the resulting mixture was stirred at room temperature for 1 hour, poured into water, extracted two times with dichloromethane, the combined organic layers were dried over sodium sulfate and concentrated in vacuo to afford 3-[(2-Chloro-pyridine-4-carbonyl)-amino]-3',4',5',6'-tetrahydro-2'H-[2,4']bipyridinyl-1'-carboxylic acid tert-butyl ester (1.2 g).

Step E: A solution of the compound obtained in Step D (834 mg) in dichloromethane (40 ml) was treated with trifluoroacetic acid (4 ml) for 5 hours at room temperature. The reaction mixture was concentrated in vacuo and then dried under high vacuum for 1 hour. The residue was dissolved in acetonitrile (40 ml), diisopropylethylamine (1.8 ml) and 4-chlorocinnamyl chloride (380 mg) were added. The solution was stirred 20 hours at room temperature, the solvent was removed in vacuo and the residue was subjected to silica gel chromatography (ethyl acetate:methanol 95:5) to afford the title product (409 mg) as a yellow solid. M.p. 78-80° C.; NMR (400 MHz, CDCl$_3$) 1.9 (m, 2H), 2.2 (m, 4H), 2.8 (m, 1H), 3.2 (d, J=9 Hz, 2H), 3.3 (m, 2H), 6.2 (dt, J=18, 9 Hz, 1H), 6.5 (d, J=18 Hz, 1H), 7.1-7.3 (m, 5H), 7.6 (d, J=4.4 Hz, 1H), 7.7 (s, 1H), 7.9 (m, 1H, NH), 8.0 (d, J=7.6 Hz, 1H), 8.6 (d, J=3.6 Hz, 1H), 8.7 (d, J=5.5 Hz, 1H); Retention Time HPLC 1.53 min; MS (ES+) 467/469 (M+H⁻).

EXAMPLE 22

This Example illustrates the preparation of 2-Chloro-N-{1'-[(E)-3-(4-chloro-phenyl)-allyl]-1',2',3',6'-hexahydro-[2,4']bipyridinyl-3-yl}-isonicotinamide.

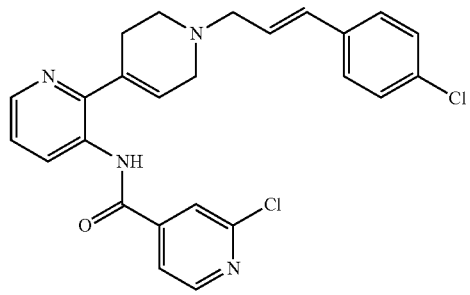 [SMILES: O=C(Nc1cccnc1C1=CCN(C/C=C/c2ccc(Cl)cc2)CC1)c1ccnc(Cl)c1]

3-amino-3',6'-dihydro-2'H-[2,4']bipyridinyl-1'-carboxylic acid tert-butyl ester (Example 1, Step B, 205 mg) was treated as described in Example 1, steps D and E to afford the title product (182 mg) as a yellow solid. M.p. 75-77° C.; ¹H NMR (400 MHz, CDCl$_3$) 1.8 (m, 2H), 2.7 (m, 2H), 2.8 (m, 2H), 3.2 (m, 2H), 3.3 (m, 2H), 6.0 (s, 1H), 6.2 (dt, J=18, 9 Hz, 1H), 6.5 (d, J=18 Hz, 1H), 7.1-7.3 (m, 6H), 7.6 (m, 1H), 7.7 (s, 1H), 7.7 (s, 1H), 8.3 (d, J=3.6 Hz, 1H), 8.5 (d, J=5.5 Hz, 1H), 8.8 (m, 1H, NH); Retention Time HPLC 1.51 min; MS (ES+) 465/467 (M+H⁺).

The following compounds were prepared according to procedures analogous to those described in Example 22:

| Compound Name | Structure | M.p (° C.) | MH⁺ | Retention Time (min) |
|---|---|---|---|---|
| 2-chloro-N-{1'-[(E)-3-(4-chloro-phenyl)-allyl]-1',2',3',6'-hexahydro-[2,4']bipyridinyl-3-yl}-isonicotinamide | 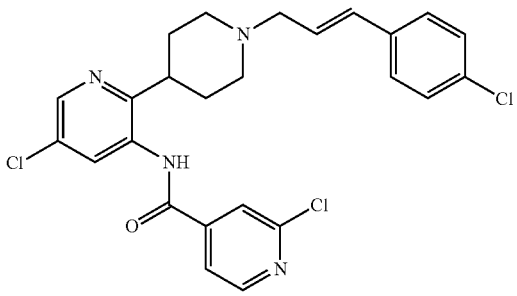 [SMILES: O=C(Nc1cc(Cl)cnc1C1CCN(C/C=C/c2ccc(Cl)cc2)CC1)c1ccnc(Cl)c1] | | 499/501/503 | 1.64 |

EXAMPLE 23

This Example illustrates the preparation of 2-Chloro-N-{5-chloro-1'-[(E)-3-(4-chloro-phenyl)-allyl]-1',2',3',4',5',6'-hexahydro-[2,4']bipyridinyl-3-yl}-isonicotinamide.

A mixture of trimethylchlorosilane and 1,2-dibromoethane (7:5 v/v, 0.125 ml) was added dropwise (keeping the T° C. below 50° C.) to a suspension of zinc powder (422 mg) in dimethylacetamide (3 ml). The mixture was stirred 20 min at room temperature then a solution of 1-(t-butoxycarbonyl)-4-iodo-piperidine (1.62 g, prepared in 2 steps from 1-(t-butoxycarbonyl)-piperidin-4-one according to J. Org. Chem. 2004, 5120) in dimethylacetamide (3 ml) was added dropwise over 5 min (slightly exothermic). The resulting mixture was stirred at room temperature for 30 min then cannulated into a mixture of 2,5-dichloro-3-aminopyridine (603 mg), copper(I) iodide (42 mg) and PdCl2(dppf) (91 mg) in dimethylacetamide (5 ml). The resulting mixture was stirred at 80° C. for 3 hours, cooled to room temperature, poured into water, extracted with ethyl acetate, dried over sodium sulfate and concentrated in vacuo. The residue was subjected to silica gel chromatography (ethyl acetate:cyclohexane 3:7) to afford 3-amino-5-chloro-3',6'-dihydro-2'H-[2,4']bipyridinyl-1'-carboxylic acid tert-butyl ester (535 mg) as a yellow solid. ¹H NMR (400 MHz, CDCl$_3$) 1.4 (s, 9H), 1.8 (m, 4H), 2.6 (m, 1H), 2.8 (m, 2H), 3.7 (br s, 2H), 4.2 (m, 2H), 6.9 (s, 1H), 7.9 (s, 1H).

The product thus obtained (448 mg) was treated as described in Example 1, Steps D and E to afford the title product (455 mg) as a white solid. M.p. 63-67° C.; $^1$H NMR (400 MHz, CDCl$_3$) 1.9 (m, 2H), 2.2 (m, 4H), 2.7 (m, 1H), 3.2 (m, 2H), 3.3 (m, 2H), 6.2 (dt, J=18, 9 Hz, 1H), 6.5 (d, J=18 Hz, 1H), 7.1-7.3 (m, 4H), 7.7 (d, J=5.2 Hz, 1H), 7.8 (s, 1H), 7.9 (m, 1H, NH), 8.3 (d, J=2.4 Hz, 1H), 8.4 (d, J=2.4 Hz, 1H), 8.6 (d, J=4.8 Hz, 1H), 8.7 (d, J=5.5 Hz, 1H); Retention Time HPLC 1.53 min; MS (ES+) 501/503/505 (M+H$^+$).

The following compounds were prepared according to procedures analogous to those described in Example 23:

| Compound Name | Structure | M.p (° C.) | MH$^+$ | Retention Time (min) |
|---|---|---|---|---|
| 2-chloro-N-{4-chloro-1'-[(E)-3-(4-chloro-phenyl)-allyl]-1',2',3',4',5',6'-hexahydro-[2,4']bipyridinyl-3-yl}-isonicotinamide | 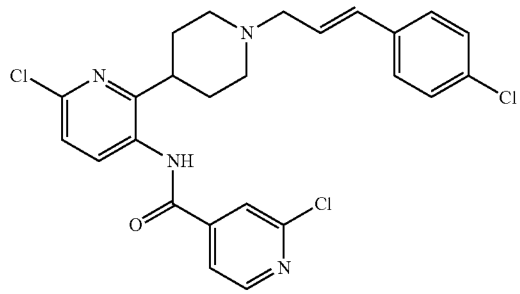 [SMILES: O=C(Nc1ccc(Cl)nc1C1CCN(C/C=C/c2ccc(Cl)cc2)CC1)c1ccnc(Cl)c1] | 80-85 | 499/501/503 | 1.55 |
| N-(5-bromo-3-{1-[(E)-3-(4-chloro-phenyl)-allyl]-piperidin-4-yl}-pyrazin-2-yl)-2-chloro-isonicotinamide | 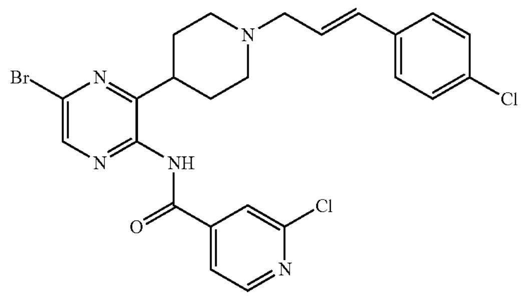 | | 548/550 | 1.33 |

The following compounds (Tables EX23.1-EX23.11) were prepared applying Suzuki cross coupling reactions as described in Schemes 8-13. Reaction conditions described in the literature [P. R Eastwood, THL 41, 3705 (2000) for example] or as described above were applied.

TABLE EX23.1

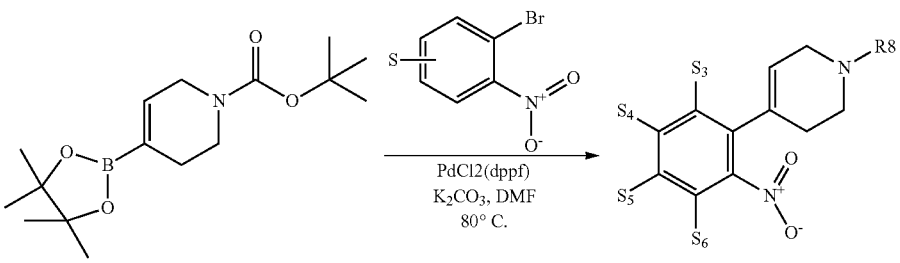

| Compound No | R$^8$ | S$_3$ | S$_4$ | S$_5$ | S$_6$ | Mp (° C.) | MH$^+$ —BOC | Retention time (min) |
|---|---|---|---|---|---|---|---|---|
| EX23-1-2 | BOC | H | H | F | H | | 323/322 | 2.22 |
| EX23-1-3 | BOC | H | H | CF$_3$ | H | | 373/372 | 2.30 |
| EX23-1-4 | BOC | H | H | OCH$_3$ | H | | 235/234 | 2.23 |
| EX23-1-5 | BOC | CH$_3$ | H | H | H | | 219/220 | 2.19 |
| EX23-1-6 | BOC | H | H | H | CH$_3$ | 100-102 | 219/220 | 2.22 |
| EX23-1-7 | BOC | H | H | COOCH$_3$ | H | | 263/264 | 2.08 |

TABLE EX23.2

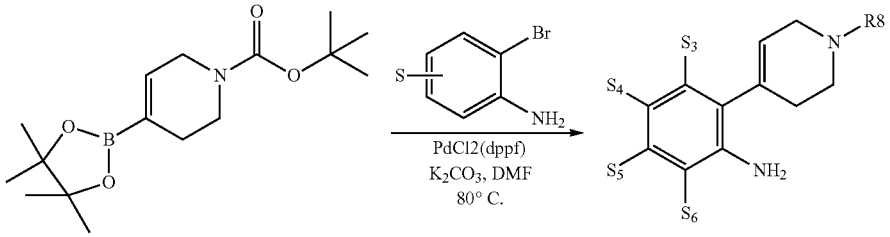

| Compound No | R⁸ | S₃ | S₄ | S₅ | S₆ | Mp (°C.) | MH⁺ —BOC | Retention time (min) |
|---|---|---|---|---|---|---|---|---|
| EX23-2-1 | BOC | H | H | H | F | 100-102 | 19/3194 | 2.15 |
| EX23-2-2 | BOC | H | F | H | F |  | 211/210 | 2.12 |
| EX23-2-3 | BOC | H | i-Pr | H | H |  | 217/216 | 2.11 |
| EX23-2-4 | BOC | H | F | F | F |  | 229/230 | 2.21 |
| EX23-2-5 | BOC | H | OCF₃ | H | H |  | 259/260 | 2.22 |
| EX23-2-6 | BOC | H | F | H | H |  | 193/194 | 2.02 |

TABLE EX23.3

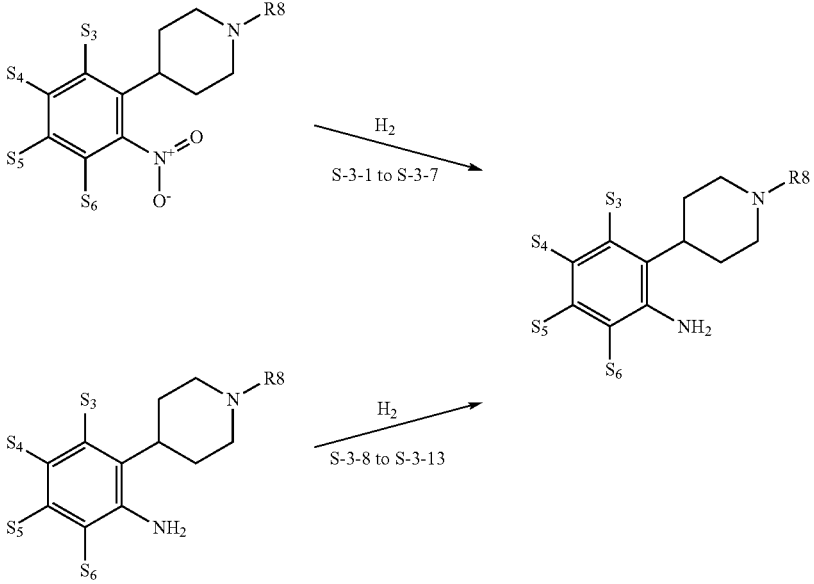

| Compound No | R⁸ | S₃ | S₄ | S₅ | S₆ | Mp (°C.) | MH⁺ —BOC | Retention time (min) |
|---|---|---|---|---|---|---|---|---|
| EX23-3-1 | BOC | H | H | CH₃ | H |  | 191/192 | 1.90 |
| EX23-3-2 | BOC | H | H | F | H |  | 195/196 | 2.05 |
| EX23-3-3 | BOC | H | H | CF₃ | H |  | 245/246 | 2.22 |
| EX23-3-4 | BOC | H | H | OCH₃ | H |  | 207/208 | 1.92 |
| EX23-3-5 | BOC | CH3 | H | H | H |  | 191/192 | 1.87 |
| EX23-3-6 | BOC | H | H | H | CH₃ |  | 191/192 | 2.06 |
| EX23-3-7 | BOC | H | H | COOCH₃ | H |  | 235/236 | 2.00 |
| EX23-3-8 | BOC | H | H | H | F | 123-126 | 195/196 | 2.12 |
| EX23-3-9 | BOC | H | F | H | F |  | 213/214 | 2.10 |
| EX23-3-10 | BOC | H | i-Pr | H | H |  | 219/220 | 2.00 |
| EX23-3-11 | BOC | H | F | F | F |  | 231/232 | 2.16 |
| EX23-3-12 | BOC | H | OCF₃ | H | H |  | 261/262 | 2.18 |
| EX23-3-13 | BOC | H | F | H | H |  | 195/196 | 1.87 |

TABLE EX23.4

| Compound No | R$^8$ | S$_3$ | S$_4$ | S$_5$ | S$_6$ | Mp (° C.) | MH$^+$ —BOC | Retention time (min) |
|---|---|---|---|---|---|---|---|---|
| EX23-4-1 | BOC | H | H | CH$_3$ | H | amorph | 330/332/333 | 2.14 |
| EX23-4-2 | BOC | H | H | F | H | amorph | 334/336/337 | 2.11 |
| EX23-4-3 | BOC | H | H | CF$_3$ | H | amorph | 384/386/387 | 2.22 |
| EX23-4-4 | BOC | H | H | OCH$_3$ | H | amorph | 346/348/349 | 2.07 |
| EX23-4-5 | BOC | CH$_3$ | H | H | H | amorph | 330/332/333 | 2.04 |
| EX23-4-6 | BOC | H | H | H | CH$_3$ | | 330/332/333 | 2.06 |
| EX23-4-7 | BOC | H | H | COOCH$_3$ | H | amorph | 374/376/377 | 2.05 |
| EX23-4-8 | BOC | H | H | H | F | amorph | 334/336/337 | 2.02 |
| EX23-4-9 | BOC | H | F | H | F | amorph | 352/354/355 | 2.08 |
| EX23-4-10 | BOC | H | i-Pr | H | H | amorph | 358/360/361 | 2.25 |
| EX23-4-11 | BOC | H | F | F | F | amorph | 370/372/372 | 2.25 |
| EX23-4-12 | BOC | H | OCF$_3$ | H | H | 227-230 | 400/402/403 | 2.22 |

TABLE EX23.5

| Compound No | R$^8$ | S$_3$ | S$_4$ | S$_5$ | S$_6$ | Mp (° C.) | MH$^+$ | Retention time (min) |
|---|---|---|---|---|---|---|---|---|
| EX23-5-1 | H | H | H | CH$_3$ | H | amorph | 330/332/333 | 1.17 |
| EX23-5-2 | H | H | H | F | H | amorph | 334/336/337 | 1.18 |
| EX23-5-3 | H | H | H | CF$_3$ | H | amorph | 384/386/387 | 1.35 |
| EX23-5-4 | H | H | H | OCH$_3$ | H | amorph | 346/348/349 | 1.17 |
| EX23-5-5 | H | CH$_3$ | H | H | H | amorph | 330/332/333 | 1.12 |
| EX23-5-6 | H | H | H | H | CH3 | amorph | 330/332/333 | 1.15 |
| EX23-5-7 | H | H | H | COOCH$_3$ | H | amorph | 374/376/377 | 1.13 |
| EX23-5-8 | H | H | H | H | F | amorph | 334/336/337 | 1.14 |
| EX23-5-9 | H | H | F | H | F | amorph | 352/354/355 | 1.22 |
| EX23-5-10 | H | H | i-Pr | H | H | amorph | 358/360/361 | 1.37 |
| EX23-5-11 | H | H | F | F | F | amorph | 370/372/372 | 1.28 |
| EX23-5-12 | H | H | OCF$_3$ | H | H | amorph | 400/402/403 | 1.30 |

TABLE EX23.6

| Compound No | R8 | S3 | S4 | S5 | S6 | Mp (° C.) | MH+ | Retention time (min) |
|---|---|---|---|---|---|---|---|---|
| EX23-6-1 | 4-chlorocinnamyl | H | H | CH3 | H | 203-206 | 480/482/483 | 1.51 |
| EX23-6-2 | 4-chlorocinnamyl | H | H | F | H | | 484/486/487 | 1.49 |
| EX23-6-3 | 4-chlorocinnamyl | H | H | CF3 | H | | 534/536/537 | 1.59 |
| EX23-6-4 | 4-chlorocinnamyl | H | H | OCH3 | H | | 496/498/499 | 1.47 |
| EX23-6-5 | 4-chlorocinnamyl | CH3 | H | H | H | amorph | 480/482/483 | 1.49 |
| EX23-6-6 | 4-chlorocinnamyl | H | H | H | CH3 | 90-93 | 480/482/483 | 1.54 |
| EX23-6-7 | 4-chlorocinnamyl | H | H | COOCH3 | H | 92-95 | 524/526/527 | 1.52 |
| EX23-6-8 | 4-chlorocinnamyl | H | H | H | F | | 484/486/487 | 1.44 |
| EX23-6-9 | 4-chlorocinnamyl | H | F | H | F | 221-223 | 502/504/505 | 1.49 |
| EX23-6-10 | 4-chlorocinnamyl | H | i-Pr | H | H | amorph | 508/510/511 | 1.61 |
| EX23-6-11 | 4-chlorocinnamyl | H | F | F | F | amorph | 520/522/523 | 1.53 |
| EX23-6-12 | 4-chlorocinnamyl | H | OCF3 | H | H | | 550/552/553 | 1.61 |
| EX23-6-13 | 4-chlorocinnamyl | H | F | H | H | 165-167 | 484/486/487 | 1.49 |

TABLE EX23.7

| Compound No | R8 | S3 | S4 | S5 | S6 | Mp (° C.) | MH+ —BOC | Retention time (min) |
|---|---|---|---|---|---|---|---|---|
| EX23-7-1 | BOC | H | F | H | F | amorph | 350/352/353 | 2.07 |
| EX23-7-2 | BOC | H | i-Pr | H | H | 167-169 | 356/358/359 | 2.27 |
| EX23-7-3 | BOC | H | F | F | F | 169-171 | 368/370/371 | 2.13 |
| EX23-7-4 | BOC | H | OCF3 | H | H | amorph | 398/400/401 | 2.23 |
| EX23-7-5 | BOC | H | F | H | H | amorph | 332/334/335 | 2.12 |

TABLE EX23.8

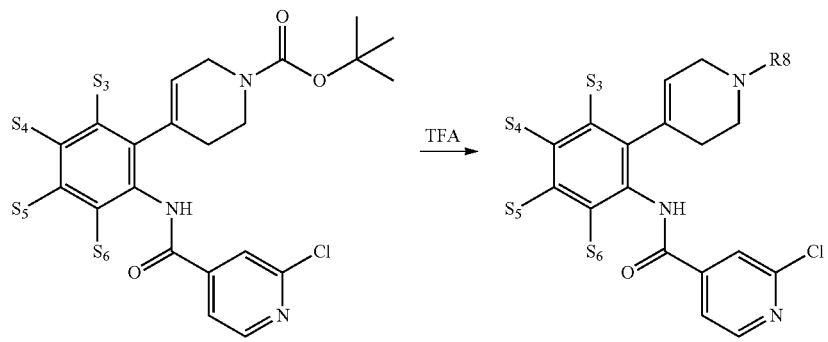

| Compound No | R⁸ | S₃ | S₄ | S₅ | S₆ | Mp (° C.) | MH⁺ | Retention time (min) |
|---|---|---|---|---|---|---|---|---|
| EX23-8-1 | H | H | F | H | F | | | |
| EX23-8-2 | H | H | i-Pr | H | H | amorph | 356/358/359 | 1.33 |
| EX23-8-3 | H | H | F | F | F | | | |
| EX23-8-4 | H | H | OCF₃ | H | H | amorph | 398/400/401 | 1.37 |
| EX23-8-5 | H | H | F | H | H | amorph | 332/334/335 | 1.09 |

TABLE EX23.9

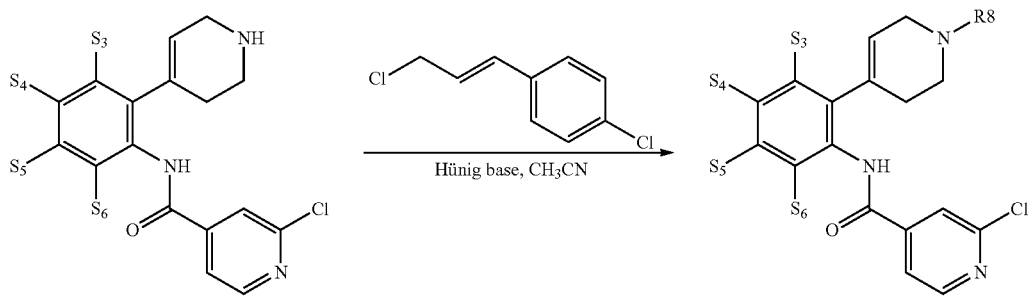

| Compound No | R⁸ | S₃ | S₄ | S₅ | S₆ | Mp (° C.) | MH⁺ | Retention time (min) |
|---|---|---|---|---|---|---|---|---|
| EX23-9-1 | 4-chlorocinnamyl | H | F | H | F | | | |
| EX23-9-2 | 4-chlorocinnamyl | H | i-Pr | H | H | amorph | 506/508/509 | 1.67 |
| EX23-9-3 | 4-chlorocinnamyl | H | F | F | F | | | |
| EX23-9-4 | 4-chlorocinnamyl | H | OCF₃ | H | H | | 548/550/551 | 1.66 |
| EX23-9-5 | 4-chlorocinnamyl | H | F | H | H | amorph | 482/484/485 | 1.47 |

TABLE EX23.10

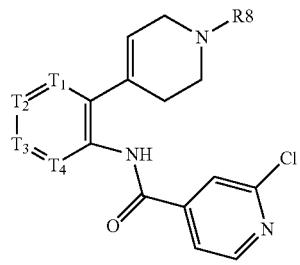

| Compound No | R⁸ | T₁ | T₂ | T₃ | T₄ | Mp (° C.) | MH⁺ | Retention time (min) |
|---|---|---|---|---|---|---|---|---|
| EX23-10-1 | 4-chlorocinnamyl | N | C—Me | CH | CH | | 420/422 | 1.27 |
| EX23-10-2 | 4-bromocinnamyl | N | C—Me | CH | CH | | 525/526 | 1.29 |
| EX23-10-3 | 4-chlorocinnamyl | N | C—Br | CH | N | | 546/548 | 1.37 |
| EX23-10-4 | 4-chlorocinnamyl | CH | N | C—Cl | N | | 502/504 | 1.30 |
| EX23-10-5 | 4-chlorocinnamyl | C—Cl | N | CH | CH | | 501/503 | 1.54 |
| EX23-10-6 | 4-chlorocinnamyl | C—Cl | N | C—Cl | CH | | 535/537 | 1.63 |

TABLE EX23.10-continued

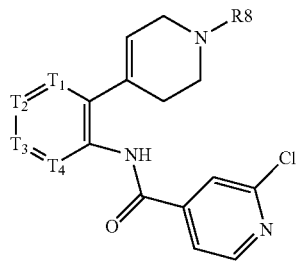

| Compound No | R⁸ | T₁ | T₂ | T₃ | T₄ | Mp (°C.) | MH⁺ | Retention time (min) |
|---|---|---|---|---|---|---|---|---|
| EX23-10-7 | 4-chlorocinnamyl | CH | C—CF₃ | CH | N | | 533/535 | 1.39 |
| EX23-10-8 | 4-chlorocinnamyl | N | C—Cl | CH | CH | | 501/503 | 1.34 |
| EX23-10-9 | 4-bromocinnamyl | N | C—Cl | CH | CH | | 545/547 | 1.36 |
| EX23-10-10 | 4-chlorocinnamyl | S | CH | CH | — | | 470/472 | 1.38 |
| EX23-10-11 | 4-chlorocinnamyl | S | C—Cl | CH | — | | 506/508 | 1.43 |

TABLE EX23.11

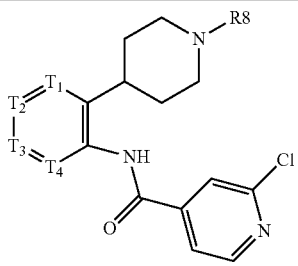

| Compound No | R⁸ | T₁ | T₂ | T₃ | T₄ | Mp (°C.) | MH⁺ | Retention time (min) |
|---|---|---|---|---|---|---|---|---|
| EX23-11-1 | 4-chlorocinnamyl | N | C—Me | CH | CH | | 481/483 | 1.33 |
| EX23-11-2 | 4-bromocinnamyl | N | C—Me | CH | CH | | 527/529/530 | 1.33 |
| EX23-11-3 | 4-chlorocinnamyl | CH | CF₃ | CH | N | | 535/537 | 1.35 |
| EX23-11-4 | 4-bromocinnamyl | CH | CF₃ | CH | N | | 581/582.5 | 1.36 |

EXAMPLE 24

This Example illustrates the pesticidal/insecticidal properties of compounds of formula (I).

Test against were performed as follows:

*Spodoptera littoralis* (Egyptian Cotton Leafworm)

Cotton leaf discs were placed on agar in a 24-well microtiter plate and sprayed with test solutions at an application rate of 200 ppm. After drying, the leaf discs were infested with 5 L₁ larvae. The samples were checked for mortality, repellent effect, feeding behaviour, and growth regulation 3 days after treatment (DAT). The following compounds gave at least 80% control of *Spodoptera littoralis*: Iaaa-3 and Iaaa-49.

*Heliothis virescens* (Tobacco Budworm):

Eggs (0-24 h old) were placed in 24-well microtiter plate on artificial diet and treated with test solutions at an application rate of 200 ppm by pipetting. After an incubation period of 4 days, samples were checked for egg mortality, larval mortality, and growth regulation. The following compounds gave at least 80% control of *Heliothis virescen*: Ia-49, Ia-50, Ia-53, Iaaa-3, Iaaa-26, Iaaa-49, Iaaa-52, Iaab-26 and Iaac-26.

*Plutella xylostella* (Diamond Back Moth):

24-well microtiter plate (MTP) with artificial diet was treated with test solutions at an application rate of 18.2 ppm by pipetting. After drying, the MTP's were infested with larvae (L2) (10-15 per well). After an incubation period of 5 days, samples were checked for larval mortality, antifeedant and growth regulation. The following compounds gave at least 80% control of *Plutella xylostella*: Ia-49, Ia-53, Iaaa-3, Iaaa-26, Iaaa-49 and Iaac-26.

*Aedes aegypti* (Yellow Fever Mosquito):

10-15 *Aedes* larvae (L2) together with a nutrition mixture are placed in 96-well microtiter plates. Test solutions at an application rate of 2 ppm are pipetted into the wells. 2 days later, insects were checked for mortality and growth inhibition. The following compounds gave at least 80% control of *Aedes aegypti*: Ia-53, Iaaa-3, Iaaa-26, Iaaa-49, Iaaa-52, Iaab-26, Iaac-26 and Iaai-26.

The invention claimed is:
1. A compound of formula I'

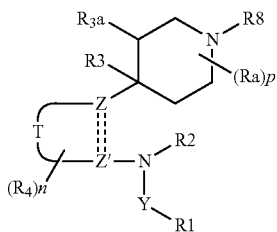

where Y is a single bond, C=O, C=S or $S(O)_m$, where m is 0, 1 or 2;
the ring

is a 6 membered aromatic ring or is a 5 or 6 membered heteroaromatic ring;
Z and Z' are joined by a single or a double bond and are =C— or —N— provided that both are not N;
$R^1$ is hydrogen, optionally substituted alkyl, optionally substituted alkoxycarbonyl, optionally substituted alkylcarbonyl, aminocarbonyl, optionally substituted alkylaminocarbonyl, optionally substituted dialkylaminocarbonyl, optionally substituted aryl, optionally substituted heteroaryl, optionally substituted alkoxy, optionally substituted aryloxy, optionally substituted heteroaryloxy, optionally substituted heterocyclyloxy, cyano, optionally substituted alkenyl, optionally substituted alkynyl, optionally substituted cycloalkyl, optionally substituted cycloalkenyl, formyl, optionally substituted heterocyclyl, optionally substituted alkylthio, NO or $NR^{13}R^{14}$ where $R^{13}$ and $R^{14}$ are independently hydrogen, $COR^{15}$, optionally substituted alkyl, optionally substituted aryl, optionally substituted heteroaryl, optionally substituted heterocyclyl or $R^{13}$ and $R^{14}$ together with the N atom to which they are attached form a group —N=C($R^{16}$)—$NR^{17}R^{18}$ or $R^{13}$ and $R^{14}$ together with the N atom to which they are attached form a five, six or seven-membered heterocyclic ring which may contain one or two further heteroatoms selected from O, N or S and which may be optionally substituted by one or two $C_{1-6}$ alkyl groups; $R^{15}$ is H, optionally substituted alkyl, optionally substituted alkoxy, optionally substituted aryl, optionally substituted aryloxy optionally substituted heteroaryl, optionally substituted heteroaryloxy or $NR^{19}R^{20}$; $R^{16}$, $R^{17}$ and $R^{18}$ are each independently H or lower alkyl; $R^{19}$ and $R^{20}$ are independently optionally substituted alkyl, optionally substituted aryl or optionally substituted heteroaryl;
$R^2$ is H, hydroxy, optionally substituted alkoxy or optionally substituted alkyl; or $R^1$ and $R^2$ together with the groups Y and N form a 5- or 6-membered heterocyclic ring which may optionally contain one further heteroatom selected from O, N or S and which may be optionally substituted by $C_{1-4}$ alkyl, $C_{1-4}$ haloalkyl or halogen;
$R^3$ is H, OH, halogen or optionally substituted alkyl;
$R^{3a}$ is H or $R^3$ and $R^{3a}$ together form a bond;
each $R^4$ is independently halogen, nitro, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio or $R^{21}R^{22}N$ where $R^{21}$ and $R^{22}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkyl, $C_{1-6}$ alkoxy($C_{1-6}$)alkyl, $C_{1-6}$ alkoxycarbonyl or $R^{21}$ and $R^{22}$ together with the N atom to which they are attached form a five, six or seven-membered heterocyclic ring which may contain one or two further heteroatoms selected from O, N or S and which may be optionally substituted by one or two $C_{1-6}$ alkyl groups, or 2 adjacent groups $R^4$ together with the carbon atoms to which they are attached form a 4, 5, 6, or 7 membered carbocyclic or heterocyclic ring which may be optionally substituted by halogen;
n is 0, 1, 2, 3 or 4;
each Ra is independently halogen, hydroxy, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio, optionally substituted arylthio or $R^{23}R^{24}N$ where $R^{23}$ and $R^{24}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkyl, $C_{1-6}$ alkoxy($C_{1-6}$)alkyl, $C_{1-6}$ alkoxycarbonyl or $R^{23}$ and $R^{24}$ together with the N atom to which they are attached form a five, six or seven-membered heterocyclic ring which may contain one or two further heteroatoms selected from O, N or S and which may be optionally substituted by one or two $C_{1-6}$ alkyl groups, or two Ra groups attached to the same carbon atom are =O, =S, =NRb, =CRcRd where Rb, Rc and Rd are independently H or optionally substituted alkyl; p is 0, 1, 2, 3 or 4 or one or more salts or N-oxides thereof;
and $R^8$ is —C($R^{51}$)($R^{52}$)—[$CR^{53}$=$CR^{54}$]z-$R^{55}$ where z is 1 or 2, $R^{51}$ and $R^{52}$ are each independently H or $C_{1-2}$ alkyl, $R^{53}$ and $R^{54}$ are each independently H, halogen, $C_{1-4}$ alkyl or $C_{1-4}$ haloalkyl and $R^{55}$ is phenyl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino or heteroaryl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino or salts or N-oxides thereof.

2. A compound of formula IIa

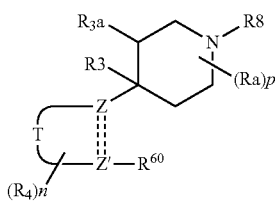

wherein; the ring

and $R^3$, $R^{3a}$, $R^4$, $R^8$, Ra, n and p are as defined in relation to formula I' in claim 1 and $R^{60}$ is $NH_2$, $NO_2$ or halogen; or a compound of formula (IIb)

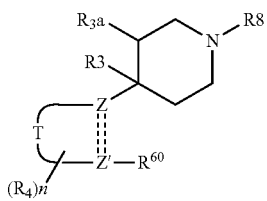

wherein; the ring

each Ra is independently halogen, hydroxy, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio, optionally substituted arylthio or $R^{23}R^{24}N$ where $R^{23}$ and $R^{24}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkyl, $C_{1-6}$ alkoxy($C_{1-6}$)alkyl, $C_{1-6}$ alkoxycarbonyl or $R^{23}$ and $R^{24}$ together with the N atom to which they are attached form a five, six or seven-membered heterocyclic ring which may contain one or two further heteroatoms selected from O, N or S and which may be optionally substituted by one or two $C_{1-6}$ alkyl groups, or two Ra groups attached to the same carbon atom are =O, =S, =NRb, =CRcRd where Rb, Rc and Rd are independently H or optionally substituted alkyl; p is 0, 1, 2, 3 or 4 or one or more salts or N-oxides thereof;

and $R^4$, $R^{60}$ and n are as defined in relation to formula IIa, $R^3$ and $R^{3a}$ are both H or together form a bond and $R^8$ is methyl, benzyl or $COOC_{1-6}$alkyl provided that the compound is not tert-butyl 4-(2-aminophenyl)piperidine-1-carboxylate or 2,4-diamino-5-(1-benzyl-4-piperidinyl)-pyrimidine.

3. An insecticidal acaricidal and nematicidal composition comprising an insecticidally, acaricidally or nematicidally effective amount of a compound of formula I

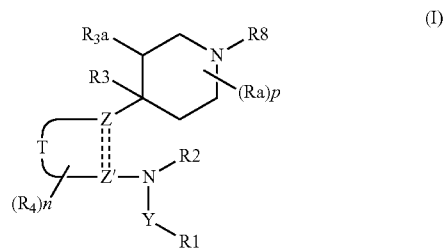

where Y is a single bond, C=O, C=S or $S(O)_m$, where m is 0, 1 or 2;
the ring

is a pyridine ring;
$R^1$ is hydrogen, optionally substituted alkyl, optionally substituted alkoxycarbonyl, optionally substituted alkylcarbonyl, aminocarbonyl, optionally substituted alkylaminocarbonyl, optionally substituted dialkylaminocarbonyl, optionally substituted aryl, optionally substituted heteroaryl, optionally substituted alkoxy, optionally substituted aryloxy, optionally substituted heteroaryloxy, optionally substituted heterocyclyloxy, cyano, optionally substituted alkenyl, optionally substituted alkynyl, optionally substituted cycloalkyl, optionally substituted cycloalkenyl, formyl, optionally substituted heterocyclyl, optionally substituted alkylthio, NO or $NR^{13}R^{14}$ where $R^{13}$ and $R^{14}$ are independently hydrogen, $COR^{15}$, optionally substituted alkyl, optionally substituted aryl, optionally substituted heteroaryl, optionally substituted heterocyclyl or $R^{13}$ and $R^{14}$ together with the N atom to which they are attached form a group $-N=C(R^{16})-NR^{17}R^{18}$ or $R^{13}$ and $R^{14}$ together with the N atom to which they are attached form a five, six or seven-membered heterocyclic ring which may contain one or two further heteroatoms selected from O, N or S and which may be optionally substituted by one or two $C_{1-6}$ alkyl groups; $R^{15}$ is H, optionally substituted alkyl, optionally substituted alkoxy, optionally substituted aryl, optionally substituted aryloxy optionally substituted heteroaryl, optionally substituted heteroaryloxy or $NR^{19}R^{20}$; $R^{16}$, $R^{17}$ and $R^{18}$ are each independently H or lower alkyl; $R^{19}$ and $R^{20}$ are independently optionally substituted alkyl, optionally substituted aryl or optionally substituted heteroaryl;
$R^2$ is H, hydroxy, optionally substituted alkoxy or optionally substituted alkyl; or $R^1$ and $R^2$ together with the groups Y and N form a 5- or 6-membered heterocyclic ring which may optionally contain one further heteroatom selected from O, N or S and which may be optionally substituted by $C_{1-4}$ alkyl, $C_{1-4}$ haloalkyl or halogen;

$R^3$ is H, OH, halogen or optionally substituted alkyl;

$R^{3a}$ is H or $R^3$ and $R^{3a}$ together form a bond;

each $R^4$ is independently halogen, nitro, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio or $R^{21}R^{22}N$ where $R^{21}$ and $R^{22}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkyl, $C_{1-6}$ alkoxy($C_{1-6}$)alkyl, $C_{1-6}$ alkoxycarbonyl or $R^{21}$ and $R^{22}$ together with the N atom to which they are attached form a five, six or seven-membered heterocyclic ring which may contain one or two further heteroatoms selected from O, N or S and which may be optionally substituted by one or two $C_{1-6}$ alkyl groups, or 2 adjacent groups $R^4$ together with the carbon atoms to which they are attached form a 4, 5, 6, or 7 membered carbocyclic or heterocyclic ring which may be optionally substituted by halogen;

n is 0, 1, 2, 3 or 4;

$R^8$ is optionally substituted alkyl, optionally substituted alkenyl, optionally substituted alkynyl, optionally substituted cycloalkyl, optionally substituted aryl, optionally substituted alkoxy, optionally substituted aryloxy, optionally substituted alkoxycarbonyl, optionally substituted alkylcarbonyl or optionally substituted alkenylcarbonyl;

each Ra is independently halogen, hydroxy, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio, optionally substituted arylthio or $R^{23}R^{24}N$ where $R^{23}$ and $R^{24}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkyl, $C_{1-6}$ alkoxy($C_{1-6}$)alkyl, $C_{1-6}$ alkoxycarbonyl or $R^{23}$ and $R^{24}$ together with the N atom to which they are attached form a five, six or seven-membered heterocyclic ring which may contain one or two further heteroatoms selected from O, N or S and which may be optionally substituted by one or two $C_{1-6}$ alkyl groups, or two Ra groups attached to the same carbon atom are =O, =S, =NRb, =CRcRd where Rb, Rc and Rd are independently H or optionally substituted alkyl; p is 0, 1, 2, 3 or 4 or one or more salts or N-oxides thereof.

\* \* \* \* \*